(12) United States Patent
Hart et al.

(10) Patent No.: US 9,399,016 B2
(45) Date of Patent: Jul. 26, 2016

(54) MATERIALS AND COMPLEXES FOR THE DELIVERY OF BIOLOGICALLY-ACTIVE MATERIALS TO CELLS

(75) Inventors: Stephen Lewis Hart, London (GB); Stephanie Grosse, London (GB); Alethea Bernice Tabor, London (GB); John Bosco Wong, London (GB); Martin Elbs, London (GB); Helen Claire Hailes, London (GB); Mohd Firouz Mohd Mustapa, London (GB)

(73) Assignee: UCL BUSINESS PLC, London (GB)

(\*) Notice: Subject to any disclaimer, the term of this patent is extended or adjusted under 35 U.S.C. 154(b) by 1134 days.

(21) Appl. No.: 12/227,735

(22) PCT Filed: May 30, 2007

(86) PCT No.: PCT/GB2007/002012
§ 371 (c)(1),
(2), (4) Date: May 27, 2009

(87) PCT Pub. No.: WO2007/138324
PCT Pub. Date: Dec. 6, 2007

(65) Prior Publication Data
US 2010/0184831 A1    Jul. 22, 2010

(30) Foreign Application Priority Data

May 30, 2006   (GB) .................................. 0610636.3

(51) Int. Cl.
| | | |
|---|---|---|
| A61K 47/48 | (2006.01) | |
| A61P 35/00 | (2006.01) | |
| C07C 229/30 | (2006.01) | |
| C07K 2/00 | (2006.01) | |
| A61K 9/127 | (2006.01) | |
| A61K 9/00 | (2006.01) | |
| A61K 48/00 | (2006.01) | |
| C07C 217/28 | (2006.01) | |
| A61K 38/00 | (2006.01) | |

(52) U.S. Cl.
CPC ............. *A61K 9/1271* (2013.01); *A61K 9/0019* (2013.01); *A61K 47/48046* (2013.01); *A61K 47/48246* (2013.01); *A61K 47/48323* (2013.01); *A61K 47/48338* (2013.01); *A61K 47/48815* (2013.01); *A61K 48/0008* (2013.01); *A61K 48/0025* (2013.01); *A61K 48/0041* (2013.01); *C07C 217/28* (2013.01); *A61K 38/00* (2013.01)

(58) Field of Classification Search
None
See application file for complete search history.

(56) References Cited

U.S. PATENT DOCUMENTS

| 5,574,142 A | * | 11/1996 | Meyer et al. | ............... 536/23.1 |
| 7,138,381 B2 | * | 11/2006 | Baird et al. | ............... 514/44 R |
| 7,598,421 B2 | * | 10/2009 | Hailes et al. | ............... 564/295 |

FOREIGN PATENT DOCUMENTS

| WO | WO 96/15811 A1 | 5/1996 |
| WO | WO 98/54347 A1 | 12/1998 |
| WO | WO 03/047549 A2 | 6/2003 |
| WO | WO 2005/117985 A2 | 12/2005 |

OTHER PUBLICATIONS

Aissaoui, et al. (2004) "Novel Cationic Lipids Incorporating an Acid-Sensitive Acylhydrazone Linker: Synthesis and Transfection Properties", Journal of Medicinal Chemistry, 47(21): 5210-23.*
Meng, et al. (Jan. 12, 2004) "Efficient Transfection of Non-Proliferating Human Airway Epithelial Cells With a Synthetic Vector System", The Journal of Gene Medicine, 6(2): 210-21.*
Hayes, et al. (2006—First Published online Dec. 8, 2005) "Geneospheres: Self-Assembling Nucleic Acid-Lipid Nanoparticles Suitable for Targeted Gene Delivery", Gene Therapy, 13: 646-51.*
Martin-Herranz, et al. (2004) "Surface Functionalized Cationic Lipid-DNA Complexes for Gene Delivery: PEGylated Lamellar Complexes Exhibit Distinct DNA-DNA Interaction Regimes", Biophysical Society, 82(2); 1160-68.*
Sarah Boseley, Jul. 3, 2015, http://www.theguardian.com/science/2015/jul/03/gene-therapy-cystic-fibrosis-2020-scientists,  "Gene therapy treatment for cystic fibrosis may be possible by 2020, scientists say", Published in "theguardian" online, Guardian News and Media Limited, New York, NY, downloaded Sep. 27, 2015, 3 pages long.*

(Continued)

*Primary Examiner* — Robert M Kelly
(74) *Attorney, Agent, or Firm* — Yankwich & Associates, P.C.; Leon R. Yankwich; Michael R. Wesolowski

(57) ABSTRACT

The invention provides a peptide derivative of formula A-B-C wherein
A is a polycationic nucleic acid-binding component;
B is a spacer element peptide that is susceptible to cleavage within a cell; and
C is a cell surface receptor binding component.
The invention also provides a lipid derivative of general formula (I):

$$(PEG)_q\text{-Linker-Spacer-Cationic headgroup-carbon skeleton-(hydrophobic chain)}_o$$

wherein:
the Linker is a group susceptible to cleavage within a cell;
the Spacer is a group linking the Linker to the Cationic headgroup;
q denotes the number of PEG chains and q=1, 2 or 3;
o denotes the number of hydrophobic chains and o=1, 2 or 3;
the carbon skeleton is a group linking the hydrophobic chains to the cationic headgroup.
The peptide and lipid derivatives find use in non-viral gene delivery systems.

14 Claims, 22 Drawing Sheets

(56) References Cited

OTHER PUBLICATIONS

Nau, et al. (2010) "Penetration of Drugs through the Blood-Cerebrospinal Fluid/Blood-Brain Barrier for Treatment of Central Nervous System Infections", Clinical Microbiology Reviews, 23(4): 858-83.*

In re Alonso, 545 F.3d 1015, 88 USPQ.2d 1849 (Fed Cir 2008).*

Aissaoui et al., "Novel Cationic Lipids Incorporating an Acid-Sensitive Acylhydrazone Linker: Synthesis and Transfection Properties", J. Med. Chem., 47: 5210-5223 (2004).

Ajmani et al., "Enhanced transgene expression in rat brain cell cultures with a disulfide-containing cationic lipid", Neuroscience Letters, 277: 141-144 (1999).

Chapman, H.A., "Endosomal proteases in antigen presentation", Curr. Opin. Immunol., 18: 78-84 (2006).

Chiron et al., "Furin-mediated Cleavage of Pseudomonas Exotoxin-derived Chimeric Toxins", J. Biol. Chem., 272(50): 31707-31711 (1997).

Choi et al., "Protease-mediated phototoxicity of a polylysine-chlorin(e6) conjugate", Chem. Med. Chem., 1(10): 698-701(2006).

Chowdhury et al., "Fate of DNA targeted to the Liver by Asialoglycoprotein Receptor-mediated Endocytosis in Vivo. Prolongued Persistence in Cytoplasmic Vesicles After Partial Hepatectomy" J. Biol. Chem., 268(15): 11265-11271 (1993).

Cotten et al., "Receptor-Mediated Transport of DNA into Eukaryotic Cells", Methods in Enzymology, 217: 618-644 (1993).

Ferkol et al., "Gene Transfer into Respiratory Epithelial Cells by Targeting the Polymeric Immunoglobulin Receptor", J. Clin. Invest., 92(5): 2394-2400 (1993).

Fominaya et al., "Target Cell-Specific DNA Transfer Mediated by a Chimeric Multidomain Protein. Novel Non-Viral Gene Delivery System", J Biol. Chem., 271(18): 10560-10568 (1996).

Grosse et al., "Receptor-Targeting Smart Vectors for Efficient Gene Transfer to Tumours", Mol. Ther., 13: S414 (2006).

Harbottle et al., "An RGD-Oligolysine Peptide: A Prototype Construct for Integrin-Mediated Gene Delivery", Hum. Gene Ther., 9: 1037-1047 (1998).

Kollen et al., "Gluconoylated and Glycosylated Polylysines as Vectors for Gene Transfer Into Cystic Fibrosis Airway Epithelial Cells", Human Gene Therapy, 7: 1577-1586 (1996).

Li et al., "A novel gene delivery system targeting cells expressing VEGF receptors", Cell Research, 9: 11-25 (1999).

Tian et al., "A novel receptor-targeted gene delivery system for cancer gene therapy", Science in China (Series C) Life Sciences, 42(2): 216-224 (1999).

Wagner, E., "Transferrin-Polycation Conjugates as Carriers for DNA Uptake Into Cells", Proc. Natl. Acad. Sci. USA, 87: 3410-3414 (1990).

Zenke et al., "Receptor-Mediated Endocytosis of Transferrin-Polycation Conjugates: An Efficient Way to Introduce DNA Into Hematopoietic Cells", Proc. Natl. Acad. Sci. USA, 87: 3655-3659 (1990).

* cited by examiner (a) Neuro 2A (b) bEND.3

(c) 16HBE14o-

(a) Neuro 2A (b) 16HBE14o-

(a) Neuro 2A (b) 16HBE14o-

MATERIALS AND COMPLEXES FOR THE DELIVERY OF BIOLOGICALLY-ACTIVE MATERIALS TO CELLS

FIELD OF THE INVENTION

The present invention relates to lipid derivatives suitable for delivery of biologically-active materials, for example nucleic acids, proteins or small molecules, to a cell. The invention also relates to peptide derivatives having characteristic cleavable linkers. The invention further relates to the use of such lipids or such peptides or the two in combination, for example in prophylaxis, treatment and vaccination, or an in vitro laboratory setting.

BACKGROUND TO THE INVENTION

Gene delivery for therapy or other purposes is well-known, particularly for the treatment of diseases such as cystic fibrosis and certain cancers. The term refers to the delivery into a cell of a gene or part of a gene to correct some deficiency. In the present specification the term is used also to refer to any introduction of nucleic acid material into target cells, and includes gene vaccination and the in vitro production of commercially-useful proteins in so-called cell factories.

Cell delivery systems fall into three broad classes, namely those that involve direct injection of naked DNA, those that make use of viruses or genetically modified viruses and those that make use of non-viral delivery agents. Each has its advantages and disadvantages. Although viruses as delivery agents have the advantages of high efficiency and high cell selectivity, they have the disadvantages of toxicity, production of inflammatory responses and difficulty in dealing with large DNA fragments.

Non-viral gene delivery systems are based on the compaction of genetic material into nanometric particles by electrostatic interaction between the negatively charged phosphate backbone of DNA and cationic lipids, peptides or other polymers (Erbacher, P. et al, *Gene Therapy*, 1999, 6, 138-145). Various mechanisms for the action of these species have been suggested. An early suggestion was that membrane fusion between liposome and cell membrane occurs. More recently, endocytosis of intact complexes has been proposed. Complexes formed between the nucleic acid and the lipid become attached to the cell surface, then enter the cell by endocytosis. They then remain localised within a vesicle or endosome for some time and the nucleic acid component is released into the cytoplasm. Migration of the nucleic acid into the nucleus may then occur some time later, where a gene encoded by the nucleic acid may be expressed. Gene expression in the nucleus involves transcribing DNA into RNA and then translating that into protein.

The use of lipids, rather than viruses, for this purpose can result in lower toxicity, reduced cost, reasonably efficient targeting, and the ability to deal with large fragments of nucleic acid material. Unfortunately, lower transfection efficiencies have been noted.

Known complexes for gene delivery include "LID complexes". As used herein, the term "LID complex" represents a complex comprising a lipid, an integrin- (or other receptor-) binding peptide and DNA. LID complexes achieve transfection via an integrin-mediated pathway; they do not necessarily need to have an overall positive charge so undesirable serum interaction can be reduced. The lipid component shields both DNA and, to a degree, the peptide component from degradation, endosomal or otherwise. The peptide component can be designed to be cell-type specific or cell-surface receptor specific. For example the degree of integrin-specificity can confer a degree of cell specificity to the LID complex. Specificity results from the targeting to the cell-surface receptors (for example integrin receptors), and transfection efficiencies comparable to some adenoviral vectors can be achieved (Hart et al., "Lipid-Mediated Enhancement of Transfection by a Nonviral Integrin-Targeting Vector", *Hum. Gene Ther.*, 9: 575-585 (1998); Harbottle et al., "An RGD-Oligiolysine Peptide: A Prototype Construct for Integrin-Mediated Gene Delivery", *Hum. Gene Ther.*, 9(7): 1037-1047 (1998); and Jenkins et al., "An Integrin-targeted Non-viral Vector for Pulmonary Gene Therapy" *Gene Therapy*, 7, 393-400 (2000). Peptides that target human airway epithelial cells have been reported (WO02/072616). Peptides that dendritic cells have been reported (WO2004/108938).

The components of a LID complex associate electrostatically to form a Lipid/Peptide vector complex a so-called lipopolyplex type of vector (Hart et al. (1998) op. cit.; Meng et al., Efficient transfection of non-proliferating human airway epithelial cells with a synthetic vector system, *J. Gene Med.*, 6, 210-221 (2004); Parkes et al., High efficiency transfection of porcine vascular cells in vitro with a synthetic vector system, *J. Gene Med.*, 4, 292-299 (2002)). Lipid/peptide vectors transfect a range of cell lines and primary cell cultures with high efficiency and low toxicity: epithelial cells (40% efficiency), vascular smooth muscle cells (50% efficiency), endothelial cells (30% efficiency) and haematopoietic cells (10% efficiency). Furthermore, in vivo transfection of bronchial epithelium of mouse has been demonstrated (Jenkins et al., Formation of LID vector complexes in water alters physicochemical properties and enhances pulmonary gene expression in vivo, *Gene Ther.*, 10, 1026-1034 (2003), rat lung (Jenkins et al. (2000) op. cit.) and pig lung (Cunningham et al., Evaluation of a porcine model for pulmonary gene transfer using a novel synthetic vector, *J. Gene Med.*, 4, 438-446 2002)) and with efficiency comparable to that of an adenoviral vector (Jenkins et al. (2000) op. cit.).

A peptide for use in such LID complexes or lipid/peptide complexes must have two functionalities: a "head group" containing a cell surface receptor- (for example integrin-) recognition sequence and a "tail" that can bind DNA non-covalently. Known peptides in which these two components are covalently linked via a spacer in a way that does not interfere with their individual functions include peptides in which the "tail" is a polycationic nucleic acid-binding component, such as peptide 6 as described in WO96/15811.

Initial experiments involving LID complexes including such peptides have indicated insufficiently high transfection properties by the systemic, or intravenous, route of delivery. The likely problem, as described for other polycationic vectors is association of the vector with serum proteins and red cell membranes leading to poor solubility and rapid clearance of the vector by the reticuloendothelial systems (Dash, P. R., Read, M. L., Barrett, L. B., Wolfert, M. A., Seymour, L. W. (1999) *Gene Therapy* 6, 643-50). Vectors that have displayed some transfection activity by systemic administration have been effective largely in first-pass capillary beds of organs such as the liver and lung (Fenske, D. B., MacLachlan, I., Cullis, P. R. (2001). *Curr Opin Mol Ther* 3, 153-8). While such non-specific transfection activity may have some therapeutic applications, safe clinical use for specific applications demands vectors with far greater target specificity.

Regarding the lipid component of the LID complexes, cationic lipids for such a use were developed by Felgner in the late 1980s, and reported in Proc. Natl. Acad. Sci. USA 84, 7413-7417, 1987. A patent to Felgner et al that may be referred to is U.S. Pat. No. 5,264,618. Felgner developed the now commercially-available cationic liposome known by the trademark "Lipofectin" which consists of the cytofectin, DOTMA and the neutral lipid DOPE in a 1:1 ratio. Various other cationic liposome formulations have since been devised, most of which combine a synthetic cationic cytofectin and a neutral lipid. Cytofectins are positively charged molecules having a cationic head group attached via some spacer to a hydrophobic tail. In addition to the DOTMA analogues, there may be mentioned complex alkylamine/alkylamides, cholesterol derivatives, and synthetic derivatives of dipalmitol, phosphatidyl-ethanolamine, glutamate, imidazole and phosphonate. A review of these materials, and of the mechanisms by which they operate, may be found in Angew. Chem. Int. Ed. 37, 1768-1785, 1998. However, cationic vector systems vary enormously in their transfection efficiencies in the presence of serum, which clearly impacts on their potential uses for in vivo gene therapy.

WO 2005/117985 describes lipids comprising one or more polyethylene glycol (PEG) groups (i.e. PEGylated lipids) and shows that such PEGylated lipids display benefits over lipids without PEG groups (i. e. non-PEGylated lipids). In particular, the problem of rapid clearance of lipids by the reticuloendothelial system caused by their binding to plasma proteins and vector aggregation may be ameliorated by shielding the vectors with polymeric PEG moieties. However, PEGylation often leads to greatly reduced transfection efficiency, and there remains a need for lipids which are not rapidly cleared by the reticuloendothelial system, but display satisfactory transfection efficiency.

Non-viral gene therapy vectors have been the subject of recent reviews: Hart, S. L., (2005) *Current Drug Delivery*, 2, 1-6; Kostareloa, K. and Miller, A. D., (2005) *Chem. Soc. Rev.*, 34, 970-994.

SUMMARY OF THE INVENTION

The present invention provides a peptide derivative of formula A-B-C wherein
A is a polycationic nucleic acid-binding component;
B is a spacer element peptide that is susceptible to cleavage within a cell; and
C is a cell surface receptor binding component.
The present invention also provides a lipid derivative of general formula (I):

(PEG)$_q$-Linker-Spacer-Cationic headgroup-carbon skeleton-(hydrophobic chain)$_o$ wherein:
the Linker is a group susceptible to cleavage within a cell;
the Spacer is a group linking the Linker to the Cationic headgroup;
q denotes the number of PEG chains and q=1, 2 or 3;
o denotes the number of hydrophobic chains and o=1, 2 or 3;
the carbon skeleton is a group linking the hydrophobic chains to the cationic headgroup.

DETAILED DESCRIPTION OF THE INVENTION

Figure 1:
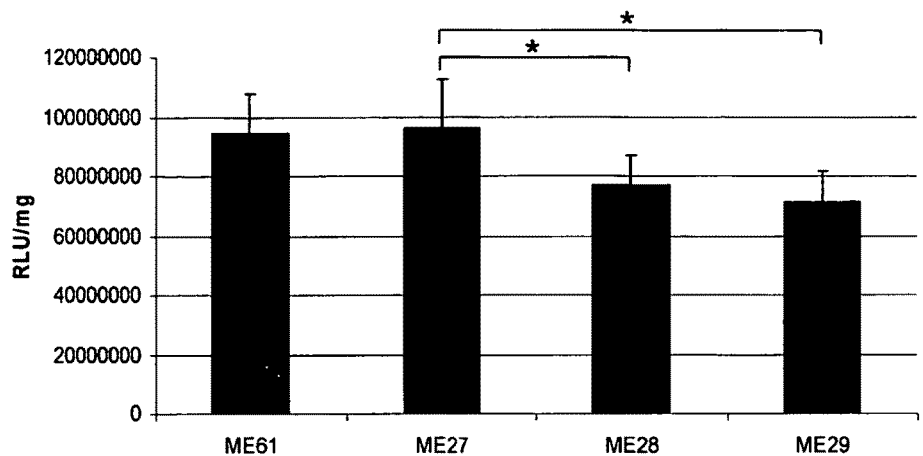
FIG. 1 shows the results of transfection with lipid-peptide-DNA (LPD) complexes containing a cleavable peptide (ME27, ME28, ME29) or non-cleavable peptide (ME61), performed in (a) mouse neuroblastoma cells, Neuro 2A, (b) mouse embryonic fibroblast, AJ3.1, (c) mouse endothelial cells, bEND.3, and (d) human bronchial epithelial cells, 16HBE14o-. Complexes were prepared with a lipofectin: peptide:pCI-Luc weight ratio of 2:4:1. Transfection incubation was performed for 4 h and luciferase activity was measured 24 h later. The relative light units (RLU) measured for 10 sec are expressed as means±s.e.m. per mg of protein. (* $p<0.05$).
Figure 1:
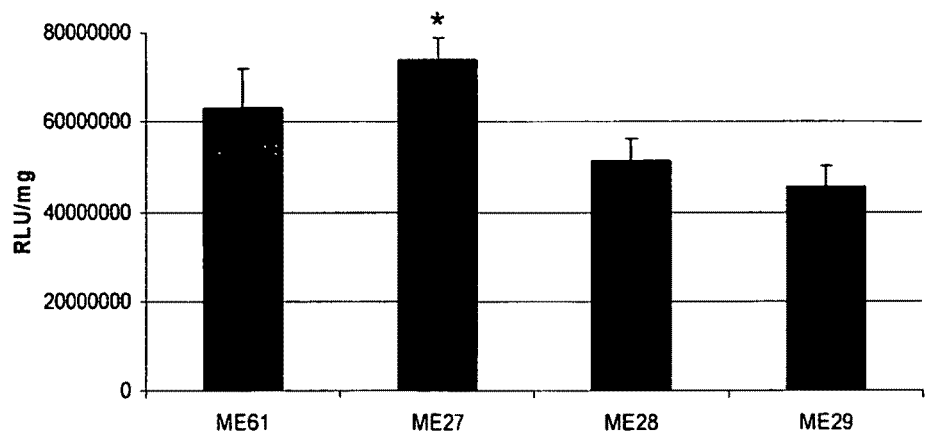
Figure 1:
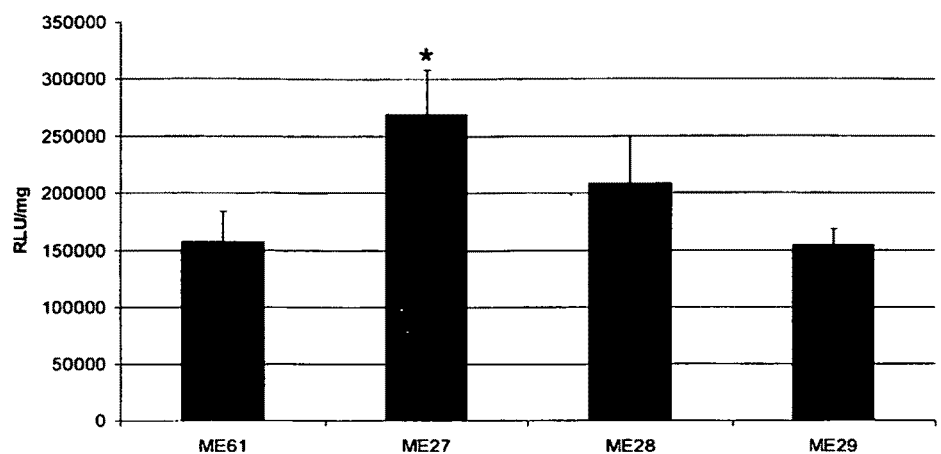
Figure 1:
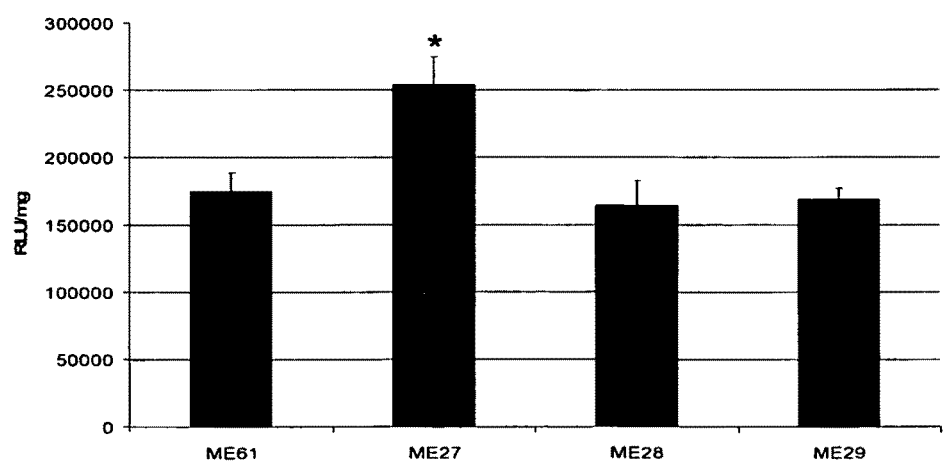

The present invention provides a peptide derivative of formula A-B-C wherein
A is a polycationic nucleic acid-binding component,
B is a spacer element peptide that is susceptible to cleavage within a cell, and
C is a cell surface receptor binding component.

It has been found that a peptide of the invention is more efficient in bringing about transfection of a target cell than prior art peptides without the spacer that is susceptible to cleavage within a cell.

The polycationic nucleic acid-binding component A is any polycation that is capable of binding to DNA or RNA. A polycation may be polycationic itself or it may have any number of cationic monomers provided the ability to bind to DNA or RNA is retained. For example, from 3 to 100 cationic monomers may be present, for example, from 10 to 20, for example from 14 to 18, for example, about 16.

An example of a nucleic acid-binding polycationic molecule is an oligopeptide comprising one or more cationic amino acids. Such an oligopeptide may, for example, be an oligo-lysine molecule, an oligo-histidine molecule, an oligo-arginine molecule, an oligo-ornithine molecule, an oligo diaminopropionic acid molecule, or an oligo-diaminobutyric acid molecule, or a combined oligomer comprising any combination of histidine, arginine, lysine, ornithine diaminopropionic acid, and diaminobutyric acid residues. Any of the above oligopeptides may have, for example, a total of from 3 to 35, for example, from 5 to 25 residues, preferably from 10 to 20 residues, for example, from 14 to 18 residues, for example 16 residues.

An oligolysine is particularly preferred, for example, having from 3 to 35, for example, from 2 to 25, for example, form 10 to 20 lysine residues, for example, from 13 to 19, for example, from 14 to 18, for example, from 15 to 17 residues, for example, 16 residues i.e. $[K]_{16}$ [SEQ ID NO: 1], "K" denoting lysine.

Further examples of polycationic components include dendrimers and polyethylenimine. Polyethylenimine (PEI) is a non-toxic, cross-linked cationic polymer with gene delivery potential (*Proc. Natl. Acad. Sci.*, 1995, 92, 7297-7301). Polyethylenimine is obtainable from Fluka (800 kDa) or from Sigma (50 kDa) or alternatively pre-diluted for transfection purposes from PolyPlus-tranfection (Illkirch, France). Typically, PEI is most efficient when used in a 9 fold excess over DNA, the excess ratio being calculated as PEI nitrogen:DNA phosphate, and at pH 5 to 8. Such parameters may be optimised in a manner familiar to the person skilled in the art.

The spacer element peptide B that is susceptible to cleavage within a cell may be any peptide that is susceptible to cleavage within a cell. Such peptides may be susceptible to cleavage within the endosome, lysosome, and/or cytoplasm of a cell. Susceptible to cleavage is understood herein to mean that the element is susceptible to cleavage over a timescale during which the components A and C remain in tact. Element B is cleaved more rapidly than the cellular peptide-degradation pathways take effect.

Preferably, the spacer element peptide is susceptible to enzymatic cleavage, reductive cleavage, or pH-dependent cleavage e.g. hydrolysis. In the case of enzymatic cleavage, in one aspect of the invention, preferred peptides are those which are susceptible to cleavage by an enzyme selected from NOX (NADH-oxidase), GILT (gamma-interferon-inducible lysosomal thiol reductase) and PDI (protein disulfide isomerase). In another aspect of the invention, preferred peptides are those which are susceptible to cleavage by an enzyme which is present in the endosome, for example an endosomal protease, such as furin or cathepsin.

Preferably the spacer element peptide B comprises a group selected from:
   a) a peptide chain comprising a disulfide-linkage;
   b) a peptide chain comprising an ester-linkage;
   c) an amino acid sequence susceptible to cleavage by furin; and
   d) an amino acid sequence susceptible to cleavage by a cathepsin enzyme The disulfide linkage is preferably one that is stable under normal atmospheric and physiological conditions, but that may be reductively cleaved in an endosome. Similarly, an ester linkage in a peptide chain of the invention is preferably one that is stable at neutral pH, but is cleaved in the acidic environment of an endosome (for example at pH below 6.0, preferably at pH below 5.5, or at pH below 5.0).

For example, amino acid sequences susceptible to cleavage by furin include sequences selected from
   i) $RX^1KR$ [SEQ ID NO: 2]; and
   ii) $RX^2RR$ [SEQ ID NO: 3];
in which $X^1$ and $X^2$, which may be the same or different, each represents any amino acid residue (Zimmer et al., *J. Biol. Chem.*, 2001, 276, 31642-31650; Nakayama, *Biochem. J.*, 1997, 327, 625-635)

Preferred amino acid residues $X^1$ include Lys (K) and Val (V), for example Lys (K). Preferred amino acid residues $X^2$ include Lys (K) and Val (V), for example Val (V). For example, the cathepsin enzyme may be any suitable cathepsin enzyme (see Pillay et al., *Biochem. J.*, 2002, 363, 417-429). For example, it may be cathepsin B. For example, amino acid sequences susceptible to cleavage by cathepsin B (see Pechar et al., *Macromol. Chem. Phys.*, 1997, 198, 1009-1020) include sequences selected from:
   iii) $X^3X^4$ where $X^3$ is selected from Tyrosine (Tyr, Y), Phenylalanine (Phe, F), Leucine (Leu, L), Valine (Val, V) and Isoleucine (Ile, I) and $X^4$ is selected from Glycine (Gly, G), Alanine (Ala, A) and Glutamic acid (Glu, E).

Preferably, $X^3$ is selected from Tyrosine (Tyr, Y), Phenylalanine (Phe, F) and Leucine (Leu, L).

For example, the sequence $X^3X^4$ may be present as $GFX^3X^4$ [SEQ ID NO: 4], for example as GFLG (as used in Pechar et al., *Bioconjugate Chem.*, 2000, 11, 131-139)

The spacer element peptide B may additionally comprise a linker, which is preferably either a peptide, that is to say, it comprises amino acid residues, or a polyethyleneglycol group, or a mixture of the two. The amino acids may be naturally occurring or non-naturally occurring. They may have L- or D-configuration. The linker may have two or more amino acids. It may, for example, comprise three or more amino acids, for example, four or more, for example, five or more, for example, up to ten amino acids or more. The amino acids may be the same or different, but the use of multiple lysine residues (or other cationic amino acids suitable for use in the polycationic nucleic acid-binding component of a vector complex) should generally be avoided in the spacer as oligo-lysine sequences have activity as a polycationic nucleic acid-binding component.

The linker may be, for example, the dipeptide glycine-glycine (GG) or glycine-alanine (GA).

The linker may be, or may include a polyethyleneglycol moiety. The polyethyleneglycol moiety may comprise from 1 to 30 ethylene glycol units, preferably from 1 to 15 units, more preferably from 1 to 8 units, for example from 2 to 6 units, for example 4 units.

Preferably, the linker is at the end of the spacer element peptide B which is bonded to the polycationic nucleic acid-binding component A.

Preferably the cell surface receptor binding component C comprises a peptide. Where cell surface receptor binding component C comprises a peptide, the peptide may be up to 20 amino acids in length, or may be longer. The peptide generally has at least 5 amino acids but may have fewer. Generally, the peptide has any number of amino acids from 6 to 20 inclusive. Generally, it is preferred for the peptide to have 15 amino acids or fewer, more preferably 12 amino acids or fewer, most preferably 10 amino acids or fewer. Generally, it is preferred for the peptide to have 5 or more amino acids, for example, 6 or more amino acids. Most preferably, the peptide has 7 amino acids.

Preferably the cell surface receptor binding component C comprises a peptide comprising a cyclic region. Cyclic peptides may be formed by the provision of at least two cysteine residues in the peptide, thus enabling the formation of a disulphide bond. Accordingly, preferred cell surface receptor binding components C consist of or comprise a peptide having two or more cysteine residues that are capable of forming one or more disulphide bond(s). Preferably the cysteine residues flank the primary receptor binding portion.

In one embodiment of the invention, the cell surface receptor binding component C comprises an integrin-binding peptide. An integrin-binding peptide is any peptide that is capable of binding specifically to integrins found on the surface of cells. The integrin-binding peptide may be a naturally occurring integrin-binding ligand, for example, an extracellular matrix protein, a viral capsid protein, the bacterial protein invasin, a snake venom disintegrin protein, or an integrin-binding fragment of any such protein. Such integrin-binding proteins and fragments thereof may be obtained from natural sources or by recombinant techniques. It is preferable to use integrin-binding peptides, in particular because of their ease of synthesis, purification and storage, their potential for chemical modification, and their potentially low immunogenicity in vivo. Preferred integrin-binding peptides are those such as described in WO 96/15811, and especially WO 98/54347. For example, an integrin-binding peptide may be specific for α4β1 integrins.

In this embodiment, the cell surface receptor binding component C preferably comprises a peptide selected from:
 a) RGD;
 b) RRETAWA [SEQ ID NO: 5];
 c) LDV In a further embodiment of the invention, the cell surface receptor binding component C comprises a peptide which is capable of binding to human airway epithelial (HAE) cells. Preferred HAE cell-binding peptides are those such as described in WO 02/072616.

In this embodiment, the cell surface receptor binding component C preferably comprises a peptide selected from
 a) $X^5$SM;
 b) $LX^6$HK [SEQ ID NO: 6];
 c) $PSGX^7$ARA [SEQ ID NO: 7];
 d) $SX^8$RSMNF [SEQ ID NO: 8]; and
 e) $LX^9$HKSMP [SEQ ID NO: 9];
in which $X^5$ is a basic amino acid residue, $X^6$ is Q or P, $X^7$ is A or T, $X^8$ is an acidic amino acid residue and $X^9$ is P or Q.

Preferably, the cell surface receptor binding component C comprises a peptide selected from a) $X^5$SM;
b) L$X^6$HK; and
c) PSGAARA [SEQ ID NO: 10], in which $X^5$ is a basic amino acid residue and $X^6$ is Q or P.

Preferably $X^5$ is K or R. Preferably $X^6$ is P. Preferably $X^7$ is A. Preferably $X^8$ is E or Q. More preferably $X^8$ is E. Preferably $X^9$ is P. Accordingly, preferred peptides are those comprising a sequence selected from LQHKSMP [SEQ ID NO: 11], LPHKSMP [SEQ ID NO: 12], VKSMVTH [SEQ ID NO: 13], SERSMNF [SEQ ID NO: 14], VGLPHKF [SEQ ID NO: 15], YGLPHKF [SEQ ID NO: 16], PSGAARA [SEQ ID NO: 10], SQRSMNF [SEQ ID NO: 17]; and PSGTARA [SEQ ID NO: 18].

In another embodiment of the invention, the cell surface receptor binding component C comprises a peptide which is capable of binding to human dendritic cells. Preferred human dendritic cell-binding peptides are those such as described in WO 2004/108938. For example, such a peptide may be selected from a peptide comprising an amino acid sequence selected from:

a) P$X^{10}X^{11}X^{12}$T [SEQ ID NO: 19];
b) PS$X^{13}$S [SEQ ID NO: 20];
c) Q$X^{14}X^{15}X^{16}$Q [SEQ ID NO: 21];
d) S$X^{17}$S, in which $X^{10}$, $X^{11}$ and $X^{12}$, which may be the same or different, each represents an amino acid residue;

$X^{13}$ represents an amino acid residue;

$X^{14}$ and $X^{16}$, which may be the same or different, each represents an amino acid residue, and $X^{15}$ represents an amino acid residue having an amide side chain, for example, N or Q.

$X^{17}$ represents an amino acid residue having an aliphatic side chain, for example, L or I.

In a preferred embodiment, the cell surface receptor binding component C comprises a peptide selected from:

a) CRGDCLG [SEQ ID NO: 22];
b) CRGDCLG [SEQ ID NO: 22];
c) ACDCRGDCFCG [SEQ ID NO: 23];
d) CRGDMFGCA [SEQ ID NO: 24];
e) CRRETAWACG [SEQ ID NO: 25];
f) CRGEMFGCA [SEQ ID NO: 26];
g) CSERSMNFCG [SEQ ID NO: 27];
h) CYGLPHKFCG [SEQ ID NO: 28]; and
i) CLPHKSMPCG [SEQ ID NO: 29].

The invention provides the use of a peptide derivative of the invention to target an entity to a cell, the entity being a nucleic acid or another molecule, for example, a therapeutically or pharmaceutically active molecule, or a molecule comprising a detectable label.

One of the limiting-steps for the gene transfer with synthetic vectors is the non-dissociation of complexes that will allow entry and transcription of DNA inside the nucleus (for reviews, see Wiethoff and Middaugh, Barriers to nonviral gene delivery. *J Pharm Sci.* 2003 February; 92(2):203-17; and Lechardeur et al., Intracellular routing of plasmid DNA during non-viral gene transfer. *Adv Drug Deliv Rev.* 2005 Apr. 5; 57(5):755-67). It is postulated (and the inventors are not bound by this theory), that cleavage of the peptide from the polycationic nucleic acid binding component leads to endosomal membrane destabilization (Wrobel and Collins, Fusion of cationic liposomes with mammalian cells occurs after endocytosis. *Biochim Biophys Acta.* 1995 May 4; 1235(2): 296-304) and increases the amount of plasmid DNA released into the cytoplasm (Hafez et al., On the mechanism whereby cationic lipids promote intracellular delivery of polynucleic acids. *Gene Ther.* 2001 August; 8(15):1188-96) and so, the transfection efficiency.

It has further been found that a cleavable peptide of the invention improves the targeting of a vector complex to tumour cells, particularly when used in conjunction with a cleavable lipid of the invention. The peptides of the invention thus find use in the treatment of cancers. The invention thus provides a method of treating cancer in a patient comprising administering a peptide of the invention in a suitable complex to the patient in an effective amount.

The present invention further provides a non-viral transfection complex that comprises (i) a nucleic acid, and
(ii) a peptide derivative of the invention.

The present invention further provides a non-viral transfection complex that comprises (i) a nucleic acid,
(ii) a peptide derivative of the invention, and
(iii) a lipid component.

The nucleic acid component may be any suitable nucleic acid. It may be DNA or RNA or a chemically modified nucleic acid mimetic, for example a PNA molecule. It may, for example, code for a protein that has a utility in the target cell. It may be an anti-sense nucleic acid or an RNAi nucleic acid.

RNAi is achieved by exposing the cellular messenger RNA (mRNA) molecules produced by the target gene to double-stranded RNA (dsRNA) molecules that contain sequences complementary to a short portion of the mRNA molecule. Inside the cell, the double-stranded RNA molecules are cleaved to produce short (21-23 nucleotides long) single and double-stranded fragments which can bind to the target mRNA molecules. Such binding leads to the cleavage of the target mRNA by nucleases, thus resulting in a reduction in the expression levels of the target gene.

Thus the nucleic acid component may itself be an RNAi molecule (an "siRNA"); alternatively, the nucleic acid administered may be a DNA molecule that comprises a sequence that, when transcribed, produces an RNAi molecule, ie an RNA that is capable of suppressing the expression of a target gene via RNA interference.

The invention also provides processes for the production of a transfection complex of the invention.

The invention further provides a pharmaceutical composition which comprises a transfection complex of the invention in admixture or conjunction with a pharmaceutically suitable carrier.

The invention further provides a method for the treatment or prophylaxis of a condition caused in a human or in a non-human animal by a defect and/or a deficiency in a gene which comprises administering a transfection complex of the invention the human or to the non-human animal.

The term "a defect and/or a deficiency in a gene" as used herein denotes not only a defect or deficiency in the coding region of a gene, but a defect or deficiency in a control element for the gene, for example, a control element in trans or in cis, or a defect or deficiency in any other element that is involved in the transcription or translation of the gene, whether directly or indirectly.

The invention further provides a method for therapeutic or prophylactic immunisation of a human or of a non-human animal, which comprises administering a transfection complex of the invention comprising an anti-sense nucleic acid (for example anti-sense RNA) or a nucleic acid suitable for RNAi therapy to the human or to the non-human animal.

The invention also provides a method of anti-sense therapy, which comprises administering a transfection complex of the invention to a human or to a non-human animal in which the nucleic acid is a nucleic acid (for example RNA) suitable for use in anti-sense therapy or a nucleic acid suitable for RNAi therapy.

The invention further provides a transfection complex of the invention for use as a medicament or a vaccine.

The invention also provides the use of a transfection complex of the invention for the manufacture of a medicament for the prophylaxis of a condition caused in a human or a non-human animal by a defect and/or a deficiency in a gene, or for therapeutic or prophylactic immunisation, or for anti-sense or RNAi therapy.

The invention additionally provides a kit that comprises:
(i) a nucleic acid, and
(ii) a peptide derivative of the invention.

The invention further provides a kit that comprises:
(i) nucleic acid,
(ii) a peptide derivative of the invention, and
(iii) a lipid component.

The present invention also provides a lipid derivative of general formula (I):

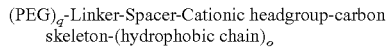
(PEG)$_q$-Linker-Spacer-Cationic headgroup-carbon skeleton-(hydrophobic chain)$_o$ wherein:
the Linker is a group susceptible to cleavage within a cell;
the Spacer is a group linking the Linker to the Cationic headgroup;
q denotes the number of PEG chains and q=1, 2 or 3;
o denotes the number of hydrophobic chains and o=1, 2 or 3;
the carbon skeleton is a group linking the hydrophobic chains to the cationic headgroup.

Susceptible to cleavage is understood herein to mean that the Linker is susceptible to cleavage over a timescale during which the other components remain intact. The Linker is cleaved more rapidly than the cellular lipid degradation pathways take effect.

In one aspect of the invention (L1), the lipid derivative of the invention is a lipid derivative of general formula (II):

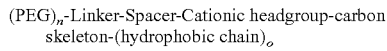
(PEG)$_n$-Linker-Spacer-Cationic headgroup-carbon skeleton-(hydrophobic chain)$_o$ wherein:
the Linker is an ester group or an acetal group;
the Spacer is a group linking the Linker to the Cationic headgroup;
n denotes the number of PEG chains, and n=1 if the linker is an ester group and n=2 if the linker is an acetal group;
o denotes the number of hydrophobic chains and o=1, 2 or 3;
the carbon skeleton is a group linking the hydrophobic chains to the cationic head group.

Preferably, each PEG chain is independently a group 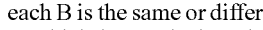—{B—O}$_m$—B-Q wherein
each B is the same or different and is a C$_{1-6}$ alkylene group which is unsubstituted or substituted by one or more substituents selected from hydroxy, halogen, —OR$^1$, —C(O)OH, —CN, —NR$^1$R$^2$, —C(O)OR$^1$, —OC(O)R$^1$ and —C(O)R$^1$;
R$^1$ and R$^2$ are the same or different and are C$_{1-4}$ hydrocarbyl;
m is an integer from 1 to 100; and
Q is selected from —N$^+$(R$^3$)$_3$, —OH, and —OR$^3$ wherein R$^3$ is an unsubstituted C$_{1-4}$ alkyl group or a trifluoromethyl group.

Preferably, m is from 1 to 50, for example from 2 to 20. More preferably m is from 1 to 10, especially from 1 to 8, for example from 1 to 6, more preferably m is from 1 to 3, such as 1 or 2.

Where the Linker is an acetal group, m is preferably from 1 to 8, for example from 1 to 6, more preferably m is from 1 to 3, such as 1 or 2, particularly 1.

Where the Linker is an ester group, m is preferably from 1 to 8, for example from 1 to 6, more preferably m is from 1 to 3, such as 2.

Lipid derivatives of general formula (II) wherein the Linker is an acetal group were found to have greater gene transfer efficiencies in various different cell types than equivalent non-cleavable lipid derivatives lacking the cleavable Linker group. Lipid derivatives of general formula (II) wherein the Linker is an ester group were found to have greater gene transfer efficiencies in various different cell types than equivalent non-cleavable lipid derivatives lacking the cleavable Linker group, or non-cleavable lipid derivatives lacking both the cleavable Linker group and the PEG chains.

Preferred acetal or ester linker groups are those which are susceptible to hydrolysis at pH 3.5 or above, more preferably at pH 4.0 or above, particularly at pH 4.5 or above, for example at pH 5.0 or above. Preferably, they are stable at pH 7.0 or above, more preferably 6.5 or above, particularly at pH 6.0 or above.

Where the linker is an acetal linker, there are two PEG chains, which may be the same or different, each of which is attached to the oxygen atoms of the acetal group.

Where the linker is an ester linker, the ester group may be arranged in either orientation—with the carbonyl group on the side of the spacer or with the oxygen atom on the side of the spacer.

The Spacer is a hydrocarbon chain comprising from 1 to 8 carbon atoms.

The Cationic headgroup may be any group having at least one positive charge. Preferred Cationic headgroups are those comprising a quaternary ammonium group.

The carbon skeleton is a group linking the hydrophobic chain(s) to the cationic headgroup and may comprise from 2 to 8 carbon atoms, preferably from 2 to 6 carbon atoms, especially from 2 to 4 carbon atoms, for example 3 carbon atoms, as well as one or more, for example one, two or three, moieties for attachment of the hydrophobic chain(s), for example one or more ether groups or ester groups.

There may be one, two or three hydrophobic chains, preferably two hydrophobic chains. Where there is more than one hydrophobic chain, the chains may be the same or different. Each hydrophobic chain is independently selected from a straight or branched, saturated or unsaturated $C_{7-24}$ hydrocarbyl group which is unsubstituted or substituted by one or more substituents selected from hydroxy, halogen and OR', wherein R' is a $C_{1-6}$ hydrocarbyl group.

In one embodiment of the L1 aspect of the invention, the invention provides a compound of formula (III):

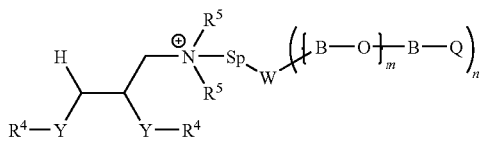

wherein:
  each Y is the same or different and is selected from —O—, and —O—C(O)—;
  each $R^4$ is the same or different and is selected from a straight or branched, saturated or unsaturated $C_{7-24}$ hydrocarbyl group which is unsubstituted or substituted by one or more substituents selected from hydroxy, halogen and OR', wherein R' is a $C_{1-6}$ hydrocarbyl group;
  each $R^5$ is the same or different and is selected from a straight or branched, saturated or unsaturated $C_{1-10}$ hydrocarbyl group which is unsubstituted or substituted by one or more substituents selected from hydroxy, halogen, —OR', —C(O)OH, —CN, —N(R')$_2$, and —C(O)R', wherein each R' is the same or different and is a $C_{1-6}$ hydrocarbyl group;
  Sp is a $C_{1-8}$ alkylene group which is unsubstituted or substituted by one or more substituents selected from hydroxy, halogen and OR', wherein R' is a $C_{1-6}$ hydrocarbyl group;
  W is selected from —O—C(O)—, —C(O)O—, and the group of formula (IV):

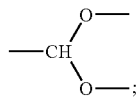 (IV)

n denotes the number of PEG chains, and n=1 if the linker W is —O—C(O)— or —C(O)O—, and n=2 if the linker W is the group of formula (IV);
each B is the same or different and is a $C_{1-6}$ alkylene group which is unsubstituted or substituted by one or more substituents selected from hydroxy, halogen, —OR$^1$, —C(O)OH, —CN, —NR$^1$R$^2$, —C(O)OR$^1$, —OC(O)R$^1$ and —C(O)R$^1$;
$R^1$ and $R^2$ are the same or different and are $C_{1-4}$ hydrocarbyl;
m is an integer from 1 to 100; and
Q is selected from —N$^+$(R$^3$)$_3$, —OH, and —OR$^3$ wherein $R^3$ is an unsubstituted $C_{1-4}$ alkyl group or a trifluoromethyl group.

In another aspect of the invention (L2), the lipid derivative of the invention is a lipid derivative of general formula (V):

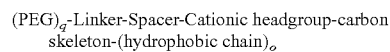

wherein:
  the Linker is a group susceptible to cleavage within a cell;
  the Spacer is a group linking the Linker to the Cationic headgroup;
  q denotes the number of PEG chains and q=1, 2 or 3;
  each PEG group is independently a group {B—O}$_p$—B-Q wherein
    each B is the same or different and is a $C_{1-6}$ alkylene group which is unsubstituted or substituted by one or more substituents selected from hydroxy, halogen, —OR$^1$, —C(O)OH, —CN, —NR$^1$R$^2$, C(O)OR$^1$, —OC(O)R$^1$ and —C(O)R$^1$;
    $R^1$ and $R^2$ are the same or different and are $C_{1-4}$ hydrocarbyl;
    p is an integer from 1 to 8; and
    Q is selected from —N$^+$(R$^3$)$_3$, —OH, and —OR$^3$ wherein $R^3$ is an unsubstituted $C_{1-4}$ alkyl group or a trifluoromethyl group;
  o denotes the number of hydrophobic chains and o=1, 2 or 3; and
  the carbon skeleton is a group linking the hydrophobic chains to the cationic headgroup.

Preferably, p is from 1 to 6, more preferably p is from 1 to 4, such as 1 or 2. Example lipid derivatives of general formula (V) wherein p=2 were found to have greater gene transfer efficiencies in various different cell types than equivalent lipid derivatives of general formula (V) wherein p=5, which suggests that having shorter PEG chain lengths improves gene transfer efficiency.

The Linker may be any group that is susceptible to cleavage within a cell. The Linker may be susceptible to cleavage within any part of a cell, for example within the endosome, lysosome, and/or cytoplasm of a cell. Preferably, the Linker is susceptible to enzymatic cleavage, reductive cleavage, or pH-dependent cleavage e.g. hydrolysis Preferably the Linker is an orthoester group, a vinyl ether group, an acyl hydrozone group, an ester group, an acetal group, or a disulfide group.

Preferred Linker groups are those which are susceptible to hydrolysis. Preferably, a Linker that is susceptible to hydrolysis hydrolyses at pH 3.5 or above, more preferably at pH 4.0 or above, particularly at pH 4.5 or above, for example at pH 5.0 or above. Preferably, such Linkers are stable at pH 7.0 or above, more preferably 6.5 or above, particularly at pH 6.0 or above.

Where the linker is an acetal linker, there are two polyethylene glycol components, which may be the same or different, each of which is attached to the oxygen atoms of the acetal group.

Where the linker is an ester linker, the ester group may be arranged in either orientation—with the carbonyl group on the side of the spacer or with the oxygen atom on the side of the spacer.

The Spacer is a hydrocarbon chain comprising from 1 to 8 carbon atoms.

The Cationic headgroup may be any group having at least one positive charge. Preferred Cationic headgroups are those comprising a quaternary ammonium group.

The carbon skeleton is a group linking the hydrophobic chain(s) to the cationic headgroup and may comprise from 2 to 8 carbon atoms, preferably from 2 to 6 carbon atoms, especially from 2 to 4 carbon atoms, for example 3 carbon atoms, as well as one or more, for example one, two or three, moieties for attachment of the hydrophobic chain(s), for example one or more ether groups or ester groups.

There may be one, two or three hydrophobic chains, preferably two hydrophobic chains. Where there is more than one hydrophobic chain, the chains may be the same or different. Each hydrophobic chain is independently selected from a straight or branched, saturated or unsaturated $C_{7-24}$ hydrocarbyl group which is unsubstituted or substituted by one or more substituents selected from hydroxy, halogen and OR', wherein R' is a $C_{1-6}$ hydrocarbyl group.

In one embodiment of the L2 aspect of the invention, the invention provides a compound of formula (VI):

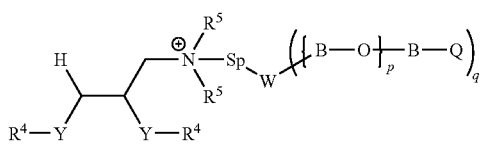

wherein:
each Y is the same or different and is selected from —O—, and —O—C(O)—;
each $R^4$ is the same or different and is selected from a straight or branched, saturated or unsaturated $C_{7-24}$ hydrocarbyl group which is unsubstituted or substituted by one or more substituents selected from hydroxy, halogen and OR', wherein R' is a $C_{1-6}$ hydrocarbyl group;
each $R^5$ is the same or different and is selected from a straight or branched, saturated or unsaturated $C_{1-10}$ hydrocarbyl group which is unsubstituted or substituted by one or more substituents selected from hydroxy, halogen, —OR', —C(O)OH, —CN, —N(R')$_2$, and —C(O)R', wherein each R' is the same or different and is a $C_{1-6}$ hydrocarbyl group;
Sp is a $C_{1-8}$ alkylene group which is unsubstituted or substituted by one or more substituents selected from hydroxy, halogen and OR', wherein R' is a $C_{1-6}$ hydrocarbyl group;
W is a group susceptible to cleavage within a cell;
q denotes the number of PEG chains;
each B is the same or different and is a $C_{1-6}$ alkylene group which is unsubstituted or substituted by one or more substituents selected from hydroxy, halogen, —OR$^1$, —C(O)OH, —CN, —NR$^1$R$^2$, —C(O)OR$^1$, —OC(O)R$^1$ and —C(O)R$^1$;
$R^1$ and $R^2$ are the same or different and are $C_{1-4}$ hydrocarbyl;
p is an integer from 1 to 8; and
Q is selected from —N$^+$(R$^3$)$_3$, —OH, and —OR$^3$ wherein $R^3$ is an unsubstituted $C_{1-4}$ alkyl group or a trifluoromethyl group.

In the above embodiment of the L2 aspect of the invention, W may be any group that is susceptible to cleavage within a cell. The Linker W may be susceptible to cleavage within any part of a cell, for example within the endosome, lysosome, and/or cytoplasm of a cell. Preferably, the Linker W is susceptible to enzymatic cleavage, reductive cleavage, or pH-dependent cleavage e.g. hydrolysis Preferably W is an orthoester group, a vinyl ether group, an acyl hydrozone group, an ester group, an acetal group, or a disulfide group.

Preferred W groups are those which are susceptible to hydrolysis. Preferably, a W group that is susceptible to hydrolysis hydrolyses at pH 3.5 or above, more preferably at pH 4.0 or above, particularly at pH 4.5 or above, for example at pH 5.0 or above. Preferably, such W groups are stable at pH 7.0 or above, more preferably 6.5 or above, particularly at pH 6.0 or above.

Where W is an acetal linker, there are two PEG chains, which may be the same or different, each of which is attached to the oxygen atoms of the acetal group.

Where W is an ester linker, the ester group may be arranged in either orientation—with the carbonyl group on the side of the spacer or with the oxygen atom on the side of the spacer.

As used herein, a $C_{1-4}$ alkyl group or moiety is a linear or branched alkyl group or moiety containing from 1 to 4 carbon atoms such as a $C_{1-2}$ alkyl group or moiety. Examples of $C_{1-4}$ alkyl groups and moieties include methyl, ethyl, n-propyl, i-propyl, n-butyl, i-butyl and t-butyl. For the avoidance of doubt, where two alkyl moieties are present in a group, the alkyl moieties may be the same or different.

As used herein, an alkylene group is a divalent alkyl group, wherein the alkyl group is as defined above. For example a $C_1$ alkylene group (i. e. methylene) is a divalent $C_1$ alkyl group, i.e. —CH$_2$—. Where the alkylene group comprises 2 or more carbon atoms, the group may be branched, e. g. an ethylene group may be —CH$_2$CH$_2$— or —CH(CH$_3$)—.

As used herein, a hydrocarbyl group includes alkyl groups as defined above, alkenyl groups and alkynyl groups. Accordingly, a $C_{1-4}$ hydrocarbyl group, for example, includes $C_{1-4}$ alkyl groups as defined above, $C_{2-4}$ alkenyl groups and $C_{2-4}$ alkynyl groups. A $C_{2-4}$ alkenyl group or moiety is a linear or branched alkenyl group or moiety containing from 2 to 4 carbon atoms. The alkenyl group may contain one or more carbon-carbon double bonds, for example, one or two double bonds, each of which may be cis or trans. Preferred alkenyl groups contain one double bond. Preferably the double bond or bonds are in the cis configuration. Likewise, a $C_{2-4}$ alkynyl group or moiety is a linear or branched alkynyl group or moiety containing from 2 to 4 carbon atoms. The alkynyl group may contain one or more carbon-carbon triple bonds, for example, one or two triple bonds, preferably one triple bond. For the avoidance of doubt, where two alkenyl or two alkynyl moieties are present in a group, the alkenyl or alkynyl moieties may be the same or different. Typically the alkenyl groups are unsubstituted. Preferred unsaturated hydrocarbyl groups are alkenyl groups which contain one or more, for example one or two, double bonds, each of which may be cis or trans.

The PEG group may be capped or uncapped. Uncapped PEG groups are those which have a terminal hydroxy group. Preferred capped PEG groups include those in which the terminal hydroxy group is converted to a methoxy, ethoxy, or trifluoromethoxy group. Where the linker is an acetal linker, the polyethylene glycol component is preferably capped. Where the linker is an ester linker, the polyethylene glycol component is preferably uncapped.

Preferred PEG groups are those wherein m is an integer from 1 to 6, more preferably m is an integer from 1 to 3, such as 1 or 2. Where the linker is an acetal linker, m is preferably 1. Where the linker is an ester linker, m is preferably 2.

Preferred PEG groups are those wherein B is a $C_{1-5}$ alkylene group which is unsubstituted or substituted by one or more substituents as defined above. More preferably, B a $C_{2-4}$ alkylene group which is unsubstituted or substituted by one or more substituents as defined above. Most preferably, B is ethylene which is unsubstituted or substituted by one or more substituents as defined above.

Typically, B is unsubstituted or carries one or two substituents. Preferred substituents for B are selected from hydroxy, halogen and $-OR^1$ wherein $R^1$ is a $C_{1-6}$ alkyl group. More preferably, B is unsubstituted.

Preferred PEG groups are those wherein Q is selected from —OH, and $-OR^3$ wherein $R^3$ is an unsubstituted $C_{1-2}$ alkyl group or a trifluoromethyl group. Where the linker is an acetal linker, Q is preferably —OH or —OMe, particularly —OMe. Where the linker is an ester linker, Q is preferably —OH.

In the compounds of formula (III) and (VI) above, each Y is typically the same. Preferably each Y is —O—.

Preferably, each $R^4$ is the same or different and is selected from a straight or branched, saturated or unsaturated $C_{10-22}$ hydrocarbyl group which is unsubstituted or substituted as defined above. More preferably, each $R^4$ is the same or different and is selected from a straight or branched, saturated or unsaturated $C_{12-20}$ hydrocarbyl group which is unsubstituted or substituted as defined above. More preferably still, each $R^4$ is the same or different and is selected from a straight or branched, saturated or unsaturated $C_{16-18}$ hydrocarbyl group which is unsubstituted or substituted as defined above.

Typically, each $R^4$ is straight. Typically, each $R^4$ is unsubstituted or carry one, two or three substituents. Preferred substituents for each $R^4$ group are those selected from hydroxy, halogen and OR', wherein R' is a $C_{1-4}$ alkyl group. Preferably, each $R^4$ is unsubstituted.

Most preferably, each $R^4$ is the same or different and represents a palmitic, stearic, oleic, linoleic or linolenic residue. In one aspect of this embodiment, it is preferred that the each group $-Y-R^4$ is derived from a fatty acid residue, for example each group $-Y-R^4$ may represent $-O-(CH_2)_8CH=CH(CH_2)_7CH_3$ or $-O-(CH_2)_{10}CH=CH(CH_2)_3CH_3$. Each $R^4$ may therefore preferably be a monounsaturated $C_{18}$ or $C_{16}$ group, e.g. $-(CH_2)_{10}CH=CH(CH_2)_3CH_3$. Typically, both $R^4$ groups are the same.

Preferably each $R^5$ is the same or different and is selected from a straight or branched, saturated or unsaturated $C_{1-6}$ hydrocarbyl group, for example a $C_{1-4}$ hydrocarbyl group, which are unsubstituted or substituted by one or more substituents as defined above. Each $R^5$ is typically unsubstituted or carries one or two substituents. Preferred $R^5$ substituents are selected from hydroxy and —OR' wherein R' is a $C_{1-6}$ alkyl group. More preferably, each $R^5$ is unsubstituted. Typically both $R^5$ groups are the same. Preferably, both $R^5$ groups are methyl.

Preferably, Sp is a $C_{2-8}$ alkylene group which is unsubstituted or substituted by one or more substituents as defined above. More preferably, Sp is a $C_{4-8}$ alkylene group which is unsubstituted or substituted by one or more substituents as defined above. Typically Sp is unsubstituted or carries one or two substituents. Preferred substituents are selected from hydroxy, halogen and OR', wherein R' is a $C_{1-4}$ alkyl group. More preferably, Sp is unsubstituted.

In a further aspect, the present invention provides a composition that comprises
(ii) a lipid derivative of the invention as defined above,
(iii) a polycationic nucleic acid-binding component, and
(iv) a cell surface receptor binding component.

In a further aspect, the present invention provides a composition that comprises
(ii) a lipid derivative of the invention as defined above,
(iii) a polycationic nucleic acid-binding component, and In a further aspect, the present invention provides a non-viral transfection complex that comprises
(i) a nucleic acid,
(ii) a lipid derivative of the invention as defined above,
(iii) a polycationic nucleic acid-binding component, and
(iv) a cell surface receptor binding component.

The invention additionally provides a kit that comprises:
(ii) a lipid derivative of the invention as defined above,
(iii) a polycationic nucleic acid-binding component, and
(iv) a cell surface receptor binding component.

The invention additionally provides a kit that comprises:
(ii) a lipid derivative of the invention as defined above, and
(iii) a polycationic nucleic acid-binding component, The invention further provides a kit that comprises:
(i) a nucleic acid,
(ii) a lipid derivative of the invention as defined above,
(iii) a polycationic nucleic acid-binding component, and
(iv) a cell surface receptor binding component.

The polycationic nucleic acid-binding component is any polycation that is capable of binding to DNA or RNA. A polycation may be polycationic itself or it may have any number of cationic monomers provided the ability to bind to DNA or RNA is retained. For example, from 3 to 100 cationic monomers may be present, for example, from 10 to 20, for example from 14 to 18, for example, about 16.

An example of a nucleic acid-binding polycationic molecule is an oligopeptide comprising one or more cationic amino acids. Such an oligopeptide may, for example, be an oligo-lysine molecule, an oligo-histidine molecule, an oligo-arginine molecule, an oligo-ornithine molecule, an oligo diaminopropionic acid molecule, or an oligo-diaminobutyric acid molecule, or a combined oligomer comprising any combination of histidine, arginine, lysine, ornithine diaminopropionic acid, and diaminobutyric acid residues. Any of the above oligopeptides may have, for example, a total of from 3 to 35, for example, from 5 to 25 residues, preferably from 10 to 20 residues, for example, from 14 to 18 residues, for example 16 residues.

An oligolysine is particularly preferred, for example, having from 3 to 35, for example, from 2 to 25, for example, form 10 to 20 lysine residues, for example, from 13 to 19, for example, from 14 to 18, for example, from 15 to 17 residues, for example, 16 residues i.e. $[K]_{16}$, "K" denoting lysine.

Further examples of polycationic components include dendrimers and polyethylenimine. Polyethylenimine (PEI) is a non-toxic, cross-linked cationic polymer with gene delivery potential (*Proc. Natl. Acad. Sci.*, 1995, 92, 7297-7301). Polyethylenimine is obtainable from Fluka (800 kDa) or from Sigma (50 kDa) or alternatively pre-diluted for transfection purposes from PolyPlus-tranfection (Illkirch, France). Typically, PEI is most efficient when used in a 9 fold excess over DNA, the excess ratio being calculated as PEI nitrogen:DNA phosphate, and at pH 5 to 8. Such parameters may be optimised in a manner familiar to the person skilled in the art.

Preferably the cell surface receptor binding component comprises a peptide. Where cell surface receptor binding component comprises a peptide, the peptide may be up to 20 amino acids in length, or may be longer. The peptide generally has at least 5 amino acids but may have fewer. Generally, the peptide has any number of amino acids from 6 to 20 inclusive. Generally, it is preferred for the peptide to have 15 amino acids or fewer, more preferably 12 amino acids or fewer, most preferably 10 amino acids or fewer. Generally, it is preferred for the peptide to have 5 or more amino acids, for example, 6 or more amino acids. Most preferably, the peptide has 7 amino acids. Preferably the cell surface receptor binding component comprises a peptide comprising a cyclic region. Cyclic peptides may be formed by the provision of at least two cysteine residues in the peptide, thus enabling the formation of a disulphide bond. Accordingly, preferred cell surface receptor binding components consist of or comprise a peptide having two or more cysteine residues that are capable of forming one or more disulphide bond(s). Preferably the cysteine residues flank the primary receptor binding portion.

In one embodiment of the invention, the cell surface receptor binding component comprises an integrin-binding peptide. An integrin-binding peptide is any peptide that is capable of binding specifically to integrins found on the surface of cells. The integrin-binding peptide may be a naturally occurring integrin-binding ligand, for example, an extracellular matrix protein, a viral capsid protein, the bacterial protein invasin, a snake venom disintegrin protein, or an integrin-binding fragment of any such protein. Such integrin-binding proteins and fragments thereof may be obtained from natural sources or by recombinant techniques. It is preferable to use integrin-binding peptides, in particular because of their ease of synthesis, purification and storage, their potential for chemical modification, and their potentially low immunogenicity in vivo. Preferred integrin-binding peptides are those such as described in WO 96/15811, and especially WO 98/54347. For example, an integrin-binding peptide may be specific for α4β1 integrins.

In this embodiment, the cell surface receptor binding component preferably comprises a peptide selected from:
  a) RGD;
  b) RRETAWA;
  c) LDV In a further embodiment of the invention, the cell surface receptor binding component comprises a peptide which is capable of binding to human airway epithelial (HAE) cells. Preferred HAE cell-binding peptides are those such as described in WO 02/072616.

In this embodiment, the cell surface receptor binding component preferably comprises a peptide selected from
  a) $X^5$SM;
  b) L$X^6$HK;
  c) PSG$X^7$ARA;
  d) S$X^8$RSMNF; and
  e) L$X^9$HKSMP;
in which $X^5$ is a basic amino acid residue, $X^6$ is Q or P, $X^7$ is A or T, $X^8$ is an acidic amino acid residue and $X^9$ is P or Q.

Preferably, the cell surface receptor binding component comprises a peptide selected from a) $X^5$SM;
b) L$X^6$HK; and
c) PSGAARA, in which $X^5$ is a basic amino acid residue and $X^6$ is Q or P.

Preferably $X^5$ is K or R. Preferably $X^6$ is P. Preferably $X^7$ is A. Preferably $X^8$ is E or Q. More preferably $X^8$ is E. Preferably $X^9$ is P. Accordingly, preferred peptides are those comprising a sequence selected from LQHKSMP, LPHKSMP, VKSMVTH, SERSMNF, VGLPHKF, YGLPHKF, PSGAARA, SQRSMNF and PSGTARA.

In another embodiment of the invention, the cell surface receptor binding component comprises a peptide which is capable of binding to human dendritic cells. Preferred human dendritic cell-binding peptides are those such as described in WO 2004/108938. For example, such a peptide may be selected from a peptide comprising an amino acid sequence selected from:

a) P$X^{10}X^{11}X^{12}$T;
b) PS$X^{13}$S;
c) Q$X^{14}X^{15}X^{16}$Q;
d) S$X^{17}$S, in which $X^{10}$, $X^{11}$ and $X^{12}$, which may be the same or different, each represents an amino acid residue;

$X^{13}$ represents an amino acid residue;

$X^{14}$ and $X^{16}$, which may be the same or different, each represents an amino acid residue, and $X^{15}$ represents an amino acid residue having an amide side chain, for example, N or Q. $X^{17}$ represents an amino acid residue having an aliphatic side chain, for example, L or I.

In a preferred embodiment, the cell surface receptor binding component comprises a peptide selected from:

a) CRGDCLG;
b) CRGDCLG;
c) ACDCRGDCFCG;
d) CRGDMFGCA;
e) CRRETAWACG;
f) CRGEMFGCA;
g) CSERSMNFCG;
h) CYGLPHKFCG; and
i) CLPHKSMPCG.

In a preferred aspect of the invention, components (iii) and (iv) of the above transfection complex are in the form of a peptide derivative of the invention.

Accordingly, in a particularly preferred aspect, the present invention provides a non-viral transfection complex that comprises (i) a nucleic acid,
(ii) a lipid derivative of the invention as defined above, and
(iii) a peptide derivative of the invention as defined above.

The nucleic acid component may be any suitable nucleic acid. It may be DNA or RNA or a chemically modified nucleic acid mimetic, for example a PNA molecule. It may, for example, code for a protein that has a utility in the target cell. It may be an anti-sense nucleic acid or an RNAi nucleic acid.

RNAi is achieved by exposing the cellular messenger RNA (mRNA) molecules produced by the target gene to double-stranded RNA (dsRNA) molecules that contain sequences complementary to a short portion of the mRNA molecule. Inside the cell, the double-stranded RNA molecules are cleaved to produce short (21-23 nucleotides long) single and double-stranded fragments which can bind to the target mRNA molecules. Such binding leads to the cleavage of the target mRNA by nucleases, thus resulting in a reduction in the expression levels of the target gene.

Thus the nucleic acid component may itself be an RNAi molecule; alternatively, the nucleic acid administered may be a DNA molecule that comprises a sequence that, when transcribed, produces an RNAi molecule, ie an RNA that is capable of suppressing the expression of a target gene via RNA interference.

The invention also provides processes for the production of a transfection complex of the invention.

The invention further provides a pharmaceutical composition which comprises a transfection complex of the invention in admixture or conjunction with a pharmaceutically suitable carrier.

The invention further provides a method for the treatment or prophylaxis of a condition caused in a human or in a non-human animal by a defect and/or a deficiency in a gene which comprises administering a transfection complex of the invention the human or to the non-human animal.

The term "a defect and/or a deficiency in a gene" as used herein denotes not only a defect or deficiency in the coding region of a gene, but a defect or deficiency in a control element for the gene, for example, a control element in trans or in cis, or a defect or deficiency in any other element that is involved in the transcription or translation of the gene, whether directly or indirectly.

The invention further provides a method for therapeutic or prophylactic immunisation of a human or of a non-human animal, which comprises administering a transfection complex of the invention comprising an anti-sense nucleic acid (for example anti-sense RNA) or a nucleic acid suitable for RNAi therapy to the human or to the non-human animal.

The invention also provides a method of anti-sense therapy, which comprises administering a transfection complex of the invention to a human or to a non-human animal in which the nucleic acid is a nucleic acid (for example RNA) suitable for use in anti-sense therapy or a nucleic acid suitable for RNAi therapy.

The invention further provides a transfection complex of the invention for use as a medicament or a vaccine.

The invention also provides the use of a transfection complex of the invention for the manufacture of a medicament for the prophylaxis of a condition caused in a human or a non-human animal by a defect and/or a deficiency in a gene, or for therapeutic or prophylactic immunisation, or for anti-sense or RNAi therapy.

One of the limiting-steps for the gene transfer with synthetic vectors is the non-dissociation of complexes that will allow entry and transcription of DNA inside the nucleus (for reviews, see Wiethoff and Middaugh, Barriers to nonviral gene delivery. *J Pharm Sci.* 2003 February; 92(2):203-17; and Lechardeur et al., Intracellular routing of plasmid DNA during non-viral gene transfer. *Adv Drug Deliv Rev.* 2005 Apr. 5; 57(5):755-67). It is postulated (and the inventors are not bound by this theory), that cleavage of the lipid from the PEG component leads to endosomal membrane destabilization (Wrobel and Collins, Fusion of cationic liposomes with mammalian cells occurs after endocytosis. *Biochim Biophys Acta.* 1995 May 4; 1235(2):296-304) and increases the amount of plasmid DNA released into the cytoplasm (Hafez et al., On the mechanism whereby cationic lipids promote intracellular delivery of polynucleic acids. *Gene Ther.* 2001 August; 8(15): 1188-96) and so, the transfection efficiency.

EXAMPLES

I—Peptide Synthesis

The peptides described (Table IA) were synthesised using standard instruments and techniques.

ME27, ME28, ME29, ME61, ME68, FMM8, FMM7, ME69, FMM12 were synthesised on a SYRO automated peptide synthesiser.

Linear Peptide Sequences:

The peptides were synthesised on a 20 µmol scale using 2 ml syringes with Teflon frits and 500 µl coupling volume. Fmoc-Gly preloaded NovaSyn TGT resin or Fmoc-Gly-2-Cl-Trt-resin were used for these sequences. Standard Fmoc-protected amino acids were used (Novabiochem), except for Fmoc-Peg4-COOH (used in ME28 and ME29), which was synthesised following a procedure reported previously (see synthesis of Fmoc-Haa4-COOH at page 82 of WO 2005/117985—Fmoc-Haa4-COOH was the name given to Fmoc-Peg4-COOH in that specification). The TGT resin was initially swelled for 10 min, however the 2-Cl-Trt resin needed a prolonged initial swelling time (some hours) in DMF. Routine coupling was performed with HBTU (in DMF) and DIPEA (in NMP) using a fourfold excess of reagents. Fmoc was cleaved with a 40% solution of piperidine in DMF for 3 min and a 20% solution for 10 min. Synthesis cycles consisted of 40 min coupling time, 3 min for Fmoc deprotection with 40% piperidine, another 10 min for Fmoc deprotection with 20% piperidine and washing steps. After synthesis and the last wash cycle with DMF, peptides were washed with DCM, methanol and diethyl ether (3 times each) using the "manual"/"empty" function of the Syro. Suction was applied for some more time to help evaporate the ether.

On-Resin Disulfide Bond Formation:

To form disulphide bridges on resin, the resin was placed in a syringe with PE frit and swelled in DMF. After removal of excess DMF a freshly prepared solution of iodine in a minimum amount of DMF (e.g. 500 µl for a 2 ml syringe, 10 eq iodine to resin loading) was added and the syringe was vortexed during 4 h for 20 s every 4 min. The reagent solution was removed and the resin was washed 10 to 20 times with DMF, and 3 times each with DCM, methanol and ether.

Cleavage and Deprotection:

The syringes were transferred to the fume hood for cleavage. Cleavage was performed with a cocktail of 95% TFA, 2.5% TIS and 2.5% $H_2O$. A minimum amount of freshly prepared cocktail was added to cover the resin (e.g. <500 µl in the 2 ml syringes). After 4 h the cleavage solutions were passed into PP tubes using a plunger and the resins were washed with another small amount of cleavage cocktail (e.g. 200 µl in the 2 ml syringes). Then the peptides were precipitated with ether (e.g. to the combined fractions of the 2 ml syringes some 4 ml of diethyl ether were added). The PP tubes were kept in the freezer for at least 15 min, then centrifuged at 3000 rpm for 3 min and solution was decanted from the peptide pellet. Centrifugation and decantation were repeated twice with about 2 ml of ether. Finally the peptides were dissolved in water or tBuOH/water (4:1) and freeze-dried. Some peptide sequences showed very poor solubility and sometimes several lyophilisation/dissolution processes with different solvent mixtures (water, tBuOH or acetonitrile) were necessary to obtain a fluffy peptide.

The peptides were analysed by reverse phase HPLC and purified where necessary by reverse phase HPLC to >90% pure. Mass spectra were recorded using the Micromass Quattro ES-MS (Software: Masslynx) and the masses are recorded in the table IB.

FMM5 was also synthesised on a SYRO automated peptide synthesiser.

Linear Peptide Sequence:

The peptide was synthesised on a 20 µmol scale using 2 ml syringes with Teflon frits and 500 µl coupling volume. Standard side-chain protecting groups were used for all amino acids; for $Cys^{24}$ and $Cys^{32}$ Acm was used; for $Cys^{26}$ and $Cys^{30}$ Trt was used. Fmoc-Gly preloaded NovaSyn TGT resin was used. The TGT resin was initially swelled for 10 min. Routine coupling was performed with HBTU (in DMF) and DIPEA (in NMP) using a fourfold excess of reagents. The Fmoc group was cleaved with a 40% solution of piperidine in DMF for 3 min and a 20% solution for 10 min. Synthesis cycles consisted of 40 min coupling time, 3 min for Fmoc deprotection with 40% piperidine, another 10 min for Fmoc deprotection with 20% piperidine and washing steps. After synthesis and the last wash cycle with DMF, peptides were washed with DCM, methanol and diethyl ether (3 times each) using the "manual"/"empty" function of the Syro. Suction was applied for some more time to help evaporate the ether.

Aerial Oxidation:

The peptide was dissolved in degassed water to make a final concentration of ~0.25 mg/ml. The solution was left to stir at room temperature exposed to the atmosphere for one week. After one week the reaction was concentrated in vacuo, the remaining residue was re-dissolved in degassed water and freeze-dried. This resulted in the formation of the disulfide bond between $Cys^{26}$ and $Cys^{30}$.

Formation of Second Disulfide Bridge:

The peptide and diphenyl sulfoxide were dissolved in TFA and anisole under Ar at 0° C. Trichloromethylsilane was then added, the reaction was purged with Ar and stirred for 3 h, allowing it to warm to room temperature. The peptide was then transferred to centrifuge tubes and precipitated with ether. The PP tubes were kept in the freezer for at least 15 min, then centrifuged at 3000 rpm for 3 min and solution was decanted from the peptide pellet. Centrifugation and decantation were repeated twice with about 2 ml of ether. Finally the peptides were dissolved in water or tBuOH/water (4:1) and freeze-dried. The peptide was purified by RP HPLC. The mass was recorded using the Micromass Quattro ES-MS (Software: Masslynx) and the mass is recorded in the table IB.

PCY, Peptide Y were purchased from Alta Biosciences (www.Altabioscience.bham.ac.uk) and synthesised using standard automated peptide synthesis techniques. The peptides were analysed by reverse phase HPLC and purified where necessary by reverse phase HPLC to 96% (PCY) and 85% (Peptide Y) pure. Relative molecular masses are given in the table IB.

K16, Peptide 1, Peptide 6, Peptide 11, Peptide E were purchased as described previously (Hart et al., Integrin-mediated transfection with peptides containing arginine-glycine-aspartic acid domains, *Gene Ther.* 1997 November; 4(11):1225-30 for peptide 1; Hart et al., Lipid-mediated enhancement of transfection by a nonviral integrin-targeting vector. *Hum Gene Ther.*, 1998, 9, 575-585 for peptide 6 and K16; Uduehi et al., Enhancement of integrin-mediated transfection of haematopoietic cells with a synthetic vector system, *Biotechnol. Appl. Biochem.*, 2003, 38, 201-209 for peptide 11; Writer et al., Targeted gene delivery to human airway epithelial cells with synthetic vectors incorporating novel targeting peptides selected by phage display, *J. Drug Target.*, 2004, 12, 185-193 for peptide E). Relative molecular masses are given in the table IB.

All these freeze-dried peptides were diluted at 10 mg/ml in water and stored at −20° C. during several months. Once thawing, aliquots of peptides are kept at 4° C. during several weeks. Repeated freeze-thawing cycles should be avoided as they lead to peptide degradation.

TABLE 1A

Peptide sequence

| Peptide | Sequence | Control | Sequence |
|---|---|---|---|
|  |  | K16 [SEQ ID NO: 1] | KKKKKKKKKKKKKKKK |
| ME27 [SEQ ID NO: 30] | $(K)_{16}$RVRRGACRGDCLG | ME61 [SEQ ID NO: 31] | $(K)_{17}$VRARGACRGDCLG |
|  |  | FMM12 [SEQ ID NO: 32] | $(K)_{16}$KVKKGACRGDCLG |
| ME28 [SEQ ID NO: 33] | $(K)_{16}$-Peg$_4$-RVRRGACRGDCLG |  |  |
| ME29 [SEQ ID NO: 34] | $(K)_{16}$RVRR-Peg$_4$-GACRGDCLG |  |  |
| FMM5 [SEQ ID NO: 35] | $(K)_{16}$RVRRGAACDCRGDCFCG |  |  |
| ME68 [SEQ ID NO: 36] | $(K)_{16}$RVRRGACRGDMFGCA | Peptide 1 [SEQ ID NO: 41] | $(K)_{16}$GACRGDMFGCA |
| FMM8 [SEQ ID NO: 37] | $(K)_{16}$RVRRGACRRETAWACG | Peptide 6 [SEQ ID NO: 42] | $(K)_{16}$GACRRETAWACG |
| FMM7 [SEQ ID NO: 38] | $(K)_{16}$RVRRGACRGEMFGCA | Peptide 11 [SEQ ID NO: 43] | $(K)_{16}$GACRGEMFGCA |
| ME69 [SEQ ID NO: 39] | $(K)_{16}$RVRRGACSERSMNFCG | Peptide E [SEQ ID NO: 44] | $(K)_{16}$GACSERSMNFCG |
| PCY [SEQ ID NO: 40] | $(K)_{16}$RVRRGACYGLPHKFCG | Peptide Y [SEQ ID NO: 45] | $(K)_{16}$GACYGLPHKFCG |

TABLE IB

| Peptide | Mass (g · mol$^{-1}$) | Peptide | Mass (g · mol$^{-1}$) |
|---|---|---|---|
| ME27 | 3467.5 | K16 | 2068 |
| ME28 | 3656.7 | ME61 | 3510.5 |
| ME29 | 3656.7 | FMM12 | 3383.4 |
| FMM5 | 3891.9 | Peptide 1 | 3124.5 |
| ME68 | 3703.8 | Peptide 6 | 3331.5 |
| FMM8 | 3879.9 | Peptide 11 | 3151.3 |
| FMM7 | 3717.8 | Peptide E | 3310.2 |
| ME69 | 3877.9 | Peptide Y | 3326.8 |
| PCY | 3873.6 | | |

II—PEG-Ester Lipid Synthesis

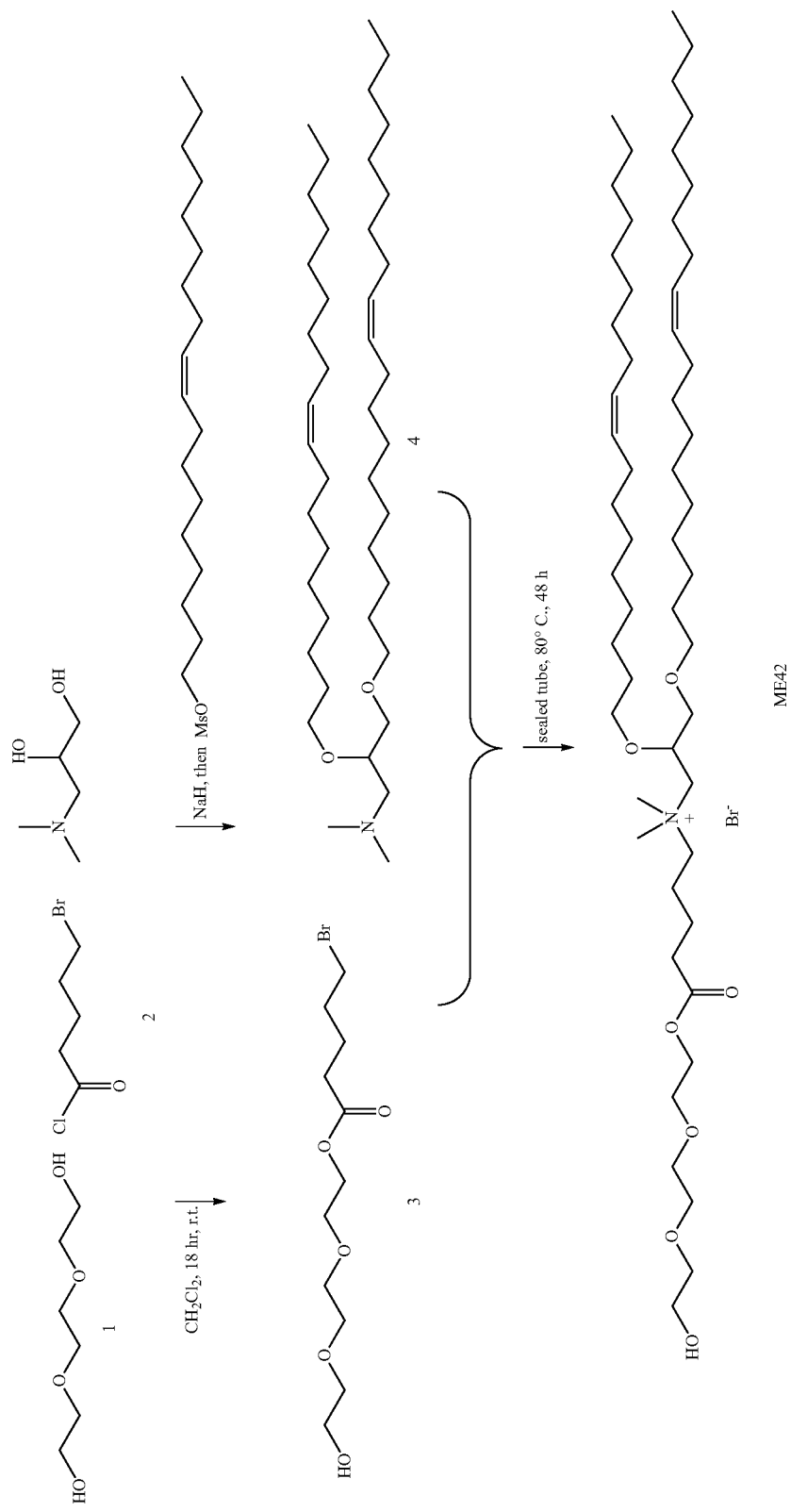

5-Bromopentanoic acid 8-hydroxy-3,6-dioxooctyl ester 3

Triethyleneglycol 1 (2.25 ml, 15 mmol) was stirred in dichloromethane (10 ml) for 10 min at RT. 5-Bromopentanoyl chloride 2 (670 μl, 5 mmol) was added dropwise and stirring was continued for 18 h. The mixture was concentrated in vacuo. Purification by flash chromatography on silica (5% methanol in dichloromethane) gave the titled product 3 as a yellowish oil (900 mg, 58%).

$\delta_H$ (300 MHz; CDCl$_3$) 1.68 (2H, m, COCH$_2$CH$_2$), 1.80 (2H, m, CH$_2$CH$_2$Br), 2.28 (2H, t, J 7.2 Hz, COCH$_2$), 3.31 (2H, t, J 6.5 Hz, CH$_2$Br), 3.47-3.62 (10H, m), 4.14 (2H, t, J 4.7 Hz, CH$_2$OCO);

$\delta_C$ (75 MHz; CDCl$_3$) 23.35 (COCH$_2$CH$_2$), 31.86 (CH$_2$CH$_2$Br), 33.03 (CH$_2$Br), 33.07 (COCH$_2$), 61.51 (HOCH$_2$), 63.32 (CH$_2$OCO), 69.01 (CH$_2$CH$_2$OCO), 70.20 (HOCH$_2$CH$_2$OCH$_2$), 70.44 (CH$_2$OCH$_2$CH$_2$OCO), 72.50 (HOCH$_2$CH$_2$), 173.05 (C=O);

m/z (ES+) 335.04651 ([M+Na]$^+$).

(2,3-Bis-octadec-9-enyloxypropyl)-(8-hydroxy-3,6-dioxooctyloxycarbonylbutyl)-dimethylammonium bromide (ME42)

A mixture of (2,3-bis-octadec-9-enyloxypropyl)-dimethylamine 4 (378 mg, 0.61 mmol) (synthesised from octadec-9-enyl mesylate and 3-dimethylamino-1,2-propanediol as described previously by Hurley et al., *J. Org. Chem.*, 2004, 69, 980-984) and 3 (335 mg, 1.07 mmol) in acetone (5 ml) was stirred in a sealed-tube at 80° C. for 48 h. After cooling, the solvent was evaporated in vacuo. Purification by flash chromatography on silica (gradient; 5% to 10% methanol in dichloromethane) gave ME42 as an orange oil (140 mg, 27%).

$\delta_H$ (300 MHz; CDCl$_3$) 0.89 (6H, t, J 6.7 Hz, 2×CH$_2$CH$_3$), 1.25 (44H, m), 1.53 (4H, m, 2×OCH$_2$CH$_2$CH$_2$), 1.72 (2H, m, COCH$_2$CH$_2$), 1.85 (2H, m, CH$_2$CH$_2$N$^+$), 1.99 (8H, m, 2×CH$_2$CH=CHCH$_2$), 2.45 (2H, t, J 6.8 Hz, COCH$_2$), 3.36-3.43 (11H, m, 2×CH$_3$N$^+$, CHOCH$_2$, CHCH$_2$OCH$_2$, 1H of N$^+$CH$_2$CH), 3.54-3.72 (14H, m, 8×CH$_2$CH$_2$O, HOCH$_2$, CH$_2$NCH$_2$CH, CHCH$_2$OCH$_2$), 3.88 (1H, d, J 13.2 N$^+$CH$_2$CH), 4.06 (1H, m, CH), 4.23 (2H, t, J 4.6 Hz, CH$_2$OCO), 5.32 (4H, m, 2×CH=CH); $\delta_C$ (75 MHz; CDCl$_3$) 14.10 (2×CH$_2$CH$_3$, overlap), 21.52 (COCH$_2$CH$_2$), 22.06 (CH$_2$CH$_2$N$^+$), 22.66, 26.03, 26.22, 27.20, 29.14-30.17 (signal overlap), 32.59, 33.20 (COCH$_2$), 52.25 (2×CH$_3$N$^+$, overlap), 61.39 (HOCH$_2$), 63.44 (CH$_2$OCO), 65.14 (N$^+$CH$_2$CH) 65.73 (CH$_2$CH$_2$N$^+$), 68.44 (CHCH$_2$O), 68.96 (CH$_2$CH$_2$OCO), 69.28 (CHOCH$_2$), 70.16 (HOCH$_2$CH$_2$OCH$_2$), 70.49 (CH$_2$OCH$_2$CH$_2$OCO), 71.99 (CHCH$_2$OCH$_2$), 72.50 (HOCH$_2$CH$_2$), 73.31 (CH), 129.72 (2×CH=CH, overlap), 129.95 (2×CH=CH, overlap) 172.74 (C=O);

m/z (ES+) 852.76483 (M$^+$).

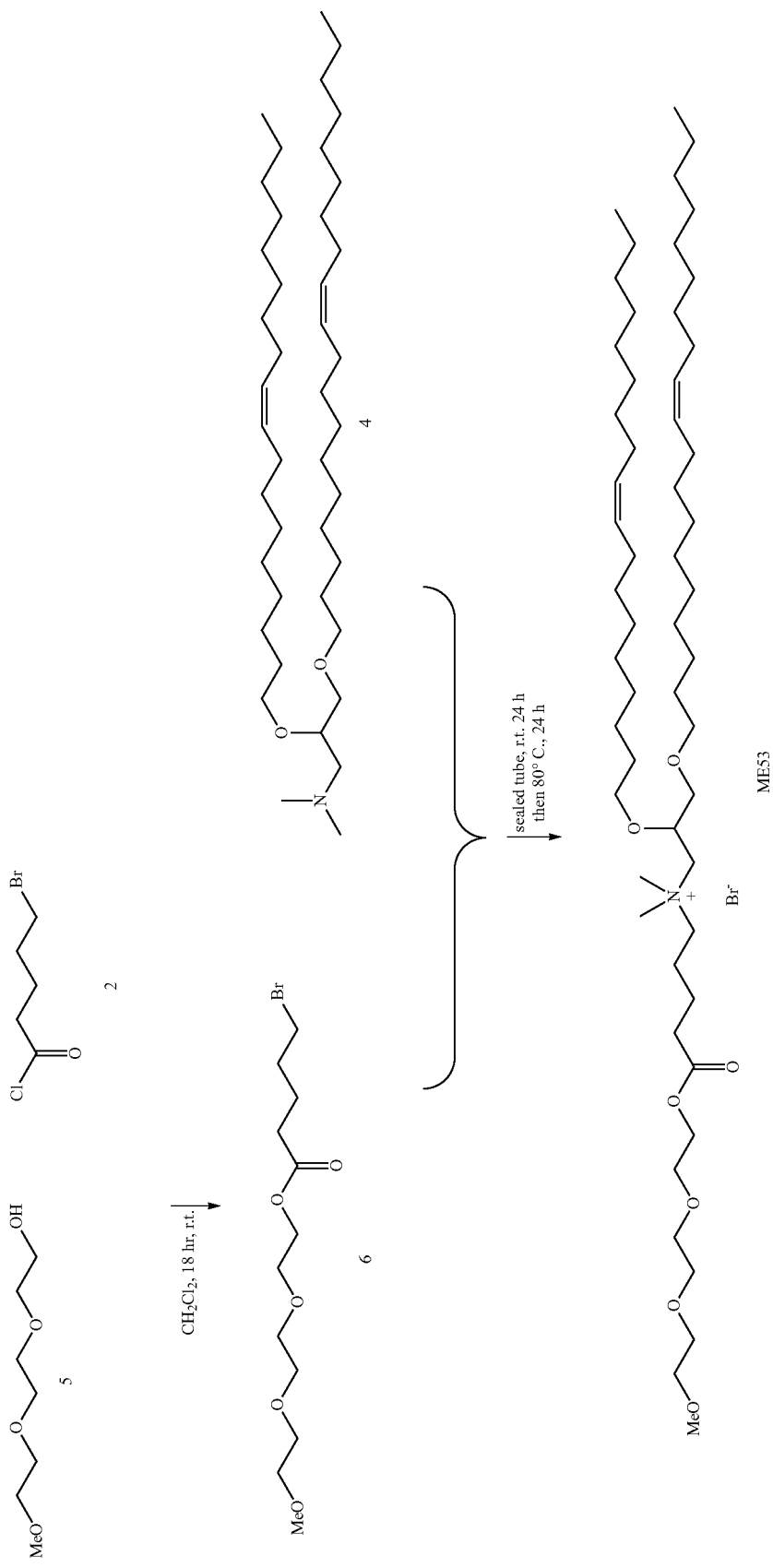

5-Bromopentanoic acid 3,6,9-trioxodecyl ester 6

Triethyleneglycol monomethylether 5 (880 µl, 5.5 mmol) was stirred in dichloromethane (10 ml) for 10 min at RT. 5-Bromopentanoyl chloride 2 (670 µl, 5 mmol) was added dropwise and stirring was continued for 18 h. The mixture was concentrated in vacuo. The product was purified by flash chromatography on silica (gradient; 2% to 7% methanol in dichloromethane) to obtain the titled product 6 as a yellowish oil (805 mg, 51%).

$\delta_H$ (300 MHz; CDCl$_3$) 1.70 (2H, m, COCH$_2$CH$_2$), 1.81 (2H, m, CH$_2$CH$_2$Br), 2.30 (2H, t, J 7.2 Hz, COCH$_2$), 3.30 (3H, s, CH$_3$O), 3.33 (2H, t, J 6.5 Hz, CH$_2$Br), 3.45-3.64 (10H, m), 4.15 (2H, t, J 4.7 Hz, CH$_2$OCO);

$\delta_C$ (75 MHz; CDCl$_3$) 23.38 (COCH$_2$CH$_2$), 31.87 (CH$_2$CH$_2$Br), 33.04 (CH$_2$Br), 33.06 (COCH$_2$), 58.97 (CH$_3$O), 63.47 (CH$_2$OCO), 69.05 (CH$_2$CH$_2$OCO), 70.49 (signal overlap), 70.54, 71.86 (CH$_3$OCH$_2$), 172.98 (C=O);

m/z (ES+) 349.06202 ([M+Na]$^+$).

(2,3-Bis-octadec-9-enyloxypropyl)-(3,6,9-trioxodecyloxycarbonylbutyl)-dimethylammonium bromide (ME53)

A mixture of 4 (430 mg, 0.69 mmol) and 6 (252 mg, 0.8 mmol) in acetone (5 ml) was stirred in a sealed-tube at RT for 24 h and than at 80° C. for another 24 h. After cooling, the solvent was evaporated in vacuo. Purification by flash chromatography on silica (10% methanol in dichloromethane) gave ME53 as an orange oil (264 mg, 44%).

$\delta_H$ (300 MHz; CDCl$_3$) 0.85 (6H, t, J 6.7 Hz, 2×CH$_2$CH$_3$), 1.24 (44H, m), 1.53 (4H, m, 2×OCH$_2$CH$_2$CH$_2$), 1.69 (2H, m, COCH$_2$CH$_2$), 1.84 (2H, m, CH$_2$CH$_2$N$^+$), 1.99 (8H, m, 2×CH$_2$CH=CHCH$_2$), 2.44 (2H, t, J 6.8 Hz, COCH$_2$), 3.34-3.45 (14H, m, 2×CH$_3$N$^+$, CH$_3$O, CHOCH$_2$, CHCH$_2$OCH$_2$, 1H of N$^+$CH$_2$CH), 3.54-3.72 (14H, m, 8×CH$_2$CH$_2$O, CH$_3$OCH$_2$, CH$_2$NCH$_2$CH, CHCH$_2$OCH$_2$), 3.88 (1H, d, J 13.6 N$^+$CH$_2$CH), 4.05 (1H, m, CH), 4.21 (2H, t, J 4.7 Hz, CH$_2$OCO), 5.32 (4H, m, 2×CH=CH);

$\delta_C$ (75 MHz; CDCl$_3$) 14.07 (2×CH$_2$CH$_3$, overlap), 21.46 (COCH$_2$CH$_2$), 22.11 (CH$_2$CH$_2$N$^+$), 22.62, 25.99, 26.18, 27.16, 29.13-29.98 (signal overlap), 31.84, 32.55, 33.11 (COCH$_2$), 52.17 (CH$_3$N$^+$) 52.31 (CH$_3$N$^+$), 58.95 (CH$_3$O), 63.57 (CH$_2$OCO), 64.98 (N$^+$CH$_2$CH), 65.62 (CH$_2$CH$_2$N$^+$), 68.44 (CHCH$_2$O), 68.96 (CH$_2$CH$_2$OCO), 69.23 (CHOCH$_2$), 70.46 (signal overlap), 70.52, 71.86 (CH$_3$OCH$_2$), 71.92 (CHCH$_2$OCH$_2$), 73.27 (CH), 129.69 (2×CH=CH, overlap), 129.90 (2×CH=CH, overlap) 172.61 (C=O);

m/z (ES+) 866.78074 (M$^+$).

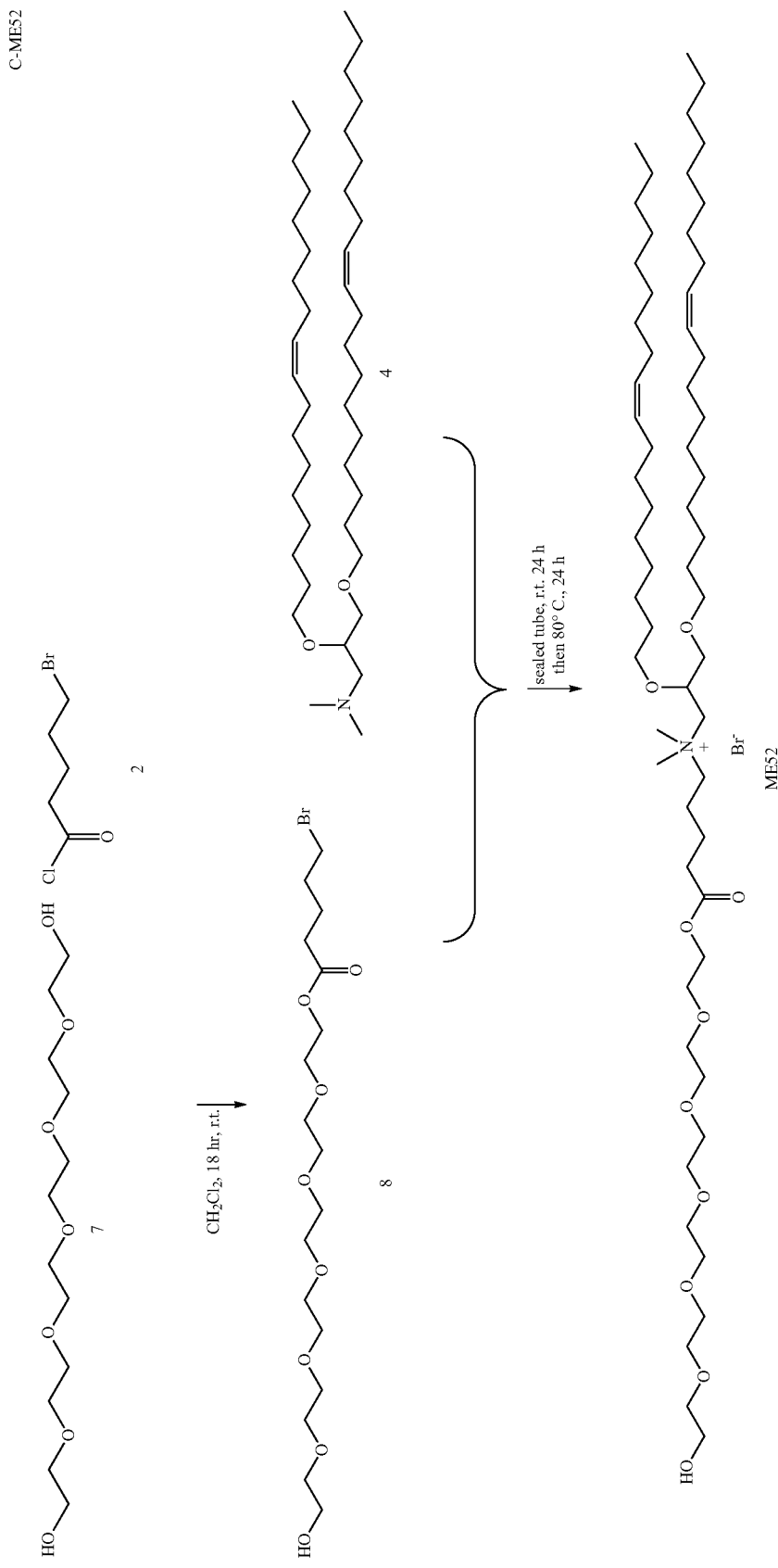

5-Bromopentanoic acid 17-hydroxy-3,6,9,12,15-pentaoxoheptadecyl ester 8

Hexaethyleneglycol 7 (3.75 ml, 15 mmol) was stirred in dichloromethane (10 ml) for 10 min at RT. 5-Bromopentanoyl chloride 2 (670 al, 5 mmol) was added dropwise and stirring was continued for 18 h. The mixture was concentrated in vacuo. The product was purified by flash chromatography on silica (gradient; 5% to 10% methanol in dichloromethane) to obtain the titled product 8 as a yellowish oil (1.429 g, 64%).

$\delta_H$ (300 MHz; CDCl$_3$) 1.44 (2H, m, COCH$_2$CH$_2$), 1.55 (2H, m, CH$_2$CH$_2$Br), 2.04 (2H, t, J 7.2 Hz, COCH$_2$), 3.11 (2H, t, J 6.5 Hz, CH$_2$Br), 3.22-3.38 (22H, m), 3.88 (2H, t, J 4.8 Hz, CH$_2$OCO);

$\delta_C$ (75 MHz; CDCl$_3$) 23.18 (COCH$_2$CH$_2$), 31.64 (CH$_2$CH$_2$Br), 32.77 (CH$_2$Br), 33.03 (COCH$_2$), 61.14 (HOCH$_2$), 63.21 (CH$_2$OCO), 68.76 (CH$_2$CH$_2$OCO), 70.03-70.27 (signal overlap), 72.38 (HOCH$_2$CH$_2$), 172.60 (C=O); m/z (ES+) 467.12615 ([M+Na]$^+$).

(2,3-Bis-octadec-9-enyloxypropyl)-(17-hydroxy-3,6,9,12,15-pentaoxoheptadecyl-oxycarbonylbutyl)-dimethylammonium bromide (ME52)

A mixture of 4 (395 mg, 0.64 mmol) and 8 (330 mg, 0.74 mmol) in acetone (5 ml) was stirred in a sealed-tube at RT for 24 h and than at 80° C. for another 24 h. After cooling, the solvent was evaporated in vacuo. Purification by flash chromatography on silica (gradient; 5% to 10% methanol in dichloromethane) gave ME52 as an orange oil (300 mg, 47%).

$\delta_H$ (300 MHz; CDCl$_3$) 0.85 (6H, t, J 6.7 Hz, 2×CH$_2$CH$_3$), 1.24 (44H, m), 1.52 (4H, m, 2×OCH$_2$CH$_2$CH$_2$), 1.69 (2H, m, COCH$_2$CH$_2$), 1.84 (2H, m, CH$_2$CH$_2$N$^+$), 1.98 (8H, m, 2×CH$_2$CH=CHCH$_2$), 2.44 (2H, t, J 6.9 Hz, COCH$_2$), 3.37-3.43 (11H, m, 2×CH$_3$N$^+$, CHOCH$_2$, CHCH$_2$OCH$_2$, 1H of N$^+$CH$_2$CH), 3.54-3.70 (26H, m, 20×CH$_2$CH$_2$O, HOCH$_2$, CH$_2$NCH$_2$CH, CHCH$_2$OCH$_2$), 3.92 (1H, d, J 13.4 N$^+$CH$_2$CH), 4.06 (1H, m, CH), 4.22 (2H, t, J 4.7 Hz, CH$_2$OCO), 5.31 (4H, m, 2×CH=CH);

$\delta_C$ (75 MHz; CDCl$_3$) 14.05 (2×CH$_2$CH$_3$, overlap), 21.47 (COCH$_2$CH$_2$), 22.09 (CH$_2$CH$_2$N$^+$), 22.59, 25.97, 26.15, 27.13, 29.10-29.70 (signal overlap), 29.97, 31.82, 32.53, 33.19 (COCH$_2$), 52.19 (2×CH$_3$N$^+$, overlap), 61.08 (HOCH$_2$), 63.45 (CH$_2$OCO), 64.99 (N$^+$CH$_2$CH), 65.61 (CH$_2$CH$_2$N$^+$), 68.50 (CHCH$_2$O), 69.05 (CH$_2$CH$_2$OCO), 69.21 (CHOCH$_2$), 69.89, 70.18-70.27 (signal overlap), 71.89 (CHCH$_2$OCH$_2$), 72.31 (HOCH$_2$CH$_2$), 73.25 (CH), 129.69 (2×CH=CH, overlap), 129.87 (2×CH=CH, overlap) 172.79 (C=O); m/z (ES+) 984.84335 (M$^+$).

III—PEG-Acetal Lipid Synthesis

The PEG acetal lipids were of the general structure outlined below. Short PEG chains of 2 different lengths were incorporated. The spacer between the PEG chains of the acetal and cationic head group was of various lengths (from 4 to 8 carbons). R=H was used in most compounds prepared, but R=Me was also incorporated in some compounds as shown. Two representative chain lengths of the lipid were incorporated, mostly C18:1 at C-9 which is used/present in many lipids, and C16:1 at C-11 in the remaining ones.

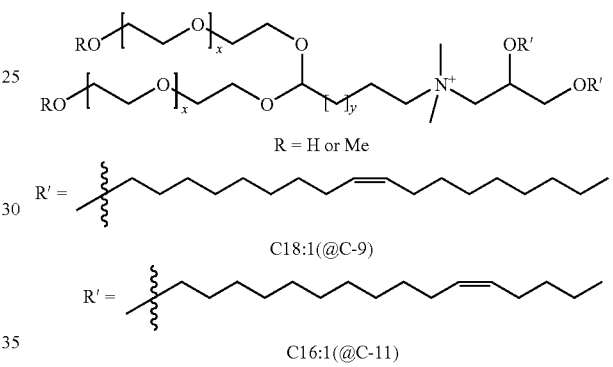

Initially the PEG acetals containing the spacer with a pendant bromide group was prepared for subsequent coupling to the tertiary amine as outlined in Scheme 1.

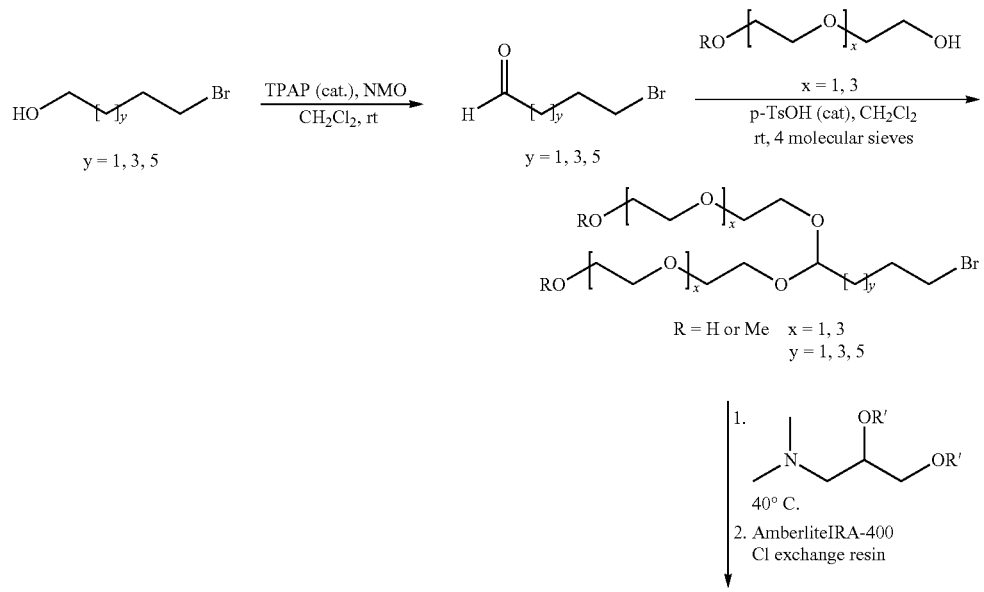

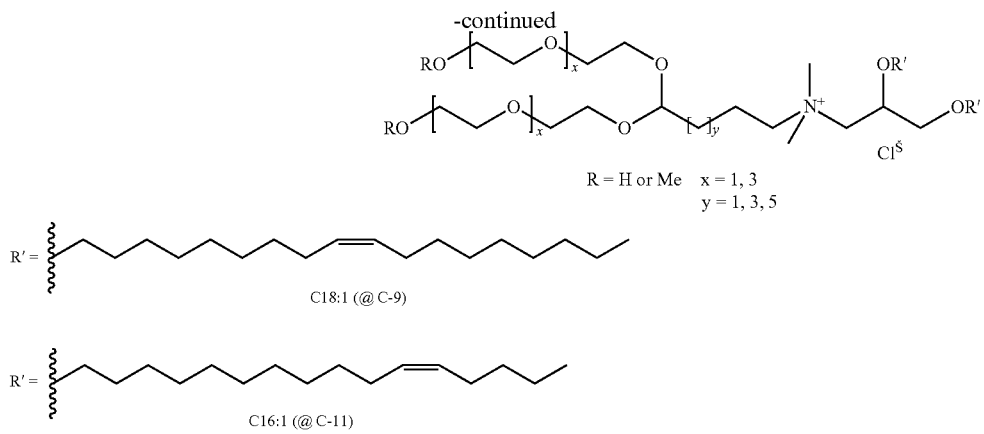

R = H or Me  x = 1, 3
y = 1, 3, 5

R' = [C18:1 (@ C-9) structure]

R' = [C16:1 (@ C-11) structure]

A—General Procedure for PEG Bromoacetal Formation

To a solution of the bromo alcohol (11.1 mmol, 1.0 eq), N-methylmorpholine-N-oxide (NMO, 12.2 mmol, 1.1 eq) and activated molecular sieves (4 Å, powdered; 300 mg per mmol) in anhydrous dichloromethane (45 mL), was added tetra-n-propylammonium perruthenate (TPAP, 1.11 mmol, 0.1 eq). After stirring at RT for 10 min, the suspension was filtered through a small plug of silica gel and the residue washed with dichloromethane (3×20 mL). The combined organic filtrates were concentrated in vacuo to afford the corresponding aldehyde, which was subsequently used without further purification.

A solution of crude aldehyde (11.1 mmol, 1.0 eq), PEG-alcohol (44.4 mmol, 4 eq), p-toluenesulfonic acid monohydride (3.35 mmol, 0.3 eq) and activated powdered molecular sieves (4 Å, 400 mg per mmol) in anhydrous dichloromethane (50 mL) was stirred at rt for 48 h. The suspension was filtered through a small plug of silica gel and the residue washed with dichloromethane (3×20 mL). The combined organic filtrates were washed with saturated sodium hydrogencarbonate solution (30 mL), water (30 mL), and brine (30 mL), dried over sodium sulfate, and then concentrated in vacuo.

a) 7-(3-Bromopropyl)-3,6,8,11-tetraoxatridecane-1, 13-diol (JBW381)

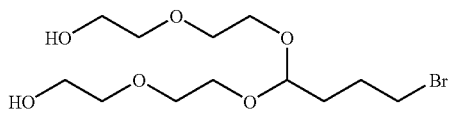 [SMILES: OCCOCCOC(CCCBr)OCCOCCO]

The above procedure was carried out using the following quantities: 1-bromobutan-4-ol (1.70 g, 11.1 mmol), NMO (1.47 g, 12.1 mmol), molecular sieves (3.30 g), dichloromethane (45 mL), TPAP (0.39 g, 1.11 mmol); diethylene glycol (3.99 mL, 44.4 mmol), p-toluenesulfonic acid monohydrate (0.64 g, 3.35 mmol), molecular sieves (4.40 g) and dichloromethane (50 mL). Purification by chromatography on neutral alumina (gradient; dichloromethane to 2% methanol in dichloromethane) afforded the titled compound as a pale yellow oil (0.68 g, 40%).

$R_f$ 0.35 (5% methanol in dichloromethane); $v_{max}$ (neat)/cm$^{-1}$ 3358 br s, 1128 m, 1063 br m; $\delta_H$ (300 MHz; CDCl$_3$) 1.73 (2H, m, CHCH$_2$), 1.87 (2H, m, CH$_2$CH$_2$Br), 3.37 (2H, t, J 6.5 Hz, CH$_2$Br), 3.43 (2H, m, OH), 3.50-3.81 (16H, m, PEG-OCH$_2$CH$_2$), 4.58 (2H, t, J 5.6 Hz, OCHO); $\delta_C$ (75.4 MHz; CDCl$_3$) 28.0 (CH$_2$), 31.7 (CH$_2$), 33.5 (CH$_2$), 61.8 (CH$_2$OH), 64.6 (CHOCH$_2$), 70.6 (CHOCH$_2$CH$_2$), 72.8 (CH$_2$CH$_2$OH), 102.2 (OCHO); m/z (+ES) 369 ([M($^{81}$Br)+Na]$^+$, 97%), 367 ([M($^{79}$Br)+Na]$^+$, 100%); m/z (+HRES) 367.0723 ([M($^{79}$Br)+Na]$^+$, C$_{12}$H$_{25}$BrO$_6$Na requires 367.0727).

b) 7-(5-Bromopentyl)-3,6,8,11-tetraoxatridecane-1, 13-diol (JBW407)

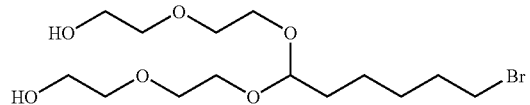 [SMILES: OCCOCCOC(CCCCCBr)OCCOCCO]

The above procedure was carried out using the following quantities: 1-bromohexan-6-ol (1.76 g, 10.3 mmol), NMO (1.33 g, 11.3 mmol), molecular sieves (3.0 g), dichloromethane (40 mL), TPAP (0.37 g, 1.03 mmol); diethylene glycol (4.63 mL, 51.5 mmol), p-toluenesulfonic acid monohydrate (0.59 g, 3.90 mmol), molecular sieves (4.0 g) and dichloromethane (50 mL). Purification by flash chromatography on silica (gradient; dichloromethane to 5% methanol in dichlorometane) afforded the titled compound as a pale yellow oil (0.45 g, 12%).

$R_f$ 0.38 (5% methanol in dichloromethane); $v_{max}$ (neat)/cm$^{-1}$ 3362 br s, 1124 m, 1074 br m; $\delta_H$ (300 MHz; CDCl$_3$) 1.35 (4H, m, CHCH$_2$CH$_2$CH$_2$), 1.59 (2H, dt, J 5.7, 8.2 Hz, CHCH$_2$CH$_2$), 1.79 (2H, tt, J 6.7, 7.1 Hz, CH$_2$CH$_2$Br), 3.27 (2H, t, J 5.7 Hz, OH), 3.36 (2H, t, J 6.7 Hz, CH$_2$Br), 3.51-3.82 (16H, m, PEG-OCH$_2$CH$_2$), 4.54 (2H, t, J 5.7 Hz, OCHO); $\delta_C$ (75.4 MHz; CDCl$_3$) 23.8 (CH$_2$), 27.8 (CH$_2$), 32.6 (CH$_2$), 32.8 and 33.8 (2×CH$_2$), 61.6 (CH$_2$OH), 64.3 (CHOCH$_2$), 70.5 (CHOCH$_2$CH$_2$), 72.7 (CH$_2$CH$_2$OH), 102.8 (OCHO); m/z (+ES) 398 ([M($^{81}$Br)+Na]$^+$, 95%), 396 ([M($^{79}$Br)+Na]$^+$, 100%); m/z (+HRES) 395.1039 ([M($^{79}$Br)+Na]$^+$, C$_{14}$H$_{29}$BrO$_6$Na requires 395.1040).

c) 13-(5-Bromopentyl)-3,6,9,12,14,17,20,23-octaoxapentacosane-1,25-diol (JBW408)

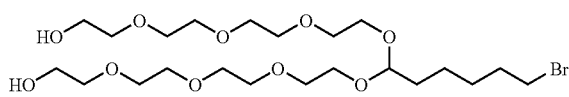 [SMILES: OCCOCCOCCOCCOC(CCCCCBr)OCCOCCOCCOCCO]

The above procedure was carried out using the following quantities: 1-bromohexan-6-ol (1.76 g, 10.3 mmol), NMO (1.33 g, 11.3 mmol), molecular sieves (3.0 g), dichloromethane (40 mL), TPAP (0.37 g, 1.03 mmol); tetraethylene glycol (8.88 mL, 51.5 mmol), p-toluenesulfonic acid monohydrate (0.59 g, 3.90 mmol), molecular sieves (2.7 g) and dichloromethane (50 mL). Purification by flash chromatography on silica (gradient; dichloromethane to 5% methanol in dichlorometane) afforded the titled compound as a pale yellow oil (0.49 g, 9%).

R$_f$ 0.33 (5% methanol in dichloromethane); ν$_{max}$ (neat)/cm$^{-1}$ 3418 br m, 1185 m, 1107 m, 1072 br m;

δ$_H$ (300 MHz; CDCl$_3$) 1.33 (4H, m, CHCH$_2$CH$_2$CH$_2$), 1.55 (2H, dt, J 5.7, 8.0 Hz, CHCH$_2$CH$_2$), 1.79 (2H, tt, J 6.8, 7.3 Hz, CH$_2$CH$_2$Br), 3.00 (2H, t, J 6.3 Hz, OH), 3.33 (2H, t, J 6.2 Hz, OH), 3.36 (2H, t, J 6.7 Hz, CH$_2$Br), 3.50-3.75 (32H, m, PEG-OCH$_2$CH$_2$), 4.51 (2H, t, J 5.7 Hz, OCHO); δ$_C$ (75.4 MHz; CDCl$_3$) 23.8 (CH$_2$), 27.9 (CH$_2$), 32.6 (CH$_2$), 32.9 and 33.8 (2×CH$_2$), 61.6 (CH$_2$OH), 64.4 (CHOCH$_2$), 70.3-70.6 (OCH$_2$CH$_2$O, signal overlap), 72.5 (CH$_2$CH$_2$OH), 103.0 (OCHO); m/z (+ES) 574 ([M($^{81}$Br)+Na]$^+$, 96%), 572 ([M($^{79}$Br)+Na]$^+$, 100%); m/z (+HRES) 571.2081 ([M($^{79}$Br)+Na]$^+$, C$_{22}$H$_{45}$BrO$_{10}$Na requires 571.2088).

d) 7-(7-Bromoheptyl)-3,6,8,11-tetraoxatridecane-1,13-diol (JBW396)

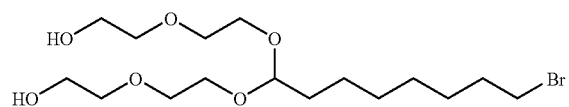 [SMILES: OCCOCCOC(CCCCCCCBr)OCCOCCO]

The above procedure was carried out using the following quantities: 1-bromooctan-8-ol (2 g, 9.57 mmol), NMO (1.12 g, 9.57 mmol), molecular sieves (3.0 g), dichloromethane (40 mL), TPAP (0.34 g, 0.96 mmol); diethylene glycol (5.18 mL, 57.6 mmol), p-toluenesulfonic acid monohydrate (0.55 g, 2.91 mmol), molecular sieves (4.0 g) and dichloromethane (40 mL). Purification by flash chromatography on silica (gradient; dichloromethane to 3% methanol in dichlorometane) afforded the titled compound as colourless oil (1.50 g, 39%).

R$_f$ 0.35 (5% methanol in dichloromethane); ν$_{max}$ (neat)/cm$^{-1}$ 3434 br s, 1128 br m, 1071 br m; δ$_H$ (300 MHz; CDCl$_3$) 1.22-1.47 (8H, m, 4×CH$_2$), 1.60 (2H, m, CH$_2$), 1.82 (2H, tt, J 6.8, 7.1 Hz, CH$_2$CH$_2$Br), 3.22 (2H, t, J 6.2 Hz, OH), 3.37 (2H, t, J 6.8 Hz, CH$_2$Br), 3.56-3.76 (16H, m, PEG-OCH$_2$CH$_2$), 4.56 (2H, t, J 6.0 Hz, OCHO); δ$_C$ (75.4 MHz; CDCl$_3$) 24.6 (CH$_2$), 28.0, 28.6 and 29.2 (3×CH$_2$), 32.7 (CH$_2$), 33.0 (CH$_2$), 34.0 (CH$_2$), 61.7 (CH$_2$OH), 64.3 (CHOCH$_2$), 70.6 (CHOCH$_2$CH$_2$), 72.7 (CH$_2$CH$_2$OH), 102.9 (OCHO); m/z (+ES) 425 ([M($^{81}$Br)+Na]$^+$, 100%), 423 ([M($^{79}$Br)+Na]$^+$, 83%); m/z (+HRES) 423.1361 ([M($^{79}$Br)+Na]$^+$, C$_{16}$H$_{33}$BrO$_6$Na requires 423.1353).

e) 9-(5-Bromopentyl)-2,5,8,10,13,16-hexaoxaheptadecane (JBW409)

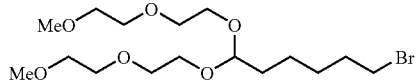 [SMILES: COCCOCCOC(CCCCCBr)OCCOCCOC]

The above procedure was carried out using the following quantities: 1-bromo-hexan-6-ol (1.76 g, 10.3 mmol), NMO (1.33 g, 11.3 mmol), molecular sieves (3.0 g), dichloromethane (40 mL), TPAP (0.37 g, 1.03 mmol); diethylene glycol methyl ether (3.63 mL, 30.9 mmol), p-toluenesulfonic acid monohydrate (0.59 g, 3.90 mmol), molecular sieves (4.0 g) and dichloromethane (50 mL). Purification by chromatography on neutral alumina (gradient; dichloromethane to 2% methanol in dichlorometane) afforded the titled compound as a pale yellow oil (1.45 g, 35%).

R$_f$ 0.43 (2% methanol in dichloromethane); ν$_{max}$ (neat)/cm$^{-1}$ 1113 br s, 1078 br s, 1028 m, 1001 m; δ$_H$ (300 MHz; CDCl$_3$) 1.38 (4H, dt, J 6.2 Hz, CH$_2$CH$_2$), 1.59 (2H, dt, J 5.7, 8.3 Hz, CHCH$_2$), 1.81 (2H, tt, J 6.8, 7.0 Hz, CH$_2$CH$_2$Br), 3.35 (6H, s, CH$_3$), 3.24-3.49 (2H, m, CH$_2$Br), 3.51-3.82 (16H, m, PEG-OCH$_2$CH$_2$), 4.56 (2H, t, J 5.7 Hz, OCHO); δ$_C$ (75.4 MHz; CDCl$_3$) 23.8 (CH$_2$), 27.9 (CH$_2$), 32.7 (CH$_2$Br), 33.0 (CH$_2$), 33.7 (CH$_2$), 59.0 (CH$_3$), 64.4 (CHOCH$_2$), 70.5 and 70.6 (CH$_2$OCH$_2$), 72.0 (CH$_3$OCH$_2$), 103.1 (OCHO); m/z (+ES) 424 ([M($^{81}$Br)+Na]$^+$, 94%), 423 ([M($^{79}$Br)+Na]$^+$, 100%); m/z (+HRES) 423.1351 ([M($^{79}$Br)+Na]$^+$, C$_{13}$H$_{33}$BrO$_6$Na requires 423.1353).

B—General Procedure for Acetal Lipid Formation

The bromo acetal (0.43 mmol, 1 eq) and tertiary amine (0.57 mmol, 1.3 eq) were stirred in a sealed tube at 40° C. for 48 h. The reaction mixture was dissolved in a 1:1 mixture of chloroform/methanol, passed through an Amberlite® IRA-400 (Cl) ion exchange column eluting with chloroform/methanol (1:1), and then concentrated in vacuo. The tertiary amines A and B were prepared as previously reported (Felgner et al., *Proc. Natl. Acad. Sci. USA*, 1987, 84, 7413-7417; Hurley et al., *J. Org. Chem.*, 2004, 69, 980-984).

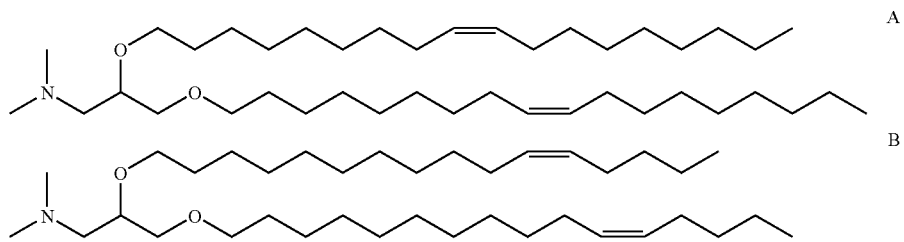

a) N-(2,3-Bis((Z)-octadec-9-enyloxy)propyl)-4,4-bis(2-(2-hydroxyethoxy)ethoxy)-N,N-dimethylbutan-1-aminium chloride (JBW389)

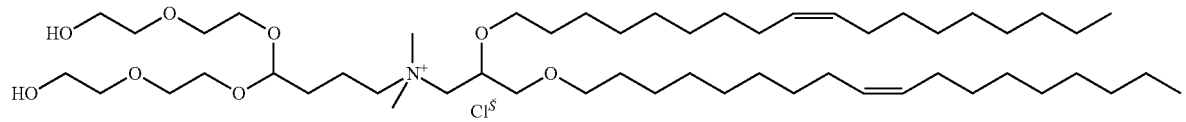 [SMILES: CCCCCCCC/C=C\CCCCCCCCOCC(C[N+](C)(C)CCCC(OCCOCCO)OCCOCCO)OCCCCCCCC/C=C\CCCCCCCC]

The above procedure was carried out using the following quantities: tertiary amine with C18:1 chains A (0.15 g, 0.43 mmol) and JBW381 (0.35 g, 0.57 mmol). Purification by flash chromatography on silica (5% methanol in dichloromethane) afforded the titled compound as a pale yellow oil (81 mg, 21%).

$R_f$ 0.32 (5% methanol in dichloromethane); $v_{max}$ (neat)/cm$^{-1}$ 3383 br s, 1634 w, 1123 br m, 1080 m; $\delta_H$ (300 MHz; CDCl$_3$) 0.83 (6H, t, J 6.6 Hz, 2×CH$_2$CH$_3$), 1.13-1.39 (44H, m), 1.50 (4H, m, 2×CH$_2$), 1.74 (2H, m, CH$_2$CH$_2$CH$_2$N$^+$), 1.83-2.05 (10H, m, 2×CH$_2$CH=CH, CH$_2$CH$_2$N$^+$), 3.28 (3H, s, N$^+$CH$_3$), 3.31 (3H, s, N$^+$CH$_3$), 3.39 (4H, t, J 6.9 Hz, 2×CH$_2$CH$_2$O), 2×CH$_2$N$^+$), 3.52-3.91 (18H, m, OCHCH$_2$OCH$_2$, 16 PEG CH$_2$), 3.97 (1H, m, CHOCH$_2$), 4.65 (1H, t, J 5.6 Hz, CH acetal), 5.34 (4H, m, 2×CH=CH); $\delta_C$ (75.4 MHz; CDCl$_3$) 14.1 (2×CH$_2$CH$_3$), 22.6, 22.7, 23.9, 25.7, 26.0, 26.2, 27.2, 29.3-30.2 (signal overlap), 31.9, 32.6, 32.8, 51.9 (N$^+$CH$_3$), 52.3 (N$^+$CH$_3$), 61.5 (CH$_2$OH), 64.9, 65.2, 68.5, 69.4, 70.5, 72.0, 72.7, 73.3, 103.0 (CH acetal), 129.8 and 130.0 (C=C); m/z (+ES) 914 ([M-Cl]$^+$, 100%); m/z (+HRES) 912.8235 ([M-Cl]$^+$, C$_{55}$H$_{110}$NO$_8$ requires 912.8236).

c) N-(2,3-Bis((Z)-octadec-9-enyloxy)propyl)-6,6-bis(2-(2-(2-hydroxyethoxy)ethoxy)ethoxy)-N,N-dimethylhexan-1-aminium chloride (JBW412)

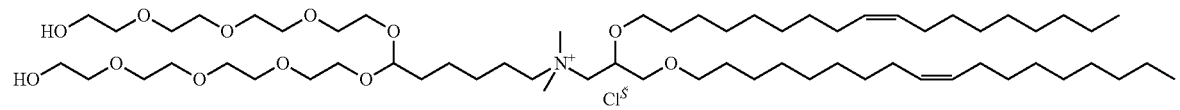

2×CH$_2$CH$_2$O), 3.48-3.94 (22H, m), 4.00 (1H, m, CHOCH$_2$), 4.79 (1H, m, CH acetal), 5.33 (4H, m, 2×CH=CH); $\delta_C$ (75.4 MHz; CDCl$_3$) 14.1 (2×CH$_2$CH$_3$), 17.9, 22.7, 26.0, 26.2, 27.2, 29.2-30.2 (signal overlap), 31.9, 32.6, 51.9 (N$^+$CH$_3$), 52.2 (N$^+$CH$_3$), 61.2 (CH$_2$OH), 65.1, 65.9, 66.0, 68.8, 69.3, 70.6, 72.0, 72.7, 73.3, 103.0 (CH acetal), 129.8 and 129.9 (C=C); m/z (+ES) 885 ([M-Cl]$^+$, 100%); m/z (+HRES) 885.7988 ([M-Cl]$^+$, C$_{53}$H$_{107}$NO$_6$ requires 885.7991).

b) N-(2,3-bis((Z)-octadec-9-enyloxy)propyl)-6,6-bis(2-(2-hydroxyethoxy)ethoxy)-N,N-dimethylhexan-1-aminium chloride (JBW411)

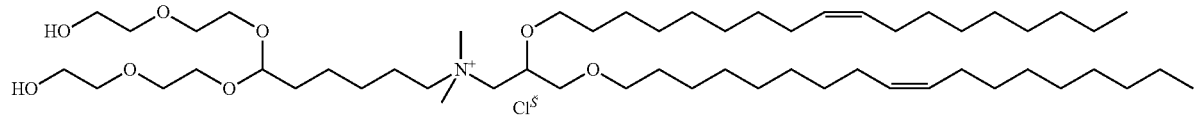

The above procedure was carried out using the following quantities: tertiary amine with C18:1 chains A (0.30 g, 0.48 mmol) and JBW407 (0.16 g, 0.44 mmol). Purification by flash chromatography on silica (5% methanol in dichloromethane) afforded the titled compound as a yellow oil (0.12 g, 29%).

$R_f$ 0.34 (5% methanol in dichloromethane); $v_{max}$ (neat)/cm$^{-1}$ 3357 br m, 1622 m, 1124 m, 1078 br m; $\delta_H$ (300 MHz; CDCl$_3$) 0.86 (6H, t, J 6.7 Hz, 2×CH$_2$CH$_3$), 1.15-1.38 (46H, m), 1.44 (2H, m, CH$_2$), 1.53 (4H, m, 2×CH$_2$), 1.65 (2H, dt, J 6.0, 6.2 Hz, CH$_2$CHO acetal), 1.79 (2H, m, CH$_2$CH$_2$N$^+$), 1.90-2.06 (8H, m, 2×CH$_2$CH=CH), 2.46 (2H, s, br, OH), 3.29 (3H, s, N$^+$CH$_3$), 3.33 (3H, s, N$^+$CH$_3$), 3.32-3.50 (8H, m, 2×CH$_2$CH$_2$O, 2×CH$_2$N$^+$), 3.51-3.93 (34H, m, OCHCH$_2$OCH$_2$, 32 PEG CH$_2$), 4.03 (1H, m, CHOCH$_2$), 4.58 (1H, t, J 5.4 Hz, CH acetal), 5.34 (4H, m, CH=CH); $\delta_C$ (75.4 MHz; CDCl$_3$) 14.1 (2×CH$_2$CH$_3$), 22.5, 22.7, 23.9, 25.8, 26.0, 26.2, 27.2, 29.3-30.0 (signal overlap), 31.9, 32.5, 32.6, 52.0 (2×N$^+$CH$_3$), 61.4 (CH$_2$OH), 64.1, 65.1, 68.5, 69.3, 70.1, 70.4, 70.5-70.6 (signal overlap), 72.0, 72.8, 73.4, 103.0 (CH acetal), 129.8 and 130.0 (C=C); m/z (+ES) 1090 ([M-Cl]$^+$, 100%); m/z (+HRES) 1088.9280 ([M-Cl]$^+$, C$_{63}$H$_{126}$NO$_{12}$ requires 1088.9275).

The above procedure was carried out using the following quantities: tertiary amine with C18:1 chains A (0.30 g, 0.48 mmol) and JBW408 (0.24 g, 0.44 mmol). Purification by flash chromatography on silica (5% methanol in dichloromethane) afforded the titled compound as a pale yellow oil (0.18 mg, 33%).

$R_f$ 0.31 (5% methanol in dichloromethane); $v_{max}$ (neat)/cm$^{-1}$ 3362 br s, 1643 w, 1124 br m, 1082 br m;

$\delta_H$ (300 MHz; CDCl$_3$) 0.85 (6H, t, J 6.5 Hz, 2×CH$_2$CH$_3$), 1.15-1.41 (48H, m), 1.52 (4H, m, 2×CH$_2$), 1.62 (2H, m, CH$_2$CHO acetal), 1.74 (2H, m, CH$_2$CH$_2$N$^+$), 1.97 (8H, m, d) N-(2,3-Bis((Z)-octadec-9-enyloxy)propyl)-6,6-bis(2-(2-methoxyethoxy)ethoxy)-N,N-dimethylhexan-1-aminium chloride (JBW413)

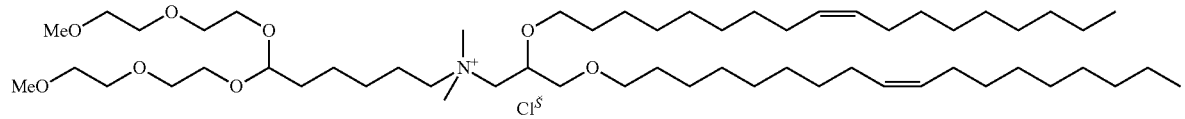 [SMILES: CCCCCCCC/C=C\CCCCCCCCOCC(C[N+](C)(C)CCCCCC(OCCOCCOC)OCCOCCOC)OCCCCCCCC/C=C\CCCCCCCC]

The above procedure was carried out using the following quantities: tertiary amine with C18:1 chains A (0.30 g, 0.48 mmol) and JBW409 (0.18 g, 0.44 mmol). Purification by flash chromatography on silica (2% methanol in dichloromethane) afforded the titled compound as a pale yellow oil (0.21 g, 44%).

$R_f$ 0.41 (2% methanol in dichloromethane); $v_{max}$ (neat)/cm$^{-1}$ 1633 m, 1123 br s, 1086 m, 1030 w; $\delta_H$ (300 MHz; CDCl$_3$) 0.80 (6H, t, J 6.6 Hz, 2×CH$_2$CH$_3$), 1.15-1.41 (48H, m), 1.47 (4H, m, 2×CH$_2$), 1.55 (2H, m, CH$_2$CHO acetal), 1.67 (2H, m, CH$_2$CH$_2$N$^+$), 1.83-2.10 (8H, m, 2×CH$_2$CH=CH), 3.30 (6H, s, 2×N$^+$CH$_3$), 3.30-3.43 (14H, m, 2×CH$_2$CH$_2$O, 2×CH$_2$N$^+$, 2×OMe), 3.46-3.91 (18H, m, OCHCH$_2$OCH$_2$, 16 PEG CH$_2$), 3.99 (1H, m, CHOCH$_2$), 4.50 (1H, t, J 5.6 Hz, CH acetal), 5.28 (4H, m, CH=CH); $\delta_C$ (125.8 MHz; CDCl$_3$) 14.5 (2×CH$_2$CH$_3$), 23.0, 23.1, 24.6, 26.4, 26.6, 27.6, 29.6-30.4 (signal overlap), 32.7, 33.2, 52.3 and 52.6 (2×N$^+$CH$_3$), 59.4 (2×OMe), 65.0, 65.3, 66.6, 68.9, 69.7, 70.8, 71.0, 72.3, 73.8, 103.1 (CH acetal), 130.1 and 130.4 (C=C); m/z (+FAB) 941 ([M-Cl]$^+$, 100%); m/z (+HRFAB) 941.8602 ([M-Cl]$^+$, C$_{57}$H$_{114}$NO$_8$ requires 941.8622).

e) N-(2,3-Bis((Z)-hexadec-11-enyloxy)propyl)-6,6-bis(2-(2-hydroxyethoxy)ethoxy)-N,N-dimethyl-hexan-1-aminium chloride (JBW418)

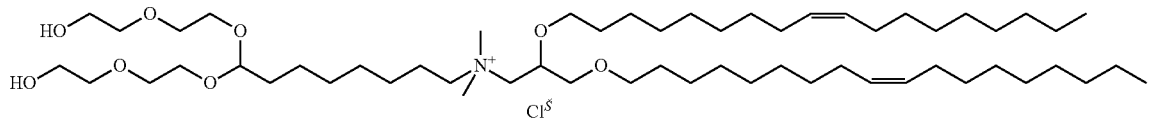

The above procedure was carried out using the following quantities: tertiary amine with C16:1 chains B (0.27 g, 0.48 mmol) and JBW407 (0.16 g, 0.44 mmol). Purification by flash chromatography on silica (5% methanol in dichloromethane) afforded the titled compound as a pale yellow oil (0.13 g, 34%).

$R_f$ 0.33 (5% methanol in dichloromethane); $v_{max}$ (neat)/cm$^{-1}$ 3358 br m, 1661 m, 1124 br m, 1076 br m; $\delta_H$ (300 MHz; CDCl$_3$) 0.86 (6H, t, J 6.9 Hz, 2×CH$_2$CH$_3$), 1.15-1.35 (38H, m), 1.40 (2H, m, CH$_2$), 1.50 (4H, m, 2×CH$_2$), 1.61 (2H, m, CH$_2$CHO acetal), 1.79 (2H, m, CH$_2$CH$_2$N$^+$), 1.92 (8H, m, 2×CH$_2$CH=CH), 2.64 (2H, s, br, OH), 3.30-3.46 (14H, m, 2×CH$_2$CH$_2$O, 2×CH$_2$N$^+$, 2×N$^+$CH$_3$), 3.50-3.86 (18H, m, OCHCH$_2$OCH$_2$, 16 PEG CH$_2$), 4.00 (1H, m, CHOCH$_2$), 4.62 (1H, t, J 5.5 Hz, CH acetal), 5.35 (4H, m, CH=CH); $\delta_C$ (75.4 MHz; CDCl$_3$) 13.9 (2×CH$_2$CH$_3$), 22.2, 22.7, 24.1, 25.8, 26.0, 26.2, 29.2-30.0 (signal overlap), 31.8, 32.2, 32.6, 32.9, 52.1 (2×N$^+$CH$_3$), 61.5 (CH$_2$OH), 64.9, 66.0 68.5, 69.3, 70.6, 72.0, 72.7, 73.4, 103.0 (CH acetal), 130.3 (C=C); m/z (+ES) 857 ([M-Cl]$^+$, 100%); m/z (+HRES) 857.7660 ([M-Cl]$^+$, C$_{51}$H$_{102}$NO$_8$ requires 857.7683).

f) N-(2,3-bis((Z)-octadec-9-enyloxy)propyl)-8,8-bis(2-(2-hydroxyethoxy)ethoxy)-N,N-dimethyloctan-1-aminium chloride (JBW400)

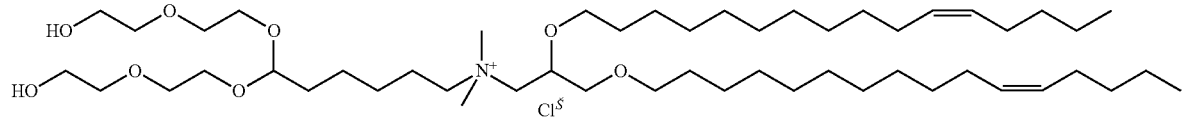 [SMILES: CCCC/C=C\CCCCCCCCCCOCC(C[N+](C)(C)CCCCCC(OCCOCCO)OCCOCCO)OCCCCCCCCCC/C=C\CCCC]

The above procedure was carried out using the following quantities: tertiary amine with C18:1 chains A (0.27 g, 0.44 mmol) and JBW396 (0.16 g, 0.4 mmol). Purification by flash chromatography on silica (5% methanol in dichloromethane) afforded the titled compound as a pale yellow oil (81 mg, 21%).

$R_f$ 0.32 (5% methanol in dichloromethane); $v_{max}$ (neat)/cm$^{-1}$ 3331 br m, 1661 m, 1126 br m 1069 m; $\delta_H$ (300 MHz; CDCl$_3$) 0.85 (6H, t, J 6.7 Hz, 2×CH$_2$CH$_3$), 1.15-1.45 (52H, m), 1.52 (4H, m, 2×CH$_2$), 1.62 (2H, m, CH$_2$CHO acetal), 1.73 (2H, m, CH$_2$CH$_2$N$^+$), 1.88-2.05 (8H, m, 2×CH$_2$CH=CH), 3.36 (3H, s, N$^+$CH$_3$), 3.38 (3H, s, N$^+$CH$_3$), 3.31-3.50 (8H, m, 2×CH$_2$CH$_2$O, 2×CH$_2$N$^+$), 3.50-3.80 (18H, m, OCHCH$_2$OCH$_2$, 16 PEG CH$_2$), 4.01 (1H, m, CHOCH$_2$), 4.60 (1H, t, J 5.8 Hz, CH acetal), 5.34 (4H, m, CH=CH); $\delta_C$ (75.4 MHz; CDCl$_3$) 14.1 (2×CH$_2$CH$_3$), 22.7, 22.8, 24.3, 26.0, 26.2, 27.2, 28.9-29.8 (signal overlap), 31.9, 33.0, 52.1 (2×N$^+$CH$_3$), 61.6 (CH$_2$OH), 64.6, 64.9, 68.4, 69.3, 70.6, 72.0, 72.7, 73.4, 103.0 (CH acetal), 129.8 and 130.0 (C=C); m/z (+ES) 941 ([M-Cl]$^+$, 100%); m/z (+HRES) 941.8659 ([M-Cl]$^+$, C$_{57}$H$_{115}$NO$_8$ requires 941.8617).

g) N-(2,3-Bis((Z)-octadec-9-enyloxy)propyl)-8-hydroxy-N,N-dimethyloctan-1-amminium chloride (JBW438)

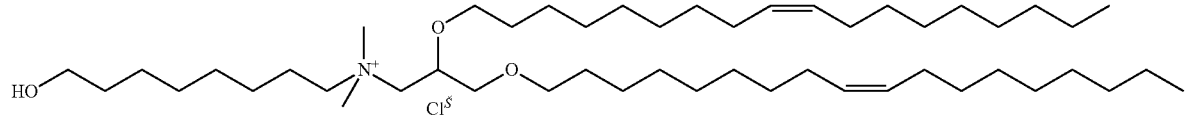 [SMILES: CCCCCCCC/C=C\CCCCCCCCOCC(C[N+](C)(C)CCCCCCCCO)OCCCCCCCC/C=C\CCCCCCCC]

8-Bromooctan-1-ol (0.15 g, 0.71 mmol) and the tertiary amine with C18:1 chains A (0.71 mmol) were stirred in a sealed tube at 40° C. for 48 h. The reaction mixture was dissolved in a 1:1 mixture of chloroform/methanol, and passed through an Amberlite® IRA-400 (Cl) ion exchange column eluting with chloroform/methanol (1:1). The organic solvents were evaporated in vacuo. Purification by flash chromatography on silica (5% methanol in dichloromethane) afforded the title compound as a colourless oil (0.24 g, 47%).

$R_f$ 0.28 (5% methanol in dichloromethane); $\delta_H$ (300 MHz; CDCl$_3$) 0.85 (6H, t, J 6.4 Hz, 2×CH$_2$CH$_3$), 1.16-1.45 (50H, m), 1.52 (8H, m), 1.75 (2H, m, CH$_2$CH$_2$N$^+$), 1.90-2.08 (8H, m, 2×CH$_2$CH=CH), 3.33-3.50 (10H, m, 2×CH$_2$CH$_2$O, 2×N$^+$CH$_3$), 3.52-4.06 (7H, m, 2×CH$_2$N$^+$, CH acetal, OCHCH$_2$OCH$_2$), 5.34 (4H, m, CH=CH); $\delta_C$ (75.4 MHz; CDCl$_3$) 14.1 (2×CH$_2$CH$_3$), 22.7, 25.4, 26.1, 26.3, 27.2, 28.8, 29.3-30.0 (signal overlap), 31.9, 32.4, 32.6, 52.2 and 52.4 (2×N$^+$CH$_3$), 62.5 (CH$_2$OH), 64.9, 66.3, 68.4, 69.3 and 72.0, 73.4, 129.8 and 130.0 (C=C); m/z (+FAB) 749 ([M-Cl]$^+$, 100%); m/z (+HRFAB) 749.7592 ([M-Cl]$^+$, C$_{49}$H$_{99}$NO$_3$ requires 749.7624).

h) N-(2,3-Bis((Z)-octadec-9-enyloxy)propyl)-N,N-dimethyl-8-oxooctan-1-aminium chloride (JBW456) (non-cleavable lipid)

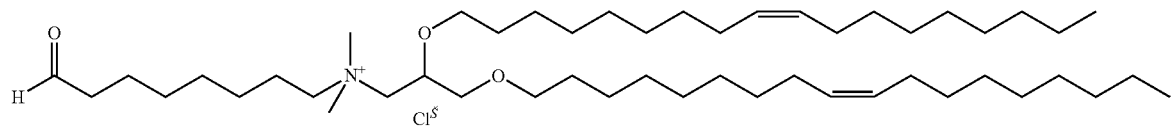 [SMILES: CCCCCCCC/C=C\CCCCCCCCOCC(C[N+](C)(C)CCCCCCCC=O)OCCCCCCCC/C=C\CCCCCCCC]

To a solution of JBW438 (0.23 g, 0.29 mmol), N-methylmorpholine-N-oxide (41 mg, 0.35 mmol) and activated molecular sieves (4 Å, powdered; 100 mg) in anhydrous dichloromethane (5 mL), was added tetra-n-propylammonium perruthenate (10 mg, 0.03 mmol). After stirring at rt for 10 min, the suspension was filtered through a small plug of silica gel and the residue washed with dichloromethane (3×10 mL). The combined organic filtrates were concentrated in vacuo. Purification by flash chromatography on silica (3% methanol in dichloromethane) afforded the titled compound as a yellow oil (0.12 g, 57%).

$R_f$ 0.30 (3% methanol in dichloromethane); $v_{max}$ (neat)/cm$^{-1}$ 1722 m, 1634 w, 1121 br m, 1088 m; $\delta_H$ (300 MHz; CDCl$_3$) 0.87 (6H, t, J 6.6 Hz, 2×CH$_2$CH$_3$), 1.17-1.43 (50H, m), 1.54 (6H, m), 1.75 (2H, m, CH$_2$CH$_2$N$^+$), 1.90-2.07 (8H, m, 2×CH$_2$CH=CH), 2.44 (2H, dt, J 1.4 Hz, 7.2, CH$_2$CHO), 3.32-3.50 (10H, m, 2×CH$_2$CH$_2$O, 2×N$^+$CH$_3$), 3.52-4.06 (7H, m, 2×CH$_2$N$^+$, CH acetal, OCHCH$_2$OCH$_2$), 5.35 (4H, m, CH=CH), 9.76 (1H, t, J 1.5 Hz, CHO); $\delta_C$ (125.8 MHz; CDCl$_3$) 14.5 (2×CH$_2$CH$_3$), 22.1, 23.1, 26.5, 27.6, 29.2, 29.7-30.4 (signal overlap), 32.3, 44.1 (CH$_2$CHO), 52.5 and 52.8 (2×N$^+$CH$_3$), 68.8, 69.7, 72.4 (signal overlap), 73.8, 130.1 (C=C), 202.9 (CHO); m/z (+FAB) 747 ([M-Cl]$^+$, 100%); m/z (+HRFAB) 747.7592 ([M-Cl]$^+$, C$_{49}$H$_{97}$NO$_3$ requires 747.7486).

All the lipids (1 or 2 mg/ml) were stored at 4° C. during several months and ready to use.

Gene Transfer Procedures

I—Cells

The human bronchial epithelial (16HBE14o-) and cystic fibrosis tracheal epithelial (ΣCFTE29o-) cell lines, kindly given by D. C. Gruenert (University of Vermont, Burlington, Vt., USA), were maintained in Eagle's minimum essential medium (MEM) HEPES modification (Sigma, Poole, UK) supplemented with 10% foetal bovine serum (FBS) (Sigma, Poole, UK), 2 mM L-glutamine, 100 U/ml penicillin and 100 μg/ml streptomycin (all from InVitrogen, Paisley, UK). The mouse neuroblastoma (Neuro 2A) and endothelial (bEND.3) cell lines, obtained from ATCC (Manassas, Va., USA), were maintained in Dulbecco's modified Eagle's medium (DMEM) with Glutamax-1 (InVitrogen, Paisley, UK) supplemented with 10% FBS, 1% non-essential amino acids, 1% sodium pyruvate, 100 U/ml penicillin and 100 μg/ml streptomycin (all from InVitrogen, Paisley, UK). AJ3.1 is a mouse embryonic fibroblast line derived from A/J embryos 13.5 days postcoitum as follows: the crania and red organs were removed and the remaining tissue minced using scalpels, digested with trypsin then passed through a cell strainer. The resulting suspension was plated in DMEM with Glutamax-1 containing 10% FCS and 100 U/ml penicillin and 100 μg/ml streptomycin (all from InVitrogen, Paisley, UK), with each embryo maintained as a separate culture. Cells were passaged every few days to maintain sparse colonies until the cultures reached senescence, and after 7-10 days growing colonies of cells were observed. One culture was selected for all further work and is hereafter referred to as AJ3.1. The primary porcine vascular smooth muscle cells (PVSMCs) were prepared using the explant method described previously (Ross, *J. Cell. Biol.*, 1971, 50, 172-186) and maintained in DMEM with Glutamax-1 supplemented with 20% FBS and 100 U/ml penicillin and 100 μg/ml streptomycin (all from InVitrogen, Paisley, UK). All cells were adherent and grew in Falcon 75-cm$^2$ plastic tissue culture flasks and were maintained in a humidified atmosphere of 95% air and 5% CO$_2$ at 37° C.

II—Plasmid DNA

The plasmid pCI-Luc (5.7 kb) consists of pCI (Promega, Southampton, UK) containing the luciferase gene driven by the cytomegalovirus (CMV) immediate/early promoter-enhancer. The plasmid pEGFP-N1 (4.7 kb) containing the gene encoding the green fluorescent protein (GFP) was obtained from Clontech (Hampshire, UK). The plasmid pAB 11 (7.7 kb), carrying the nuclear-localizing β-galactosidase reporter gene lacZ, was a gift from J. Samulski (University of North Carolina, Chapel Hill, N.C.). Human interleukin-2 gene was expressed from pCI-hIL-2 (Siapati et al, 2003; *Br J Cancer* 88: 1641-1648). Murine interleukin-12 was expressed from the plasmid pCI-mIL-12 which was generated by subcloning into pCI (Promega, Southampton, UK) the gene encoding the single-chain fusion protein of the p35 and p40 subunits of murine IL-12 separated by a flexible a linker, from plasmid pcDNA3.1scIL12 (Lode et al, 1998; *Proc Natl Acad Sci USA* 95: 2475-2480). The plasmids were grown in *Escherichia coli* DH5α and purified, after bacterial alkaline lysis, on resin columns (Qiagen Ltd., Crawley, UK). Isopropanol-precipitated DNA pellets were washed with 70% ethanol, then dissolved in water at 1 mg/ml.

III—In Vitro Transfection

Cells were seeded into 96-well plates at $2.5 \times 10^3$ cells per well for bEND.3 cells and at $2 \times 10^4$ cells per well for all the other cells, then incubated overnight at 37° C. in complete growth medium. The following day, lipopolyplex (LPD) formulations were prepared essentially as described previously (Hart et al., 1998), by mixing the components in the following order: 50 µl of lipid (L) at 80 µg/ml in OptiMEM, 70 µl of peptide (P) at 110 µg/ml in OptiMEM and 50 µl of plasmid pCI-Luc (D) at 40 µg/ml in OptiMEM corresponding to a weight ratio of 2:4:1, respectively. All the complexes were mixed by pipetting briefly, kept for 1 h at room temperature and then diluted in OptiMEM to a final volume of 1.57 ml. Two hundred microliters of complexes corresponding at 0.25 µg of plasmid DNA were added to each culture well after removal of the complete growth medium. All the transfections were carried out in 6 wells each. A centrifugation (1500 rpm, during 5 minutes) could be performed to promote the complex sedimentation and cell contact. The cells were incubated with the complexes for 4 h at 37° C. before replacing with fresh media for 24 h, after which reporter gene expression was analysed by luciferase assay (Promega, Madison, Wis., USA). For bEND.3 cells, 5 mM sodium butyrate was added to the transfection medium and to the fresh media to achieve optimal expression levels.

To investigate the GFP expression, bEND.3 cells were seeded into 12-well plates at $1 \times 10^4$ cells per well and all the other cells at $1 \times 10^5$ cells per well. For the transfections, 1 ml of complexes containing 1 ug of pEGFP-N1 plasmid were added to each culture well.

IV—Gene Expression Measurements

Luciferase and Protein Assays

Cells were washed once with PBS before the addition of 20 µl of 1× Reporter Lysis Buffer (Promega, Madison, Wis., USA) to the cells for 20 min at 4° C. before freezing at −80° C. for at least 30 min, followed by thawing at room temperature. Then the luciferase activity was measured during 10 seconds using the Luciferase Assay System (Promega, Madison, Wis., USA) and a Lucy-1 Luminometer (Anthos Ltd., Salzburg, Austria). The amount of protein present in each transfection lysate was determined with the Bio-Rad (Hercules, Calif., USA) protein assay reagent by the manufacturer's instructions, adding 20 µl from the luciferase test to 180 µl of the reagent diluted 1 in 5 and incubating at room temperature for 10 min before comparing the OD590 to a range of BSA standards. In vitro luciferase activity was expressed as Relative Light Units (RLU) per milligram of protein (RLU/mg).

Green Fluorescent Protein Expression

GFP transfections were analysed by flow cytometry. Cells were excited with a 488 nm laser and GFP$^+$ events captured with a 525 nm band pass filter. Transfected cells and an untransfected negative control were removed from wells, washed in PBS then resuspended and fixed in 300 µl 1% PFA in PBS. 10,000 total events were counted and the cells gated to include only viable cells. Cells seeded into 12-well plates were also observed with a Olympus IX70 epifluorescence microscope (Olympus America, Melville, N.Y., USA).

V—In Vivo Transfection

All animal procedures were approved and licensed by the Home Office and performed to the standards required by the UK Co-ordinating Committee on Cancer Research (UKC-CCR) (Workman et al., *British Journal of Cancer*, 1998, 77, 1-10). Female A/J mice (Harlan Laboratories, U.K) of 8-12 weeks old were injected subcutaneously in the right posterior flank with $1.5 \times 10^6$ Neuro 2A cells. After 10±2 days, when tumors had reached approximately 8-12 mm in size, 100 µl of LPD complexes made in 5% glucose and containing 50 ug pCI-Luc or pAB 11 were injected into the tail vein. Experiments were carried out at least six times. Twenty-four hours after injection, mice were killed and tumours and organs were resected and stored at −80° C. Tissues were defrosted in ice, submersed in reporter gene assay lysis buffer (Roche, Germany), homogenized with an IKA homogenizer (IKA, Staufen, Germany) and centrifuged at 4600 rpm during 10 min at 4° C. The supernatant was got back and centrifuged at 13000 rpm during 10 min at 4° C. Luciferase activity in the tissue lysates was measured using a FLUOstar Optima (BMG Labtech, UK) during 30 seconds and was expressed as RLU per milligram of protein (RLU/mg). Two million RLU/30 sec correspond to 1 ng luciferase.

VI—Assessment of β-Galactosidase Localization by Immunohistochemistry

Twenty-four hours after intravenously administration of LPD complexes made with pAB 11 plasmid, the animals were killed and tumours were resected, fixed overnight in 4% paraformaldehyde in PBS at RT, embedded in paraffin wax and 7 µm sections mounted on polylysine coated slides. For immunostaining, the tissue sections were deparaffinized with Histoclear (Raymond A Lamb, Eastbourne, UK), serially rehydrated, covered with 0.3% $H_2O_2$ (v/v) in methanol for 30 minutes at RT to block endogenous peroxidase activity, washed in PBS and covered with 3% normal goat serum (Vector Laboratories, Peterborough, UK) in PBS for 30 minutes at RT to block non-specific binding sites. Then, excess block was removed and a 1:500 dilution of unconjugated rabbit anti-β-galactosidase (AbD serotec, Oxford, UK) in PBS containing 1% BSA and 0.1% $NaN_3$ was applied. Sections were incubated overnight in a humid chamber at 4° C. Control slides were incubated with PBS containing just 1% BSA and 0.1% $NaN_3$. Sections were washed in PBS, then a 1:100 dilution goat anti-rabbit biotinylated antibody (Vector Laboratories, Peterborough, UK) in PBS containing 1% BSA was added and incubated at RT for 30 minutes. Slides were washed in PBS then incubated with a streptavidin-biotinylated peroxidase complex for 1 hour at RT (ABC Reagent, Vector Laboratories, Peterborough, UK). Positively stained cells were identified with 3,3'-Diaminobenzidine (Sigma FAST DAB, Sigma Chemical Co. Dorset, UK). Sections were washed in $dH_2O$, dehydrated through graded alcohols, cleared in Histoclear and mounted with DPX (BDH Labs, Poole, UK). Then, slides were analysed by light microscopy (Axio- Phot 2 microscope, Zeiss, Welwyn Garden City, UK) attached to a digital camera (ProgRes 3012, Kontron Electronic, Chichester, UK) and images were analysed using Adobe Photoshop (Adobe Systems, CA, USA).

VII—Measurement of Cytokine Expression in Tumor Explants

Twenty four hours after i.v. administration of LPD complexes made with lipid ME42/DOPE and peptide ME27 in 5% glucose and containing 25 g of plasmid encoding the hIL-2 and 25 µg of mIL-12, the mice were killed and tumours were harvested, finely minced and cultured in 1 ml of DMEM with Glutamax-1 (InVitrogen, Paisley, UK) supplemented with 10% FBS, 1% non-essential amino acids, 1% sodium pyruvate, 100 U/ml penicillin and 100 µg/ml streptomycin (all from InVitrogen, Paisley, UK) in 6-well plates. Medium was extracted every twenty four hours over five days and cytokine expression levels were determined by DuoSet ELISA Development System (R&D Systems, Abingdon, UK) according to the manufacturer's instructions.

VIII—Animal Vaccinations

Female A/J mice (Harlan Laboratories, UK) of 8-10 weeks old were engrafted with $1.5\times10^6$ Neuro 2A cells subcutaneously (s.c.) in the right posterior flank. On day 3 after injection of tumour cells, when tumours had reached approximately 2×2 mm, animals were vaccinated by intravenously (i.v.) injection of LPD complexes made with lipid ME42/DOPE and peptide ME27 in 5% glucose and containing 25 µg of plasmid encoding the human interleukin-2 gene (IL-2) and 25 µg of murine interleukin-12 gene (IL-12) into the tail vein. Control animals received nothing, 5% glucose or LPD complexes containing 50 µg of empty plasmid pCI. All groups of mice received seven doses of their vaccine, two days apart. Tumour progression was monitored by measuring two perpendicular axes every 2-3 days using callipers. Mice were promptly culled if the tumour reached a diameter of 12 mm. Mice remaining tumour-free three months after the initial injection were rechallenged with $1.5\times10^6$ viable Neuro 2A cells in the opposite flank to the first injection and tumour progression monitored.

IX—Histological of Tumours and Leukocyte Infiltration Analysis

A/J mice with tumour diameter about 12 mm were culled and tumours excised. For histological analysis, tumours were fixed in 4% PFA, embedded in paraffin wax and 7 µm sections mounted on polylysine coated slides. Sections were serially rehydrated and stained with haemotoxylin and eosin, followed by serial dehydration with ethanol and mounting with glass coverslips. Then, slides were analysed with a light microscope (AxioPhot 2 microscope, Zeiss, Welwyn Garden City, UK) attached to a digital camera (ProgRes 3012, Kontron Electronic, Chichester, UK) and images were analysed using Adobe Photoshop (Adobe Systems, CA, USA). For leukocyte infiltration analysis, tumours were washed through cell strainers using DMEM medium to give single cell suspensions. Cells were pelleted by centrifugation (240×g) and erythrocytes were removed by lysis on ice for five minutes with 0.83% ammonium chloride. Remaining cells were resuspended at $1\times10^6$/ml in PBS, 1:15 dilution of PerCP-anti-mouse CD45 (Pharmingen, San Diego, Calif., USA) was applied for 30 min at 4° C. Cells were washed twice in PBS and fixed in 1% PFA. Then, leukocyte infiltration was analysed by flow cytometry.

X—Cathepsin B

Figure 18:
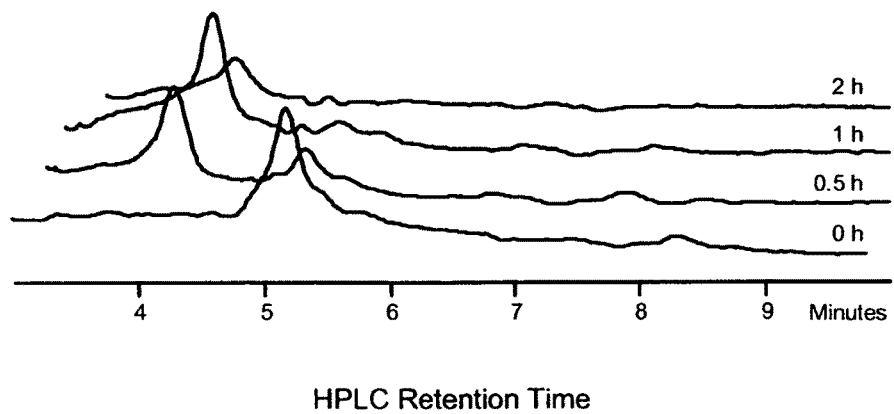
FIG. 18 shows the HPLC results for ME27 at 0 min, 30 min, 1 h, 2 h and 4 h following mixture of the cleavage buffer [prepared by mixing sodium acetate (20 mM), cysteine (5 mM) and EDTA (1 mM) in Millipore water and adjusting to pH 5.0 with acetic acid (5 M), then dissolving lyophilised cathepsin B (1 unit per 100 µl) of the buffer](475 µl), peptide solution (5 mM, 5 µl) and enzyme solution (20 µl).

Lyophilised cathepsin B was divided into aliquots immediately after delivery and stored at −20° C., each aliquot containing about 1 unit of cathepsin B. A buffer solution containing sodium acetate (20 mM), cystein (5 mM) and EDTA (1 mM) in Millipore water was adjusted to pH 5.0 with acetic acid (5 M). Lyophilised cathepsin B (1 unit) was dissolved in 100 µl of this buffer. To start the cleavage buffer (475 al), peptide solution (5 mM, 5 µl) and enzyme solution (20 µl) were mixed and incubated at 37° C. For control experiments the enzyme solution was replaced by an equal amount of buffer. After 30 min, 1 h, 2 h and 4 h 100 µl of the mixture were transferred to an HPLC vial containing acetic acid (5 M, 20 µl) to inactivate the enzyme. The mixture was analysed by HPLC using the standard peptide gradient. FIG. 18 shows ME27 as an example.

(Standard Gradient for HPLC):

| Time [min] | % Water | % Acetonitrile |
| --- | --- | --- |
| 0 | 90 | 10 |
| 25 | 0 | 100 |
| 29 | 0 | 100 |
| 30 | 90 | 10 |
| 40 | 90 | 10 |

XI—In Vitro Esterase Cleavage Experiments

Preparation of Lipid Films

Cationic Lipids were either formulated alone or with DOPE (weight ratio, 1:1). Lipid (10 mg/mL; 100 L [1 mg of lipid]) in chloroform was placed into a sterile glass vial. The solvents were removed in vacuo and further traces of chloroform removed on the high vacuum for 24 h.

Preparation of Liposomes

Sterile water (1 mL) was added to the lipid film, to generate a 1 mg/mL (total lipid) lipid suspension in water. The suspension was allowed to hydrate at 4° C. for 24 h. After warming to 40° C., the mixture was sonicated (bath sonication) for approximately 5 min to generate a clear solution. The resulting liposome formulations were stable for up to 6 months.

Esterase Cleavage of ME42

A phosphate buffer stock solution (0.1 M, pH 7.5) was prepared by mixing an aqueous solution of potassium dihydrogen phosphate (0.1 M, 50 mL) with an aqueous solution of sodium hydroxide (0.1 M, 41 mL). A stock solution for ME42 was prepared (2 mg/mL) according to the method described above, omitting the co-lipid DOPE, using Baxter water. A solution of the pig liver esterase (28 mg, 672 units, capable of hydrolyzing 28 µmol of ethyl butyrate) was prepared by dissolving it in the phosphate buffer (875 µL). To the liposome (125 µL, 250 µg, 0.294 µmol) was added the buffered enzyme solution (875 µL) and the resulting mixture was incubated at 37° C. for 24 hr. Aliquots (200 µL) were taken at T=1, 2, 4, 6, 24 hr and immediately freeze-dried. The lyophilized material was dissolved in dichloromethane (50 µL) and analysed by thin layer chromatography (15% methanol in dichloromethane+acetic acid) with phosphomolybdic acid staining.

Esterase Cleavage of ME42 LPD

Stock solutions for ME27 and pCI-Luciferase were prepared (50 mg/mL and 5 mg/mL, respectively) using Baxter water. Formulation of the stock ME42/DOPE solution (2 mg/mL) was prepared according to the description above. Secondary solutions of the liposome (125 µL), peptide ME27 (10 µL) and pCI-Luciferase (12.5 µL) in the phosphate buffer (125 µL, 250 µL and 250 µL, respectively) were then prepared. The resulting peptide solution was added to the buffered liposome. To the resulting mixture was added the pCI-Luciferase solution and the mixture was left to equilibrate at RT for 1 hr. A solution of the pig liver esterase (28 mg, 672 units, capable of hydrolyzing 28 µmol of ethyl butyrate) in phosphate buffer (223 µL) was then added to the LPD mixture followed by incubation at 37° C. for 24 hr. Aliquots (200 µL)

were taken at T=1, 2, 4, 6, 24 hr and immediately freeze-dried. The lyophilized material was dissolved in dichloromethane (50 μL) and analysed by thin layer chromatography (15% methanol in dichloromethane+acetic acid) with phosphomolybdic acid staining.

XII—Statistical Analysis

Student's t test was performed to assess the statistical significance between different experimental groups with probabilities less than 0.05 (p<0.05) taken to be significant.

RESULTS AND DISCUSSION

I—Transfection Efficiency of Cleavable Peptides

Gene transfer efficiencies of the endosomal enzyme-cleavable peptides ME27, ME28 and ME29 (comprising the cleavable sequence RVRR) were studied in different cell types using a plasmid encoding the luciferase gene and compared with the non-cleavable peptide, ME61. In each of the cell lines, Neuro 2A (FIG. 1a), AJ3.1 (FIG. 1b), bEND.3 (FIG. 1c), 16HBE14o- (FIG. 1d), ΣCFTE29o- (data not shown) and primary PVSMCs (data not shown), ME27 was significantly the best cleavable peptide for in vitro transfections (p<0.05). ME27 was as efficient as the non-cleavable control peptide ME61 in Neuro 2A cells and significantly more efficient than ME61 in other cell lines (p<0.05).

Figure 2:
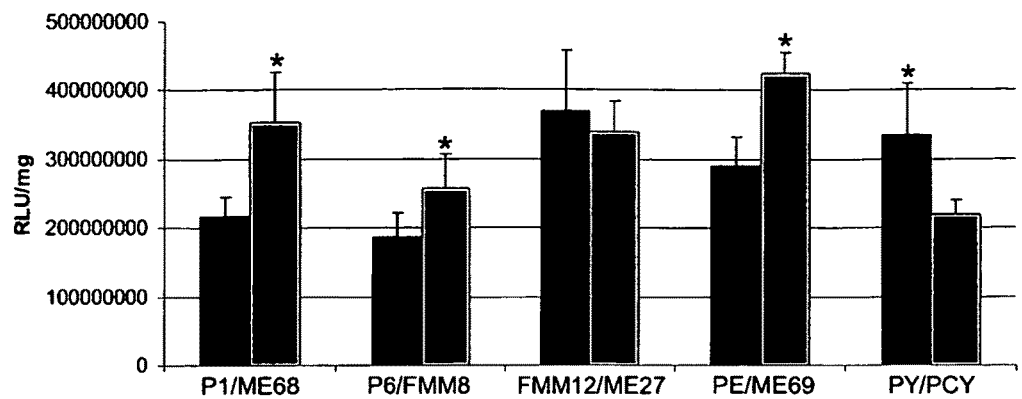
FIG. 2 shows addition effects of a cleavage sequence RVRR in peptides (ME68, FMM8, ME27, ME69 and PCY) on transfection performed in (a) mouse neuroblastoma cells, Neuro 2A, (b) mouse endothelial cells, bEND.3, and (c) human bronchial epithelial cells, 16HBE14o-. Complexes were prepared with a lipofectin:non-cleavable (■) or cleavable (▨) peptide:pCI-Luc weight ratio of 2:4:1. Transfection incubation was performed for 4 h and luciferase activity was measured 24 h later. The relative light units (RLU) measured for 10 sec are expressed as means±s.e.m. per mg of protein. (* $p<0.05$ when non-cleavable peptide was compared with cleavable peptide).
Figure 2:
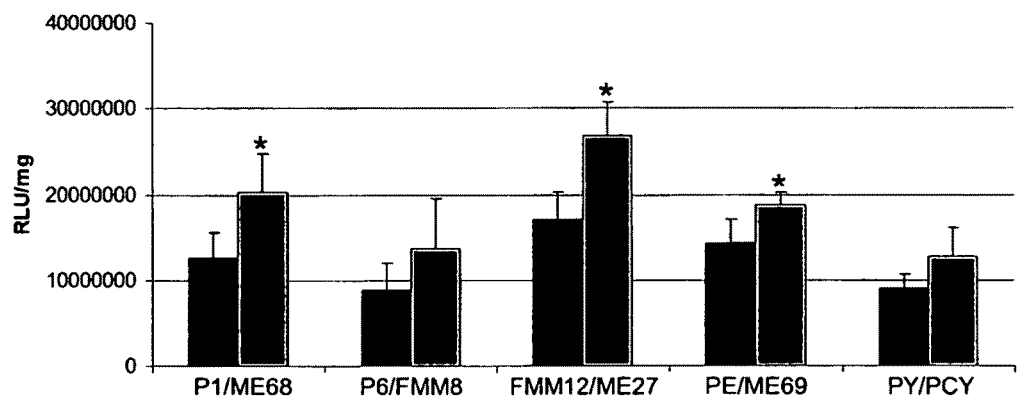
Figure 2:
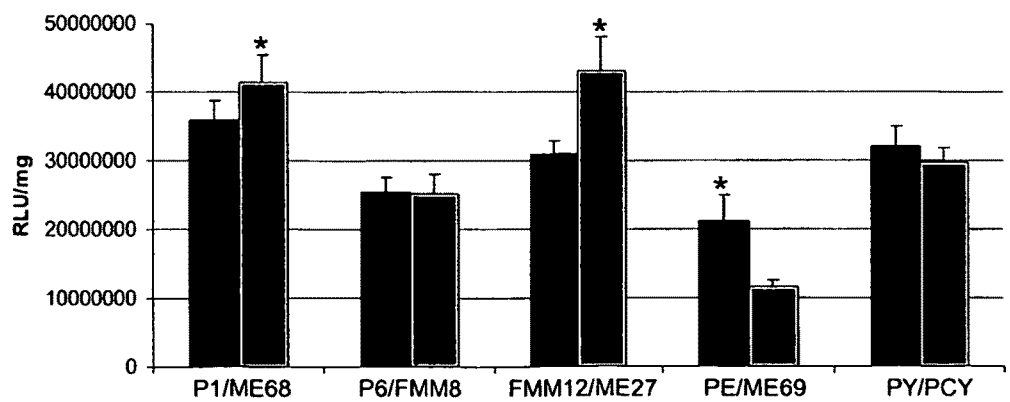

The efficiency of gene transfer of peptides with a cleavable RVRR sequence, recognized by endosomal proteases, was compared to the transfection efficiency of non-cleavable peptides (FIG. 2). In the Neuro 2A cells (FIG. 2a), bEND.3 cells (FIG. 2b) and 16HBE14o- cells (FIG. 2c), most cleavable peptides ME68, FMM8, ME27, ME69 and PCY were as or more efficient than the equivalent non-cleavable peptide controls P1, P6, FMM12, PE and PY, respectively.

It is thus demonstrated that the presence of RVRR cleavable sequence increases transfection efficiency.

Figure 3:
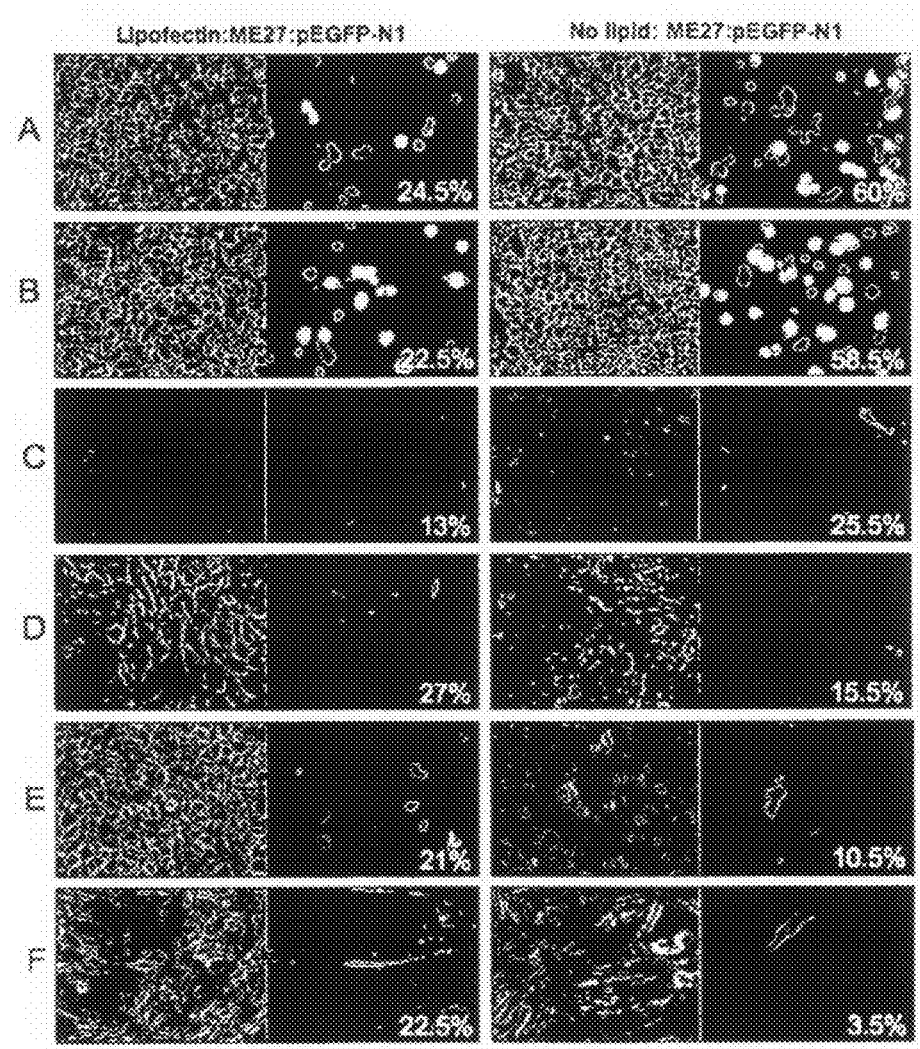
FIG. 3 shows transfection efficiency of peptide ME27 alone (without being complexed with a lipid) performed in (A) mouse neuroblastoma cells, Neuro 2A, (B) mouse embryonic fibroblast, AJ3.1, (C) mouse endothelial cells, bEND.3, (D) human bronchial epithelial cells, 16HBE14o-, (E) cystic fibrosis tracheal epithelial cells (ΣCFTE29o-) and (F) primary porcine vascular smooth muscle cells (PVSMCs). Complexes were prepared with an Lipofectin or none:peptide: pEGFP-N1 weight ratio of 2:4:1. Transfection incubation was performed for 4 h and the percentage of fluorescent cells was determined by flow cytometry 24 h later.

Moreover, in some cell lines like Neuro 2A (FIG. 3A), AJ3.1 (FIG. 3B) and bEND.3 (FIG. 3C) cells, the cleavable peptide alone, without the need for complexing to a lipid, allows efficient gene transfer.

II—Hydrolysis Studies of PEG-Acetal Cleavable Lipids

Hydrolysis of the PEG-acetal lipids was investigated at 37° C. over a pH range of 3 to 7.

Figure 4:
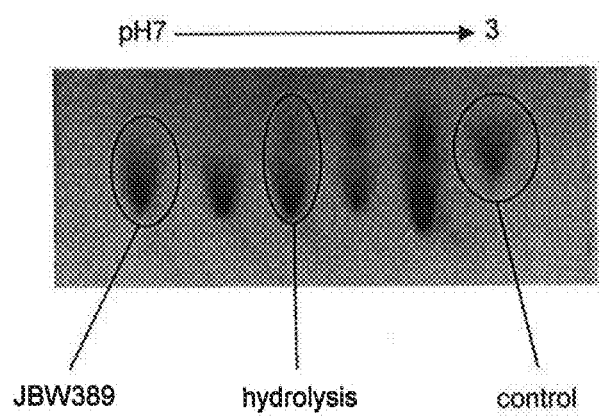
FIG. 4 shows the results of an investigation into the hydrolysis of PEG-acetal cleavable lipid, JBW389, at 37° C. over a pH range of 3 to 7. Acid hydrolysis of the compounds was monitored by TLC and cleavage was then confirmed by mass spectrometry. The control used was the cleaved acetal product, the corresponding aldehyde.

Acid hydrolysis of the compounds was monitored by TLC, and cleavage was then confirmed by mass spectrometry. An example of the TLC analysis method used for compound JBW389 is shown FIG. 4 with a control (the cleaved acetal product, the corresponding aldehyde) and the pH at which hydrolysis for all of the compounds prepared was observed is given in Table II.

TABLE II

Hydrolysis pH of PEG-acetal, acid-cleavable lipids

| Lipid | Structural features | Hydrolysis pH |
|---|---|---|
| JBW389 | PEG2-OH-C4 acetal spacer-C18:1 | 5.5 |
| JBW400 | PEG2-OH-C8 acetal spacer-C18:1 | 4.0 |
| JBW411 | PEG2-OH-C6 acetal spacer-C18:1 | 3.5 |
| JBW412 | PEG4-OH-C6 acetal spacer-C18:1 | 3.0 |
| JBW413 | PEG2-OMe-C6 acetal spacer-C18:1 | 5.0 |
| JBW418 | PEG2-OH-C6 acetal spacer-C16:1 | 3.0 |

III—Transfection Efficiency of PEG-Acetal Cleavable Lipids

Figure 5:
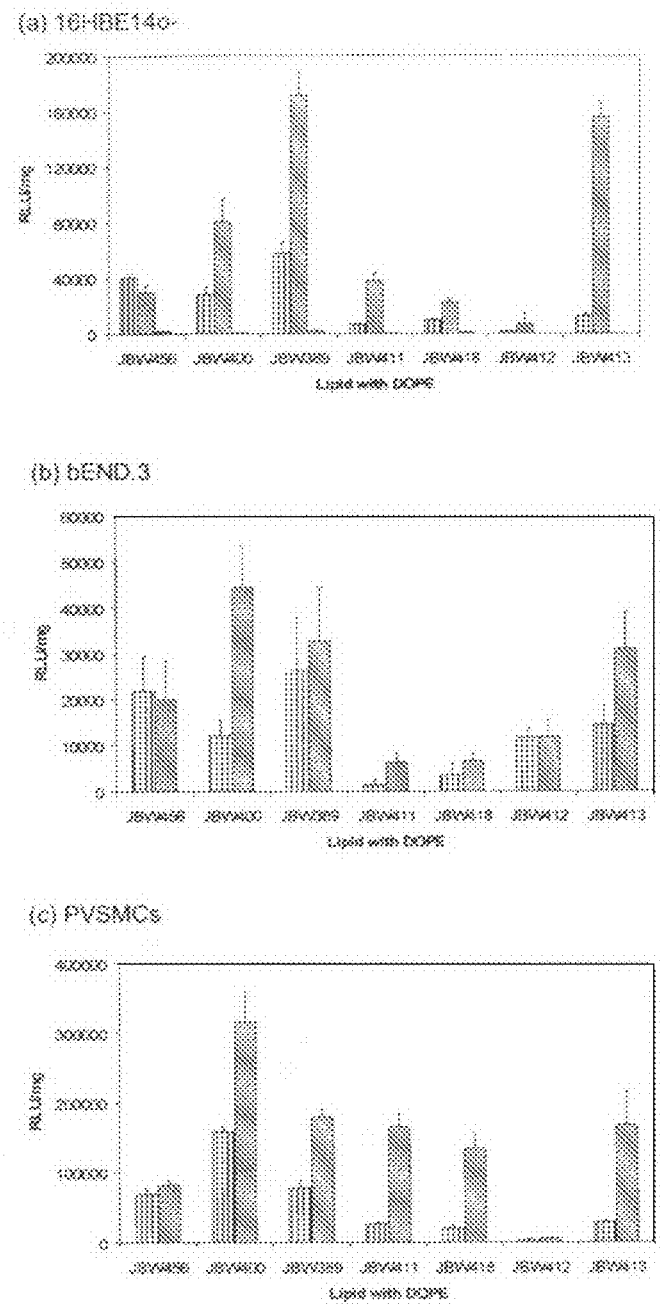
FIG. 5 shows transfection with LPD or LD complexes containing PEG-acetal cleavable lipids performed in (a) human bronchial epithelial cells, 16HBE14o-, (b) mouse endothelial cells, bEND.3, (c) primary porcine vascular smooth muscle cells, PVSMCs, (d) mouse neuroblastoma cells, Neuro 2A, and (e) cystic fibrosis tracheal epithelial cells, XCFTE29o-. Complexes were prepared with an lipid/DOPE:peptide 6 (▥) or E (▨) or none (▤):pCI-Luc weight ratio of 2:4:1. Transfection incubation was performed for 4 h and luciferase activity was measured 24 h later. The relative light units (RLU) measured for 10 sec are expressed as means±s.e.m. per mg of protein.
Figure 5:
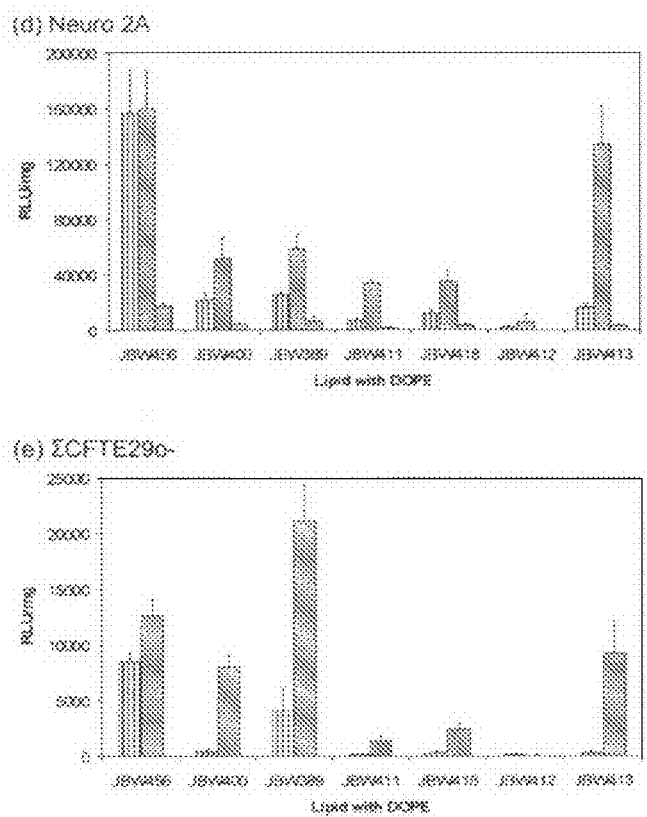

Gene transfer efficiencies of the pH-sensitive lipids PEG-acetal lipids were studied in different cell types using a plasmid encoding the luciferase gene. The results are shown in FIG. 5 for the cell lines 16HBE14o- (FIG. 5a), Neuro 2A (FIG. 5d), bEND.3 (FIG. 5b), ΣCFTE29o- (FIG. 5e), and primary PVSMCs (FIG. 5c). The lipids were compared with the non-cleavable control JBW456. All the lipids needed to be complexed to a peptide to achieve transfection (FIG. 5a) and the addition of DOPE to the lipids was necessary.

In all the cells, when the pH-sensitive lipids were complexed to peptide 6 or E (FIG. 5), the best lipids for transfection were JBW389, JBW413 and JBW400, which were hydrolysed at pH 5.5, 5.0 and 4.0, respectively. JBW411, JBW418 and JBW412 which hydrolysed at pH 3.5, 3.0 and 3.0, respectively were less efficient. Moreover, in all cells apart from Neuro 2A, the pH-sensitive lipid allowing the best transfection efficiency was more efficient than the non-cleavable lipid, JBW456. Indeed, in 16HBE14o- cells (FIG. 5a) and ΣCFTE29o- cells (FIG. 5e), JBW389 was 6 and 2 times better than JBW456, respectively, when they were complexed to peptide E (p<0.05). In bEND.3 cells (FIG. 5b) and PVSMCs cells (FIG. 5c), JBW400 was 2 and 4 times better than JBW456, respectively, when they were complexed to peptide E (p<0.05). In Neuro 2A cells, JBW413 was as efficient as JBW456 when they were complexed to peptide E (p>0.05; FIG. 5d).

There is a strong correlation between the transfection efficiency and the sensitivity of lipids to acid pH allowing their cleavage and so, the rapid dissociation of lipopolyplexes after their uptake by endocytosis.

IV—In Vitro Transfection Efficiency of PEG-Ester Cleavable Lipids

In Vitro Transfection Efficiency without Centrifugation

Figure 6:
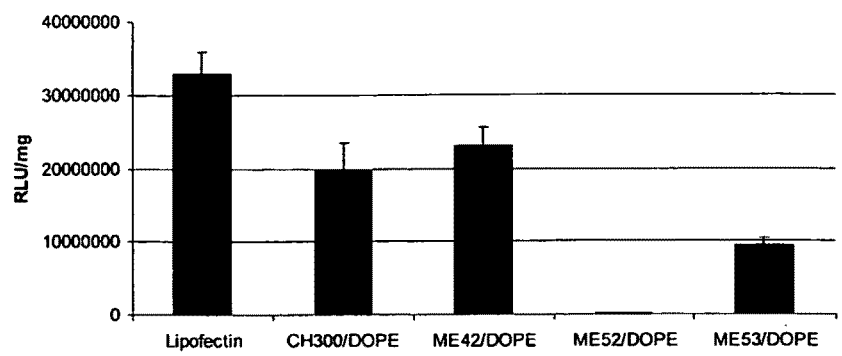
FIG. 6 shows transfection with LPD complexes containing a PEG-ester cleavable lipid (ME42, ME52, ME53), a PEG-ester non-cleavable lipid (CH300) or a non-PEG non-cleavable lipid (Lipofectin) performed in (a) mouse neuroblastoma cells, Neuro 2A, and (b) human bronchial epithelial cells, 16HBE14o-. Complexes were prepared with an lipid:peptide ME27:pCI-Luc weight ratio of 2:4:1. Transfection incubation was performed for 4 h and luciferase activity was measured 24 h later. The relative light units (RLU) measured for 10 sec are expressed as means±s.e.m. per mg of protein.
Figure 6:
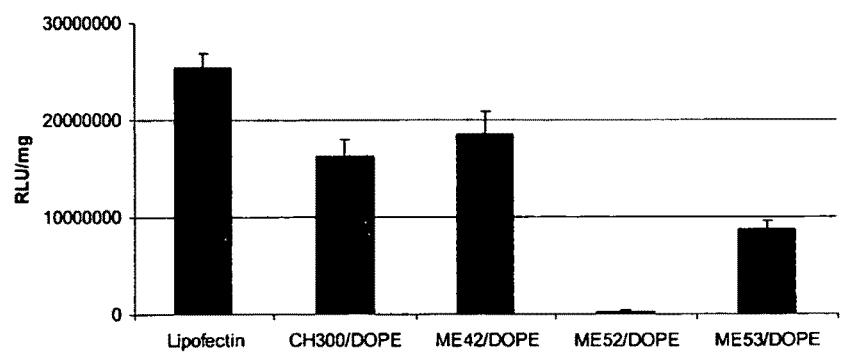

Gene transfer efficiencies of PEG-ester cleavable lipids complexed with cleavable peptide ME27 were studied in different cell types using a plasmid encoding the luciferase gene. The lipids needed to be complexed to a peptide to achieve transfection and the DOPE addition was necessary (data not shown). In cell lines Neuro 2A (FIG. 6a), 16HBE14o- cells (FIG. 6b) and in other cells studied (data not shown), ME42/DOPE was the best PEG-ester cleavable lipid (p<0.05) and was as or more efficient than the PEG non-cleavable lipid, CH300/DOPE, but was less efficient than Lipofectin (p<0.05). Similar results were shown when lipids were complexed to an non-cleavable peptide like peptide E (data not shown).

Size of the Complexes Made with PEG-Ester Cleavable Lipids

Figure 7:
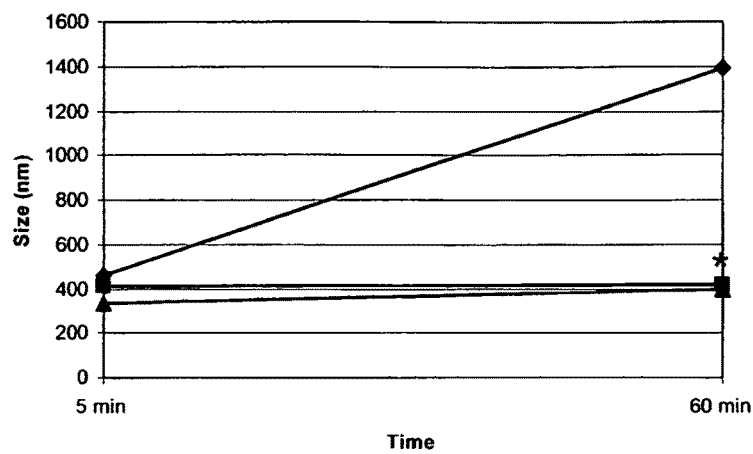
FIG. 7 shows the size of Lipofectin (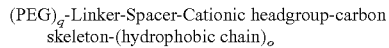), CH3000/DOPE (▬■▬) and ME42/DOPE (▬▲▬) complexed with peptide ME27 and 10 μg pCI-Luc at weight ratio of 2:4:1 and diluted in a total of 1 ml PBS as determined by dynamic light scattering, 5 and 60 min after the complex formation (* $p<0.05$).

The size of the lipopolyplexes was studied since the size could have an effect on transfection efficiency (FIG. 7). The size of LPD complexes made with Lipofectin, CH300/DOPE or ME42/DOPE (complexed with the peptide ME27, diluted in PBS and containing 10 μg pCI-Luc) was measured by laser-light scattering using a Malvern Zetasizer 3000HS (Malvern Instruments, Worcestershire, UK) (FIG. 7). Five minutes after their formation, the size of complexes made with Lipofectin, CH300/DOPE and ME42/DOPE was 457±46 nm, 412±43 nm and 335±11 nm, respectively. So, no difference could be observed between these lipids. However, after 1 hour, whereas the size of complexes made with Lipofectin was 1388±198 nm, the size of complexes made with CH300/DOPE and ME42/DOPE was remained stable, 417±60 and 395±14 nm, respectively (p<0.05). So, complexes made with PEGylated lipid were shown to be smaller and more stable than complexes made of the unPEGylated lipid Lipofectin.

In Vitro Transfection Efficiency after Centrifugation

Figure 8:
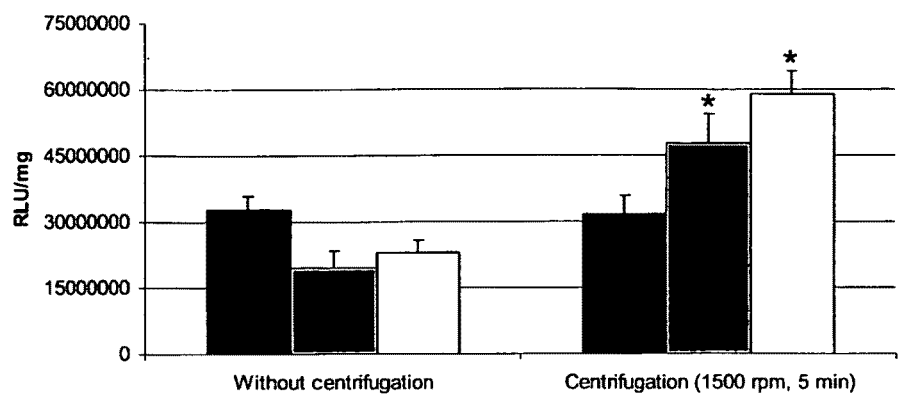
FIG. 8 shows the optimization of transfection with LPD complexes containing an PEGylated lipid (CH300) or PEG-ester cleavable lipid (ME42) performed in (a) mouse neuroblastoma cells, Neuro 2A, and (b) human bronchial epithelial cells, 16HBE14o-. Lipofectin (■), CH300/DOPE (▨) or ME42/DOPE (□) complexes were prepared with an lipid: peptide ME27:pCI-Luc weight ratio of 2:4:1. After addition of complexes to cells, one centrifugation (1500 rpm, during 5 minutes) was performed or not. Transfection incubation was performed for 4 h and luciferase activity was measured 24 h later. The relative light units (RLU) measured for 10 sec are expressed as means±s.e.m. per mg of protein. (* p<0.05 when transfection efficiency after centrifugation was compared with the one without centrifugation)
Figure 8:
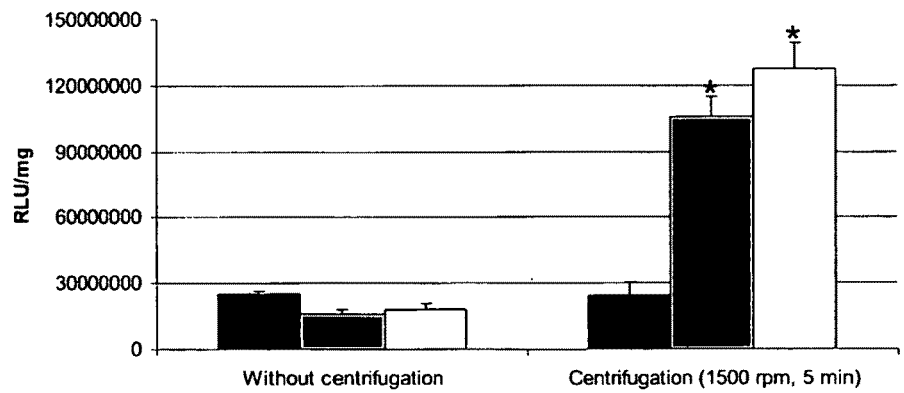

Gene transfer efficiencies of PEG-ester cleavable lipid (ME42), PEGylated lipid (CH300) and Lipofectin were studied in Neuro 2A cells (FIG. 8a), 16HBE14o- cells (FIG. 8b) and in the other cell types (data not shown) following an additional centrifugation (1500 rpm, during 5 minutes) which was performed to help sediment the PEGylated, smaller complexes onto the cells. Whereas without any centrifugation, ME42/DOPE was less efficient than Lipofectin (p<0.05), with a centrifugation of the cells just after the addition of lipopolyplexes, ME42/DOPE was 1.8 times and 5 times more efficient than Lipofectin in Neuro 2A and 16HBE14o- cells, respectively, (p<0.05). So, the centrifugation promotes the complex sedimentation, cell contact and thus transfection. ME42/DOPE was more efficient than CH300/DOPE in most cell lines (FIG. 8).

Figure 9:
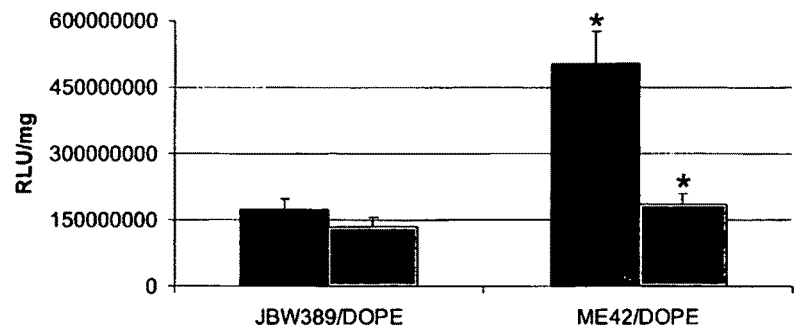
FIG. 9 shows a comparison of transfection with a PEG-acetal cleavable lipid (JBW389) and a PEG-ester cleavable lipid (ME42) performed in mouse neuroblastoma cells, Neuro 2A, (■) and human bronchial epithelial cells, 16HBE14o-, (▨). Complexes were prepared with an lipid/DOPE:peptide ME27:pCI-Luc weight ratio of 2:4:1. After addition of complexes to cells, one centrifugation (1500 rpm, during 5 minutes) was performed. Transfection incubation was performed for 4 h and luciferase activity was measured 24 h later. The relative light units (RLU) measured for 10 sec are expressed as means±s.e.m. per mg of protein. (* p<0.05)

Comparison of In Vitro Transfection Efficiencies Between PEGylated Cleavable Lipids We have compared in vitro transfection efficiency between one of the best PEG-acetal cleavable lipid (JBW389) and the best PEG-ester cleavable lipid (ME42) complexed to peptide ME27 in several cell types using a plasmid encoding the luciferase gene (FIG. 9) or the GFP gene (data not shown) and after a centrifugation. In Neuro 2A cells, 16HBE14o- cells (FIG. 9) and in other cell types (data not shown), both ME42/DOPE and JBW389/DOPE were effective to allow an efficient gene transfer. In 16HBE14o- cells, JBW389/DOPE and ME42/DOPE allowed an efficient gene transfer into 27.5% and 38.5% of cells, respectively (data not shown). However, in the investigated cells, the PEG-ester cleavable lipid ME42/DOPE performed better in vitro gene transfer than the PEG-ester cleavable lipid JBW389/DOPE (p<0.05).

Figure 10:
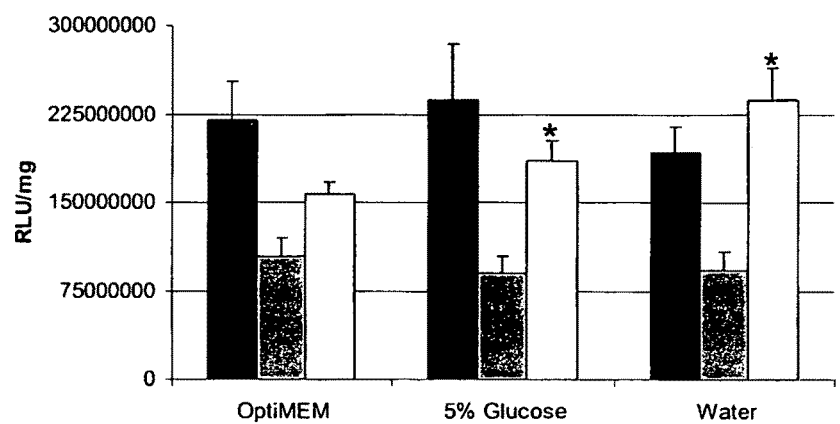
FIG. 10 shows transfection efficiency of PEG cleavable complexes made in different buffers in mouse neuroblastoma cells, Neuro 2A, (■), mouse endothelial cells, bend.3, (▨) and human bronchial epithelial cells, 16HBE14o-, (□). Complexes were prepared with an lipid ME42/DOPE:peptide ME27:pCI-Luc weight ratio of 2:4:1 in OptiMEM, 5% glucose or water and then diluted in OptiMEM just before addition them to each culture well. After addition of complexes to cells, one centrifugation (1500 rpm, during 5 minutes) was performed. Transfection incubation was performed for 4 h and luciferase activity was measured 24 h later. The relative light units (RLU) measured for 10 sec are expressed as means±s.e.m. per mg of protein. (* p<0.05 when transfection efficiency of complexes made in OptiMEM was compared with the one of complexes made in 5% glucose or water)

Transfection Efficiency of PEGylated Cleavable Complexes Made in Different Buffers Finally, we have studied transfection efficiency of lipid ME42/DOPE:peptide ME27:pCI-Luc complex made in OptiMEM, 5% glucose or water in different cell lines (FIG. 10). In Neuro 2A and bEND.3 cells, complexes made in OptiMEM were as efficient as complexes made in 5% glucose or water (p>0.05) (FIG. 10). In 16HBE14o- cells, complexes made in 5% glucose or water were significantly more efficient than complexes made in OptiMEM (p<0.05). These results are important for in vivo transfections where using 5% glucose or water for making the complexes is usually used.

V—In Vivo Transfection Efficiencies

Specific Luciferase Transgene Expression in Tumours

Figure 11:
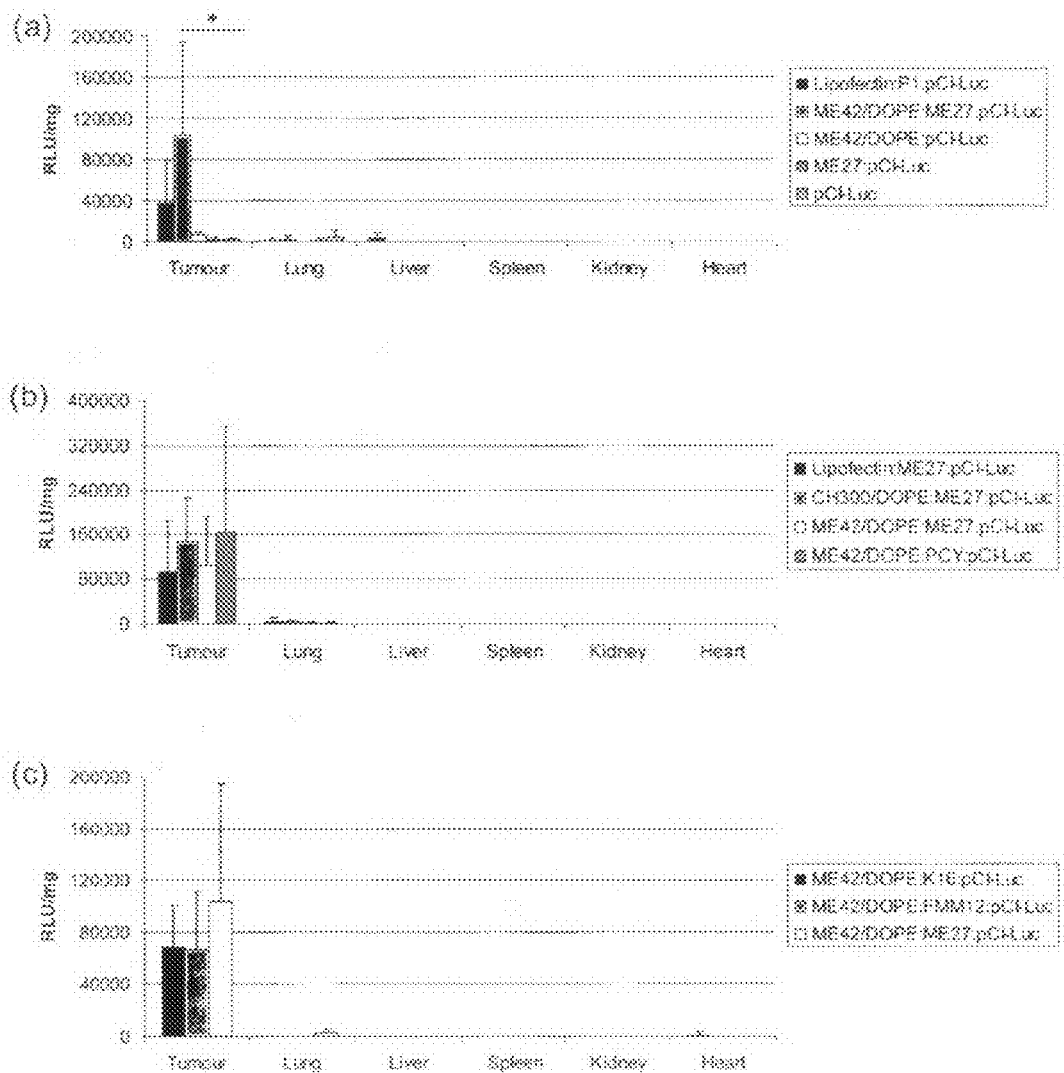
FIG. 11 shows in vivo transfection in female A/J mice bearing a tumour performed with different complexes made in 5% glucose and containing 50 ug pCI-Luc at a weight ratio of 2:4:1 and injected into the tail vein. Twenty-four hours after injection, mice were killed and tumours and organs were resected and luciferase activity in the tissue lysates was measured during 30 seconds and expressed per mg of protein (RLU/mg). The graphs show (a) i.v. administration of plasmid pCI-Luc alone (▨) or complexed with peptide ME27 (◩), lipid ME42/DOPE (□), lipid ME42/DOPE:peptide ME27 (▨) or Lipofectin:peptide P1 (■), (* p<0.05 when transfection efficiency of ME42/DOPE:ME27:pCI-Luc was compared with the one of other complexes), (b) i.v. administration of Lipofectin (■), CH300/DOPE (▨), ME42/DOPE (□) complexed with peptide ME27 and pCI-luc or ME42/DOPE complexed with peptide PCY and pCI-Luc (◩), (c) i.v. administration of peptides K16 (■), FMM12 (▨), ME27 (□) complexed with ME42/DOPE and pCI-luc.

Different complexes made in 5% glucose and containing 50 ug pCI-Luc were injected into the tail vein of female A/J mice bearing a tumour and luciferase expression measured 24 hours later (FIG. 11). Intravenous administration of plasmid pCI-Luc alone or complexed with just the peptide ME27 or lipid ME42/DOPE showed a very low level of luciferase expression in all the organs (less than 6500 RLU/mg) whereas complexed with lipid ME42/DOPE and peptide ME27, the level of luciferase expression was significantly higher (about 105000 RLU/mg in tumour, p<0.05) (FIG. 11a). The cleavable PEGylated complexes (ME42/DOPE:ME27:pCI-Luc) seem also allowing a transfection in tumour more efficient than non-PEGylated non-cleavable complexes (Lipofectin: P1:pCI-Luc, 40000 RLU/mg), p>0.05 (FIG. 11a).

Intravenous administration of different lipids complexed to peptides ME27 or PCY and pCI-Luc was carried out using non-cleavable non-PEGylated lipid (Lipofectin), non-cleavable PEGylated lipid (CH300/DOPE) and cleavable PEGylated lipid (ME42/DOPE) (FIG. 11b). All the lipids allowed a transfection more efficient in tumour than in other organs (p<0.05) but tumour specifity with PEGylated lipids was higher than the one with non-PEGylated lipid (88% versus 50%), p<0.05 (FIG. 11b).

Intravenous administration of different peptides complexed to lipid ME42/DOPE and pCI-Luc was carried out using non-targeting non-cleavable peptide (K16), RGD-targeting non-cleavable peptide (FMM12) and RGD-targeting cleavable peptide (ME27) (FIG. 11c). The RGD-targeting cleavable peptide seemed to allow a transfection in tumour more efficient than the other peptides (105000 RLU/mg versus 70000 RLU/mg) (p>0.05) (FIG. 11c).

It was thus demonstrated that use of a cleavable peptide and PEGylated lipid brought about improved targeting of tumour.

Specific β-Galactosidase Transgene Expression in Tumour Cells

Figure 12:
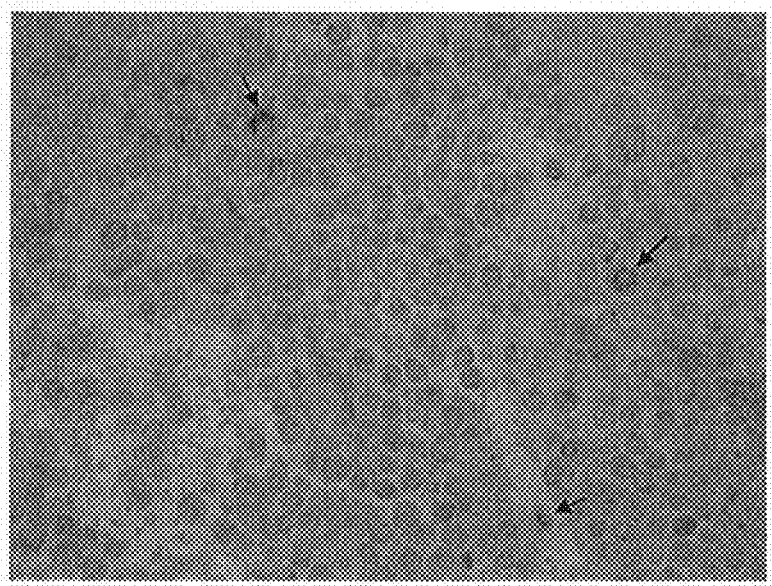
FIG. 12 shows β-galactosidase localization (black arrow) by immunohistochemistry in tumour section of A/J mouse receiving 24 hours before ME42/DOPE:peptide ME27:pAB 11 complexes administered intravenously. A representative section is shown. Magnification ×40.

PEGylated cleavable complexes made with lipid ME42/DOPE:peptide ME27:pAB 11 allowed specific nuclear-localized β-galactosidase activity in tumour cells and no in endothelial cells or the macrophages (FIG. 12), tumour cells being easily recognizable by their morphology with most several nucleus. Control sections showed no evidence of β-galactosidase activity.

Cytokine Expression by the Tumours

Figure 13:
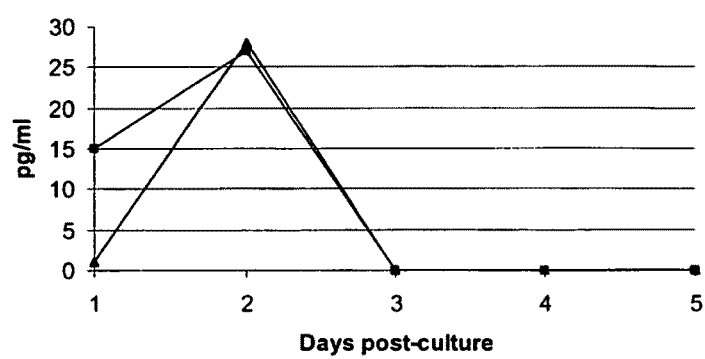
FIG. 13 shows in vivo expression of mIL-12 (■) and hIL-2 (◆) by the tumours from A/J mice i.v. receiving 25 µg of plasmid encoding hIL-2 and 25 µg of mIL-12 complexed with lipid ME42/DOPE and peptide ME27 twenty four hours before their culture in 1 ml of medium. Cytokines production was measured over five days by assaying culture supernatant collected every twenty four hours and determining cytokine levels by ELISA.

PEGylated cleavable complexes made with lipid ME42/DOPE:peptide ME27:pCI-IL2/IL12 allowed a mIL-12 and hIL-2 cytokine expression peak of 27 μg/ml and 28 pg/ml, respectively, forty eight hours after the tumour culture (FIG. 13).

VI—Application for Neuroblastoma Treatment by Immunotherapy

Female A/J mice were engrafted with $1.5 \times 10^6$ Neuro 2A cells in the right posterior flank. On days 3, 5, 7, 9, 11, 13 and 15 post-engraftment, mice bearing established tumours were i.v. injected with LPD complexes made with lipid ME42/DOPE, peptide ME27 and pCI-IL2 and pCI-IL12 plasmids. Control animals received nothing, 5% glucose (data not shown) or LPD complexes containing empty plasmid pCI.

Figure 14:
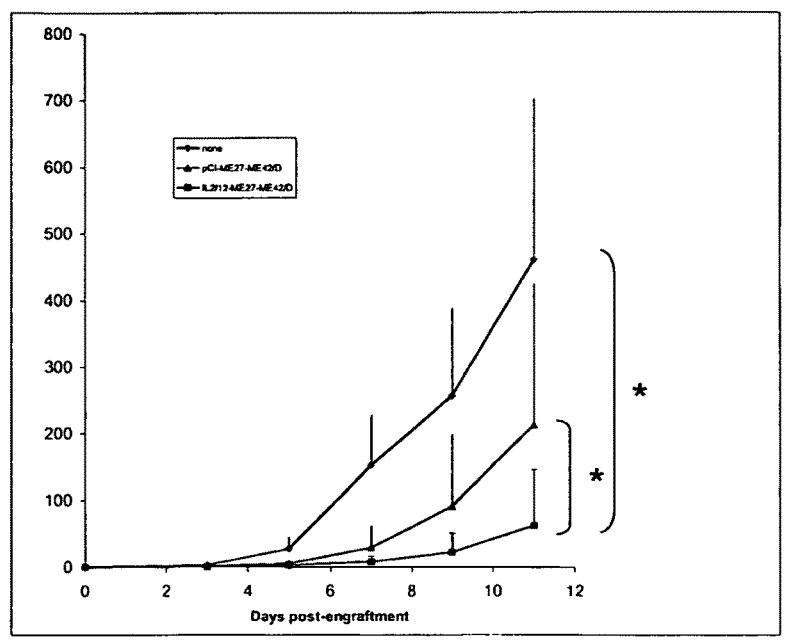
FIG. 14 shows the average tumour volumes of mice bearing established tumours after i.v. injections of therapeutic genes. A/J mice were engrafted with $1.5 \times 10^6$ Neuro 2A cells and i.v. injected with nothing (◆), LPD complexes containing empty plasmid (ME42/DOPE-ME27-pCI, ▲) or LPD complexes containing IL-2 and IL-12 genes (ME42/DOPE-ME27-pCI-IL2/IL12, ■) on days three, five, seven and nine post-engraftment. (*p<0.05 when average tumour volume of mice injected with therapeutic complexes was compared with average tumour volumes of control mice on day eleven post-engraftment)

The average tumour volumes of mice receiving therapeutic complexes was reduced significantly by day eleven post-engraftment to $62 \pm 84$ mm$^3$ compared to control mice receiving nothing or empty complexes where the average tumour volumes were $461 \pm 242$ mm$^3$ and $213 \pm 212$ mm$^3$, respectively (p<0.05) (FIG. 14).

Figure 15:
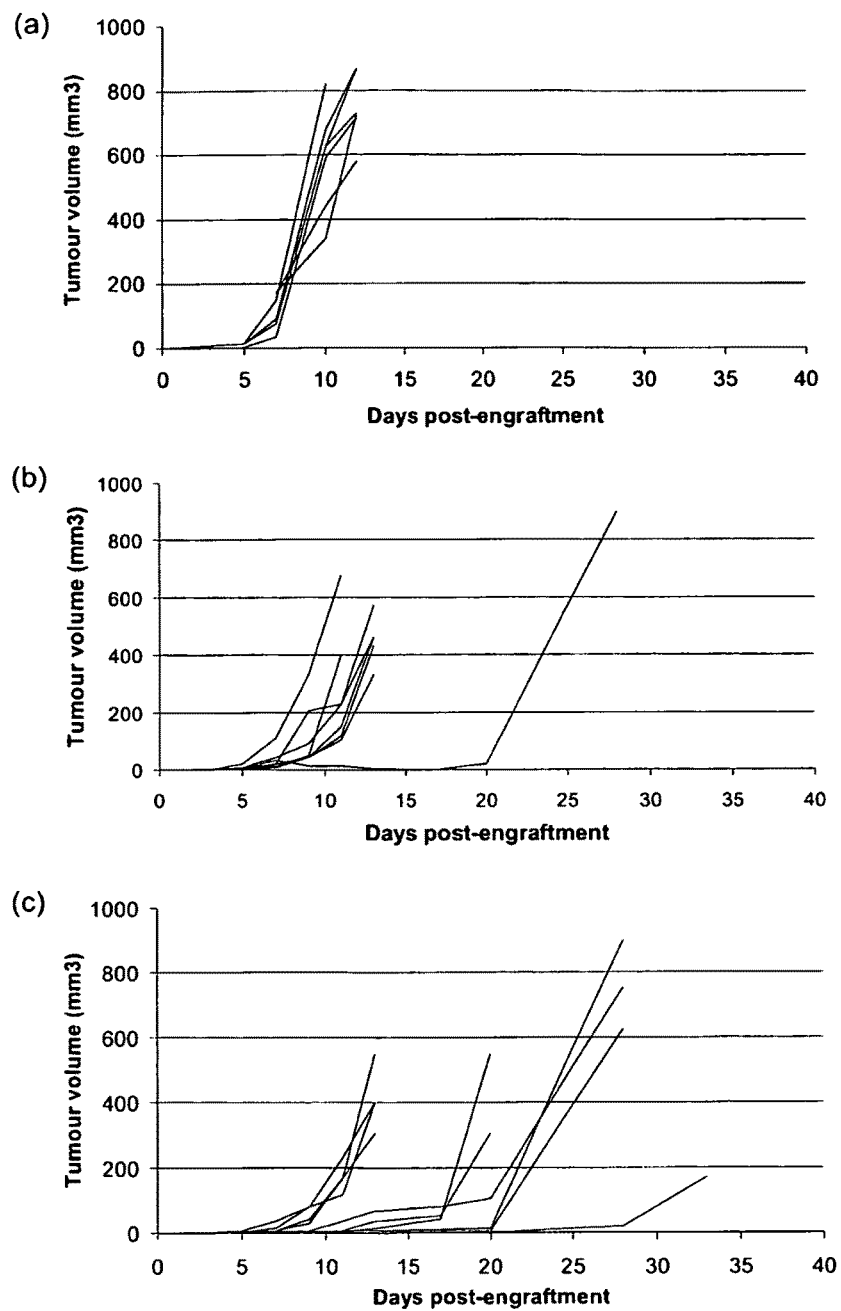
FIG. 15 shows tumour growth of each A/J mouse engrafted with $1.5 \times 10^6$ Neuro-2A cells represented by a single line after seven i.v. injections of (a) nothing, (b) LPD complexes containing empty plasmid (ME42/DOPE-ME27-pCI) or (c) LPD complexes containing IL-2 and IL-12 genes (ME42/DOPE-ME27-pCI-IL2/IL12) on days 3, 5, 7, 9, 11, 13, 15 post-engraftment.
Figure 16:
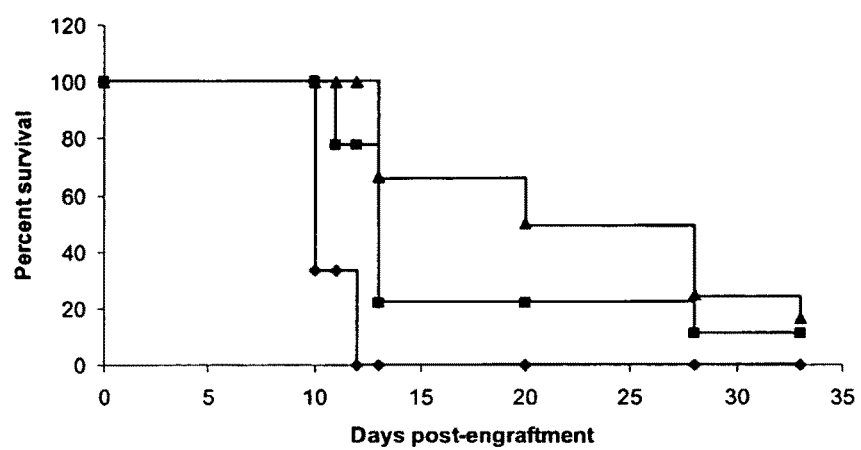
FIG. 16 shows percentage of surviving A/J mice engrafted with $1.5 \times 10^6$ Neuro-2A cells after seven i.v. injections of nothing (blue line), LPD complexes containing empty plasmid (ME42/DOPE-ME27-pCI, yellow line) or LPD complexes containing IL-2 and IL-12 genes (ME42/DOPE-ME27-pCI-IL2/IL12, green line) on days 3, 5, 7, 9, 11, 13, 15 post-engraftment.

On day 12, 100% of mice receiving therapeutic complexes did not develop tumours or had tumour diameter less than 12 mm, while 33.5% and 100% of mice receiving empty complexes or nothing developed tumours and were culled, respectively. On day 20, 50% of mice receiving therapeutic complexes did not develop tumours or had tumour diameter less than 12 mm, while 88% of mice receiving empty complexes developed tumours and were culled. After 1 month, 16.5% and 11% of mice receiving therapeutic complexes or empty complexes were tumour-free, respectively (FIGS. 15 and 16).

Figure 17:
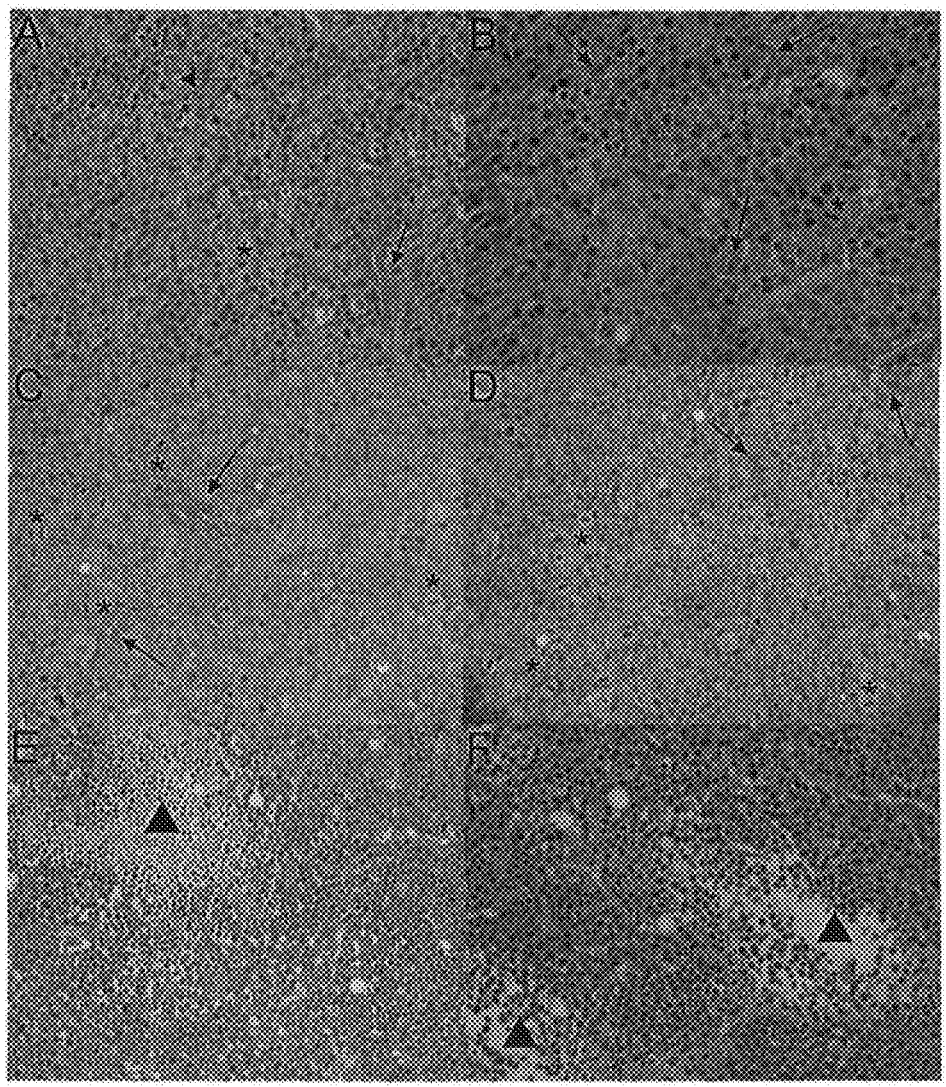
FIG. 17 shows tumour histology on day 12 post-engraftement from A/J mice receiving four i.v injections of (A, B) nothing, (C, D) LPD complexes containing empty plasmid (ME42/DOPE-ME27-pCI) or (E, F) LPD complexes containing IL-2 and IL-12 genes (ME42/DOPE-ME27-pCI-IL2/IL12) on days 3, 5, 7, 9 post-engraftment. Paraffin-embedded tumour sections were stained with haemotoxylin and eosin. Arrows denote blood vessels, stars denote dividing cells and (▲) indicates areas of necrosis. Representative sections are shown. Magnification ×40.

Tumours from control mice were vascularised and had a lot of dividing cells (FIGS. 17A, B, C and D), whereas, tumours from mice receiving therapeutic complexes showed areas of necrosis (FIGS. 17E and F). Anti-CD45 staining showed that tumours from mice receiving therapeutic complexes have two times more of leukocyte infiltration than tumours of control mice with five times more of lymphocytes (Table IV).

TABLE IV

Effects of i.v. injections of therapeutic genes on leukocyte infiltration in tumours

| | Nothing | ME42/DOPE-ME27-pCI | ME42/DOPE-ME27-pCI-IL2/IL12 |
|---|---|---|---|
| Total leukocytes | 117736 ± 16809 | 165252 ± 14750 | 363380 ± 12692 |
| Lymphocytes (%) | 4 | 10 | 58 |

TABLE IV-continued

Effects of i.v. injections of therapeutic genes on leukocyte infiltration in tumours

|  | Nothing | ME42/DOPE-ME27-pCI | ME42/DOPE-ME27-pCI-IL2/IL12 |
|---|---|---|---|
| Monocytes (%) | 35 | 64 | 30 |
| Granulocytes (%) | 61 | 26 | 12 |

Leukocyte infiltration in one million of cells from tumours (n=2 for each group) washed through cell strainers and removed of their erythrocytes was analysed by flow cytometry after incubation with PerCP-anti-mouse CD45 (Pharmingen, San Diego, Calif., USA) for 30 min at 4° C. and fixation in 1% PFA.

To establish if systemic immunological memory responses to tumour cells had been established in mice vaccinated with therapeutic complexes, tumour-free mice (n=4) were rechallenged three months after the initial vaccine with $1.5 \times 10^6$ wild-type Neuro 2A cells in the opposite flank to the original injection, with no further vaccination. Seventy five percent of mice remained tumour-free for at least three months (data not shown).

In conclusion, i.v. administration of therapeutic complexes made with lipid ME42/DOPE and peptide ME27 resulted in significant tumour growth retardation compared to mice receiving nothing or empty complexes and in tumour eradication in few mice with immunological memory response.

VII—In Vitro Esterase Cleavage Experiments

Figure 19:
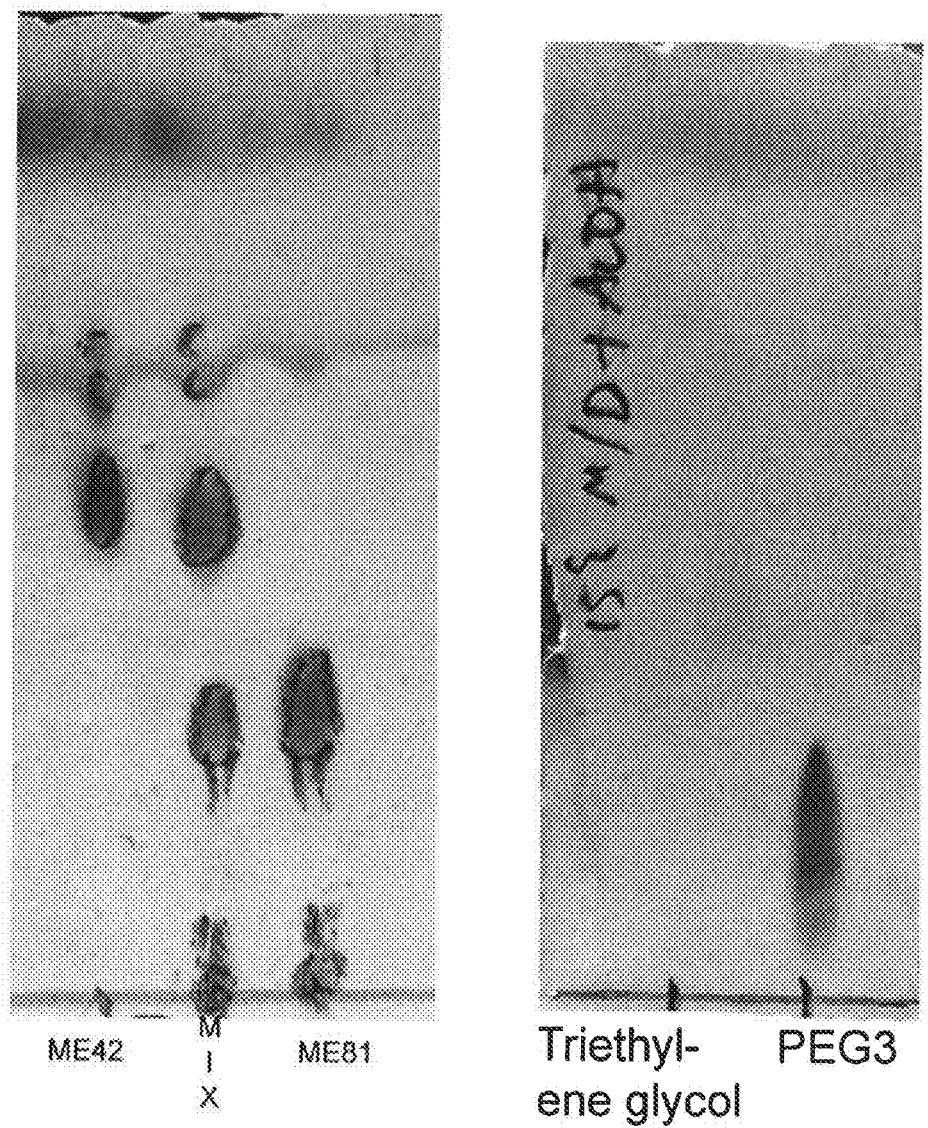
FIG. 19 shows thin layer chromatography plates (15% methanol in dichloromethane+acetic acid) indicating the $R_f$ values of ME42, ME81, DOPE and PEG3.
Figure 20:
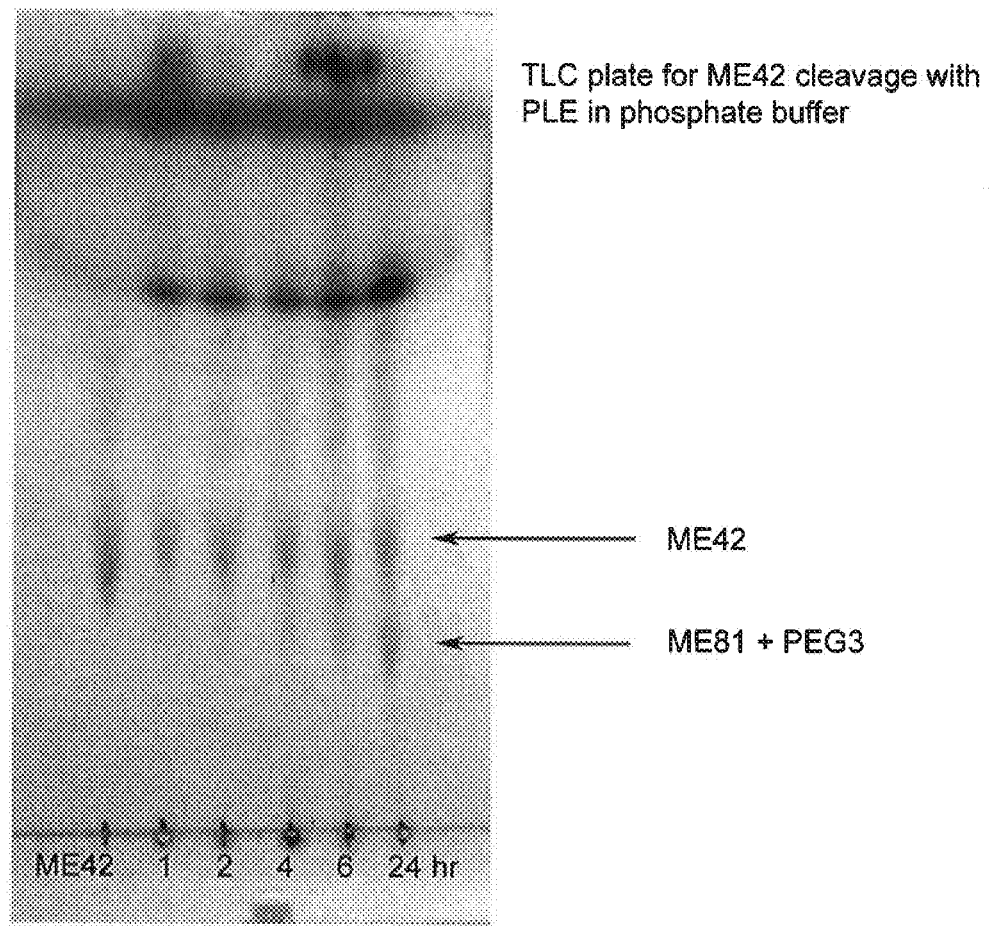
FIG. 20 shows a thin layer chromatography plate (15% methanol in dichloromethane+acetic acid) indicating the degradation of ME42.
Figure 21:
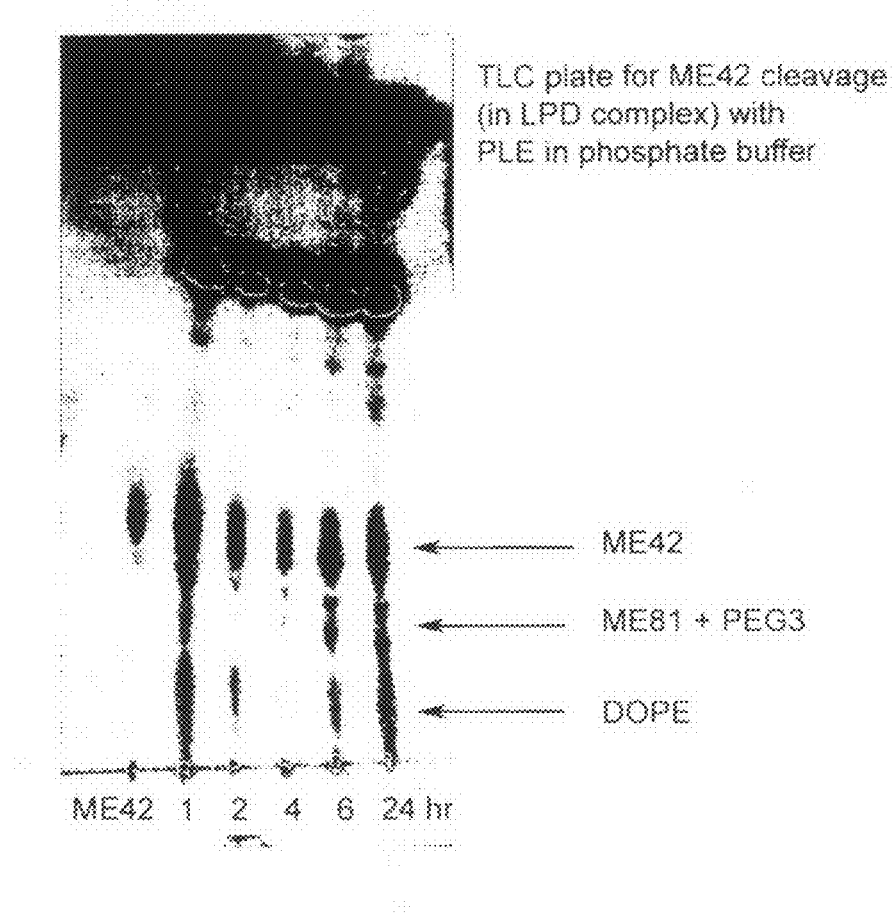
FIG. 21 shows a thin layer chromatography plate (15% methanol in dichloromethane+acetic acid) indicating the degradation of formulated ME42 LPD.

A thin layer chromatography system for authentic samples of ME42, its PEG-cleaved product (ME81), DOPE and triethylene glycol (PEG3) was firstly prepared (FIG. 19). To verify its biodegradability and mimic conditions in the endosome, lipid ME42 (which contains an ester bond) and formulated LPD containing ME42, peptide ME27 and pCI-Luciferase, was treated with an enzyme (pig liver esterase), buffered at pH 7.5. Within one hour the degraded products could be observed, evidenced by the appearance of a spot on the thin layer chromatography plates corresponding to ME81, which has a similar $R_f$ value to that of triethylene glycol (FIG. 20). The intensity of the aforementioned spot steadily increased as the reaction proceeded to a maximum period of 24 hr. A similar observation was made for the reaction on formulated ME42 LPD (FIG. 21).

The invention claimed is:

1. A non-viral delivery complex, for delivering genetic material when combined with a nucleic acid, that comprises:
   (i) a peptide of formula A-B-C wherein
   A is a polycationic nucleic acid-binding component,
   B is a spacer element peptide that is susceptible to cleavage within a cell, and
   C is a cell surface receptor binding component,
   wherein B, the spacer element peptide comprises amino acid sequences susceptible to cleavage by furin selected from $RX^1KR$ [SEQ ID NO: 2] and $RX^2RR$ [SEQ ID NO: 3] in which $X^1$ and $X^2$ which may be the same or different and each represent any amino acid residue, or comprises amino acid sequences susceptible to cleavage by cathepsin selected from $X^3X^4$ in which $X^3$ is selected from Tyrosine (Tyr, Y), Phenylalanine (Phe, F), Leucine (Leu, L), Valine (Val, V) and Isoleucine (Ile, I) and $X^4$ is selected from Glycine (Gly, G), Alanine (Ala, A) and Glutamic acid (Glu, E);

and wherein C, the cell surface receptor binding component, comprises a peptide sequence selected from:
RGD;
RRETAWA [SEQ ID NO: 5];
LDV;
$X^5$SM in which $X^5$ is a basic amino acid residue;
L$X^6$HK [SEQ ID NO: 6] in which $X^6$ is Q or P;
PSG$X^7$ARA [SEQ ID NO: 7] in which $X^7$ is A or T;
S$X^8$RSMNF [SEQ ID NO: 8] in which $X^8$ is an acidic amino acid residue;
L$X^9$HKSMP [SEQ ID NO: 9] in which $X^9$ is P or Q;
P$X^{10}X^{11}X^{12}$T [SEQ ID NO: 19] in which $X^{10}$, $X^{11}$ and $X^{12}$, which may be the same or different, each represents an amino acid residue;
PS$X^{13}$S [SEQ ID NO: 20] in which $X^{13}$ represents an amino acid residue;
Q$X^{14}X^{15}X^{16}$Q [SEQ ID NO: 21] in which $X^{14}$ and $X^{16}$, which may be the same or different, each represents an amino acid residue, and $X^{15}$ represents an amino acid residue having an amide side chain; and
S$X^{17}$S in which $X^{17}$ represents an amino acid residue having an aliphatic side chain; and
(ii) a lipid of formula (III):

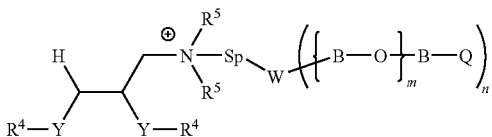

wherein:
each Y is the same or different and is selected from —O—, and —O—C(O)—;
each $R^4$ is the same or different and is selected from a straight or branched, saturated or unsaturated $C_{7-24}$ hydrocarbyl group which is unsubstituted or substituted by one or more substituents selected from hydroxy, halogen and OR', wherein R' is a $C_{1-6}$ hydrocarbyl group;
each $R^5$ is the same or different and is selected from a straight or branched, saturated or unsaturated $C_{1-10}$ hydrocarbyl group which is unsubstituted or substituted by one or more substituents selected from hydroxy, halogen, —OR', —C(O)OH, —CN, —N(R')$_2$, and —C(O)R', wherein each R' is the same or different and is a $C_{1-6}$ hydrocarbyl group;
Sp is a $C_{1-8}$ alkylene group which is unsubstituted or substituted by one or more substituents selected from hydroxy, halogen and OR', wherein R' is a $C_{1-6}$ hydrocarbyl group;
W is selected from —O—C(O)—, —C(O)O—, and the group of formula (IV):

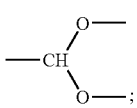 (IV)

n denotes the number of chains, and n=1 if the linker W is —O—C(O)— or —C(O)O—, and n=2 if the linker W is the group of formula (IV);
each B is the same or different and is a $C_{1-6}$ alkylene group which is unsubstituted or substituted by one or more substituents selected from hydroxy, halogen, —OR$^1$, —C(O)OH, —CN, —NR$^1$R$^2$, —C(O)OR$^1$, —OC(O)R$^1$ and —C(O)R$^1$;
$R^1$ and $R^2$ are the same or different and are $C_{1-4}$ hydrocarbyl;
m is an integer from 1 to 100; and
Q is selected from —N$^+$(R$^3$)$_3$, —OH, and —OR$^3$ wherein R$^3$ is an unsubstituted $C_{1-4}$ alkyl group or a trifluoromethyl group.

2. A non-viral delivery complex, for delivering genetic material when combined with a nucleic acid, that comprises:
(i) a peptide of formula A-B-C wherein
A is a polycationic nucleic acid-binding component,
B is a spacer element peptide that is susceptible to cleavage within a cell, and
C is a cell surface receptor binding component,
wherein B, the spacer element peptide comprises amino acid sequences susceptible to cleavage by furin selected from R$X^1$KR [SEQ ID NO: 2] and R$X^2$RR [SEQ ID NO: 3] in which $X^1$ and $X^2$ which may be the same or different and each represent any amino acid residue, or comprises amino acid sequences susceptible to cleavage by cathepsin selected from $X^3X^4$ in which $X^3$ is selected from Tyrosine (Tyr, Y), Phenylalanine (Phe, F), Leucine (Leu, L), Valine (Val, V) and Isoleucine (Ile, I) and $X^4$ is selected from Glycine (Gly, G), Alanine (Ala, A) and Glutamic acid (Glu, E);
and wherein C, the cell surface receptor binding component, comprises a peptide sequence selected from:
RGD;
RRETAWA [SEQ ID NO: 5];
LDV;
$X^5$SM in which $X^5$ is a basic amino acid residue;
L$X^6$HK [SEQ ID NO: 6] in which $X^6$ is Q or P;
PSG$X^7$ARA [SEQ ID NO: 7] in which $X^7$ is A or T;
S$X^8$RSMNF [SEQ ID NO: 8] in which $X^8$ is an acidic amino acid residue;
L$X^9$HKSMP [SEQ ID NO: 9] in which $X^9$ is P or Q;
P$X^{10}X^{11}X^{12}$T [SEQ ID NO: 19] in which $X^{10}$, $X^{11}$ and $X^{12}$, which may be the same or different, each represents an amino acid residue;
PS$X^{13}$S [SEQ ID NO: 20] in which $X^{13}$ represents an amino acid residue;
Q$X^{14}X^{15}X^{16}$Q [SEQ ID NO: 21] in which $X^{14}$ and $X^{16}$, which may be the same or different, each represents an amino acid residue, and $X^{15}$ represents an amino acid residue having an amide side chain; and
S$X^{17}$S in which $X^{17}$ represents an amino acid residue having an aliphatic side chain; and
(ii) a lipid of formula (VI):

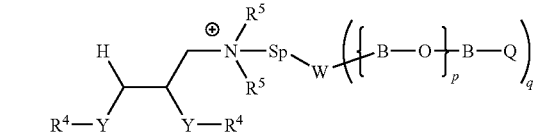

wherein:
each Y is the same or different and is selected from —O—, and —O—C(O)—;
each $R^4$ is the same or different and is selected from a straight or branched, saturated or unsaturated $C_{7-24}$ hydrocarbyl group which is unsubstituted or substituted by one or more substituents selected from hydroxy, halogen and OR', wherein R' is a $C_{1-6}$ hydrocarbyl group;

each $R^5$ is the same or different and is selected from a straight or branched, saturated or unsaturated $C_{1-10}$ hydrocarbyl group which is unsubstituted or substituted by one or more substituents selected from hydroxy, halogen, —OR', —C(O)OH, —CN, —N(R')$_2$, and —C(O)R', wherein each R' is the same or different and is a $C_{1-6}$ hydrocarbyl group;

Sp is a $C_{1-8}$ alkylene group which is unsubstituted or substituted by one or more substituents selected from hydroxy, halogen and OR', wherein R' is a $C_{1-6}$ hydrocarbyl group;

W is a group susceptible to cleavage within a cell;

q denotes the number of P-G-chains;

each B is the same or different and is a $C_{1-6}$ alkylene group which is unsubstituted or substituted by one or more substituents selected from hydroxy, halogen, —OR$^1$, —C(O)OH, —CN, —NR$^1$R$^2$, —C(O)OR$^1$, —OC(O)R$^1$ and —C(O)R$^1$;

$R^1$ and $R^2$ are the same or different and are $C_{1-4}$ hydrocarbyl;

p is an integer from 1 to 8; and

Q is selected from —N$^+$(R$^3$)$_3$, —OH, and —OR$^3$ wherein $R^3$ is an unsubstituted $C_{1-4}$ alkyl group or a trifluoromethyl group.

3. A non-viral transfection complex comprising the non-viral delivery complex as claimed in claim 1 or claim 2 and a nucleic acid.

4. A pharmaceutical composition which comprises a transfection complex as claimed in claim 3 in admixture with a pharmaceutically suitable carrier.

5. A method for the treatment of a cancer in a human or in a non-human animal which comprises administering a transfection complex as claimed in claim 3 to the human or to the non-human animal by direct injection into protected tissues or general parenteral administration for non-protected tissues, wherein a target cell is transfected with the nucleic acid.

6. A peptide of formula A-B-C wherein:
A is a polycationic nucleic acid-binding component,
B is a spacer element peptide that is susceptible to cleavage by furin, and
C is a cell surface receptor binding component,
and wherein A, the polycationic nucleic acid-binding component, is an oligo-lysine molecule, an oligo-histidine molecule, an oligo-arginine molecule, an oligo-ornithine molecule, an oligo-diaminopropionic acid molecule or an oligo-diaminobutyric acid molecule or a combined oligomer comprising any combination of histidine, arginine, lysine, ornithine, diaminopropionic acid, and diaminobutyric acid residues or polyethylenimine (PEI);
B, the spacer element peptide, comprises the amino acid sequence RX$^1$KR [SEQ ID NO: 2] or RX$^2$RR [SEQ ID NO: 3] in which X$^1$ and X$^2$ which may be the same or different and each represent any amino acid residue;
and wherein C, the cell surface receptor binding component, comprises a peptide sequence selected from:
a) CRGDCLG [SEQ ID NO: 22];
b) CRGDCLG [SEQ ID NO: 22];
c) ACDCRGDCFCG [SEQ ID NO: 23];
d) CRGDMFGCA [SEQ ID NO: 24];
e) CRRETAWACG [SEQ ID NO: 25];
f) CRGEMFGCA [SEQ ID NO: 26];
g) CSERSMNFCG [SEQ ID NO: 27];
h) CYGLPHKFCG [SEQ ID NO: 28]; and
i) CLPHKSMPCG [SEQ ID NO: 29].

7. The peptide of claim 6 wherein A, the polycationic nucleic acid-binding component, is an oligo-lysine molecule.

8. The peptide of claim 6 wherein B, the spacer element peptide, comprises the amino acid sequence RVRR [SEQ ID NO: 3].

9. The peptide of claim 6 wherein C, cell surface receptor binding component, comprises the amino acid sequence CRGDCLG [SEQ ID NO: 22].

10. The peptide of claim 6, which is (K)$_{16}$RVR-RGACRGDCLG [SEQ ID NO: 30].

11. A non-viral delivery complex, for delivering genetic material when combined with a nucleic acid, that comprises:
(i) a peptide of formula A-B-C wherein
A is a polycationic nucleic acid-binding component,
B is a spacer element peptide that is susceptible to cleavage by furin, and
C is a cell surface receptor binding component,
and wherein A, the polycationic nucleic acid-binding component, is an oligo-lysine molecule, an oligo-histidine molecule, an oligo-arginine molecule, an oligo-ornithine molecule, an oligo-diaminopropionic acid molecule or an oligo-diaminobutyric acid molecule or a combined oligomer comprising any combination of histidine, arginine, lysine, ornithine, diaminopropionic acid, and diaminobutyric acid residues or polyethylenimine (PEI);
B, the spacer element peptide, comprises the amino acid sequence RX$^1$KR [SEQ ID NO: 2] or RX$^2$RR [SEQ ID NO: 3] in which X$^1$ and X$^2$ which may be the same or different and each represent any amino acid residue;
and wherein C, the cell surface receptor binding component, comprises a peptide sequence selected from:
a) CRGDCLG [SEQ ID NO: 22];
b) CRGDCLG [SEQ ID NO: 22];
c) ACDCRGDCFCG [SEQ ID NO: 23];
d) CRGDMFGCA [SEQ ID NO: 24];
e) CRRETAWACG [SEQ ID NO: 25];
f) CRGEMFGCA [SEQ ID NO: 26];
g) CSERSMNFCG [SEQ ID NO: 27];
h) CYGLPHKFCG [SEQ ID NO: 28]; and
i) CLPHKSMPCG [SEQ ID NO: 29];
and
(ii) a lipid of formula (III):

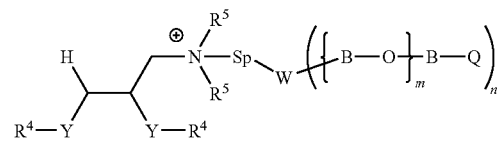

wherein:
each Y is the same or different and is selected from —O—, and —O—C(O)—;
each $R^4$ is the same or different and is selected from a straight or branched, saturated or unsaturated $C_{7-24}$ hydrocarbyl group which is unsubstituted or substituted by one or more substituents selected from hydroxy, halogen and OR', wherein R' is a $C_{1-6}$ hydrocarbyl group;
each $R^5$ is the same or different and is selected from a straight or branched, saturated or unsaturated $C_{1-10}$ hydrocarbyl group which is unsubstituted or substituted by one or more substituents selected from hydroxy, halogen, —OR', —C(O)OH, —CN, —N(R')₂, and —C(O)R', wherein each R' is the same or different and is a $C_{1-6}$ hydrocarbyl group;

Sp is a $C_{1-8}$ alkylene group which is unsubstituted or substituted by one or more substituents selected from hydroxy, halogen and OR', wherein R' is a $C_{1-6}$ hydrocarbyl group;

W is selected from —O—C(O)—, —C(O)O—, and the group of formula (IV):

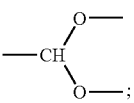

(IV)

n denotes the number of chains, and n=1 if the linker W is —O—C(O)— or —C(O)O—, and n=2 if the linker W is the group of formula (IV);

each B is the same or different and is a $C_{1-6}$ alkylene group which is unsubstituted or substituted by one or more substituents selected from hydroxy, halogen, —OR¹, —C(O)OH, —CN, —NR¹R², —C(O)OR¹, —OC(O)R¹ and —C(O)R¹;

R¹ and R² are the same or different and are $C_{1-4}$ hydrocarbyl;

m is an integer from 1 to 100; and

Q is selected from —N⁺(R³)₃, —OH, and —OR³ wherein R³ is an unsubstituted $C_{1-4}$ alkyl group or a trifluoromethyl group.

12. A non-viral transfection complex comprising the non-viral delivery complex as claimed in claim 11 and a nucleic acid.

13. A non-viral delivery complex, for delivering genetic material when combined with a nucleic acid, that comprises:
(i) a peptide of formula A-B-C wherein
A is a polycationic nucleic acid-binding component,
B is a spacer element peptide that is susceptible to cleavage by furin, and
C is a cell surface receptor binding component,
and wherein A, the polycationic nucleic acid-binding component, is an oligo-lysine molecule, an oligo-histidine molecule, an oligo-arginine molecule, an oligo-ornithine molecule, an oligo-diaminopropionic acid molecule or an oligo-diaminobutyric acid molecule or a combined oligomer comprising any combination of histidine, arginine, lysine, ornithine, diaminopropionic acid, and diaminobutyric acid residues or polyethylenimine (PEI);
B, the spacer element peptide, comprises the amino acid sequence RX¹KR [SEQ ID NO: 2] or RX²RR [SEQ ID NO: 3] in which X¹ and X² which may be the same or different and each represent any amino acid residue;
and wherein C, the cell surface receptor binding component, comprises a peptide sequence selected from:

a) CRGDCLG [SEQ ID NO: 22];
b) CRGDCLG [SEQ ID NO: 22];
c) ACDCRGDCFCG [SEQ ID NO: 23];
d) CRGDMFGCA [SEQ ID NO: 24];
e) CRRETAWACG [SEQ ID NO: 25];
f) CRGEMFGCA [SEQ ID NO: 26];
g) CSERSMNFCG [SEQ ID NO: 27];
h) CYGLPHKFCG [SEQ ID NO: 28]; and
i) CLPHKSMPCG [SEQ ID NO: 29];
and
(ii) a lipid of formula (VI):

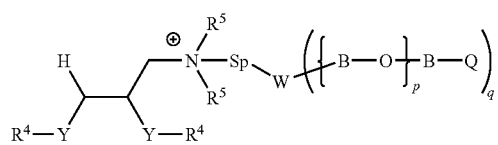

wherein:
each Y is the same or different and is selected from —O—, and —O—C(O)—;
each R⁴ is the same or different and is selected from a straight or branched, saturated or unsaturated $C_{7-24}$ hydrocarbyl group which is unsubstituted or substituted by one or more substituents selected from hydroxy, halogen and OR', wherein R' is a $C_{1-6}$ hydrocarbyl group;
each R⁵ is the same or different and is selected from a straight or branched, saturated or unsaturated $C_{1-10}$ hydrocarbyl group which is unsubstituted or substituted by one or more substituents selected from hydroxy, halogen, —OR', —C(O)OH, —CN, —N(R')₂, and —C(O)R', wherein each R' is the same or different and is a $C_{1-6}$ hydrocarbyl group;
Sp is a $C_{1-8}$ alkylene group which is unsubstituted or substituted by one or more substituents selected from hydroxy, halogen and OR', wherein R' is a $C_{1-6}$ hydrocarbyl group;
W is a group susceptible to cleavage within a cell;
q denotes the number of chains;
each B is the same or different and is a $C_{1-6}$ alkylene group which is unsubstituted or substituted by one or more substituents selected from hydroxy, halogen, —OR¹, —C(O)OH, —CN, —NR¹R², —C(O)OR¹, —OC(O)R¹ and —C(O)R¹;
R¹ and R² are the same or different and are $C_{1-4}$ hydrocarbyl;
p is an integer from 1 to 8; and
Q is selected from —N⁺(R³)₃, —OH, and —OR³ wherein R³ is an unsubstituted $C_{1-4}$ alkyl group or a trifluoromethyl group.

14. A non-viral transfection complex comprising the non-viral delivery complex as claimed in claim 13 and a nucleic acid.

* * * * *

SEQUENCE LISTING

```
<160> NUMBER OF SEQ ID NOS: 45

<210> SEQ ID NO 1
<211> LENGTH: 16
<212> TYPE: PRT
<213> ORGANISM: Artificial Sequence
<220> FEATURE:
<223> OTHER INFORMATION: Artificially Synthesised polycationic nucleic
      acid-binding component

<400> SEQUENCE: 1

Lys Lys Lys Lys Lys Lys Lys Lys Lys Lys Lys Lys Lys Lys Lys Lys
1               5                   10                  15

<210> SEQ ID NO 2
<211> LENGTH: 4
<212> TYPE: PRT
<213> ORGANISM: Artificial Sequence
<220> FEATURE:
<223> OTHER INFORMATION: Artificially synthesised spacer element peptide
      that is susceptible to cleavage within a cell
<220> FEATURE:
<221> NAME/KEY: MISC_FEATURE
<222> LOCATION: (2)..(2)
<223> OTHER INFORMATION: amino acid residue at position 2 is Lys (K) or
      Val (V)

<400> SEQUENCE: 2

Arg Xaa Lys Arg
1

<210> SEQ ID NO 3
<211> LENGTH: 4
<212> TYPE: PRT
<213> ORGANISM: Artificial Sequence
<220> FEATURE:
<223> OTHER INFORMATION: Artificially synthesised spacer element peptide
      that is susceptible to cleavage within a cell
<220> FEATURE:
<221> NAME/KEY: MISC_FEATURE
<222> LOCATION: (2)..(2)
<223> OTHER INFORMATION: amino acid residue at position 2 is Lys (K) or
      Val (V)
```

```
<400> SEQUENCE: 3

Arg Xaa Arg Arg
1

<210> SEQ ID NO 4
<211> LENGTH: 4
<212> TYPE: PRT
<213> ORGANISM: Artificial Sequence
<220> FEATURE:
<223> OTHER INFORMATION: Artificially synthesised spacer element peptide that is susceptible to cleavage within a cell
<220> FEATURE:
<221> NAME/KEY: MISC_FEATURE
<222> LOCATION: (3)..(3)
<223> OTHER INFORMATION: amino acid residue at position 3 is selected from Tyr (Y), Phe (F), Leu (L) and Val (V)
<220> FEATURE:
<221> NAME/KEY: MISC_FEATURE
<222> LOCATION: (4)..(4)
<223> OTHER INFORMATION: amino acid residue at position 4 is selected from Gly (G), Ala (A) and Glu (E)

<400> SEQUENCE: 4

Gly Phe Xaa Xaa
1

<210> SEQ ID NO 5
<211> LENGTH: 7
<212> TYPE: PRT
<213> ORGANISM: Artificial Sequence
<220> FEATURE:
<223> OTHER INFORMATION: Artificially synthesised cell surface receptor binding component

<400> SEQUENCE: 5

Arg Arg Glu Thr Ala Trp Ala
1 5

<210> SEQ ID NO 6
<211> LENGTH: 4
<212> TYPE: PRT
<213> ORGANISM: Artificial Sequence
<220> FEATURE:
<223> OTHER INFORMATION: Artificially synthesised cell surface receptor binding component
<220> FEATURE:
<221> NAME/KEY: MISC_FEATURE
<222> LOCATION: (2)..(2)
<223> OTHER INFORMATION: amino acid residue at position 2 is Gln (Q) or Pro (P)

<400> SEQUENCE: 6

Leu Xaa His Lys
1

<210> SEQ ID NO 7
<211> LENGTH: 7
<212> TYPE: PRT
<213> ORGANISM: Artificial Sequence
<220> FEATURE:
<223> OTHER INFORMATION: Artificially synthesised cell surface receptor binding component
<220> FEATURE:
<221> NAME/KEY: MISC_FEATURE
<222> LOCATION: (4)..(4)
<223> OTHER INFORMATION: amino acid residue at position 4 is Ala (A) or Thr (T)

<400> SEQUENCE: 7

Pro Ser Gly Xaa Ala Arg Ala

```
<210> SEQ ID NO 8
<211> LENGTH: 7
<212> TYPE: PRT
<213> ORGANISM: Artificial Sequence
<220> FEATURE:
<223> OTHER INFORMATION: Artificially synthesised cell surface receptor
      binding component
<220> FEATURE:
<221> NAME/KEY: MISC_FEATURE
<222> LOCATION: (2)..(2)
<223

```
Leu Pro His Lys Ser Met Pro
1               5

<210> SEQ ID NO 13
<211> LENGTH: 7
<212> TYPE: PRT
<213> ORGANISM: Artificial Sequence
<220> FEATURE:
<223> OTHER INFORMATION: Artificially synthesised cell surface receptor
      binding component

<400> SEQUENCE: 13

Val Lys Ser Met Val Thr His
1               5

<210> SEQ ID NO 14
<211> LENGTH: 7
<212> TYPE: PRT
<213> ORGANISM: Artificial Sequence
<220> FEATURE:
<223> OTHER INFORMATION: Artificially synthesised cell surface receptor
      binding component

<400> SEQUENCE: 14

Ser Glu Arg Ser Met Asn Phe
1               5

<210> SEQ ID NO 15
<211> LENGTH: 7
<212> TYPE: PRT
<213> ORGANISM: Artificial Sequence
<220> FEATURE:
<223> OTHER INFORMATION: Artificially synthesised cell surface receptor
      binding component

<400> SEQUENCE: 15

Val Gly Leu Pro His Lys Phe
1               5

<210> SEQ ID NO 16
<211> LENGTH: 7
<212> TYPE: PRT
<213> ORGANISM: Artificial Sequence
<220> FEATURE:
<223> OTHER INFORMATION: Artificially synthesised cell surface receptor
      binding component

<400> SEQUENCE: 16

Tyr Gly Leu Pro His Lys Phe
1               5

<210> SEQ ID NO 17
<211> LENGTH: 7
<212> TYPE: PRT
<213> ORGANISM: Artificial Sequence
<220> FEATURE:
<223> OTHER INFORMATION: Artificially synthesised cell surface receptor
      binding component

<400> SEQUENCE: 17

Ser Gln Arg Ser Met Asn Phe
1               5

<210> SEQ ID NO 18
<211> LENGTH: 7
<212> TYPE: PRT
<213> ORGANISM: Artificial Sequence
<220> FEATURE:
```

```
<223> OTHER INFORMATION: Artificially synthesised cell surface receptor
      binding component

<400> SEQUENCE: 18

Pro Ser Gly Thr Ala Arg Ala
1               5

<210> SEQ ID NO 19
<211> LENGTH: 5
<212> TYPE: PRT
<213> ORGANISM: Artificial Sequence
<220> FEATURE:
<223> OTHER INFORMATION: Cell surface receptor binding component
<220> FEATURE:
<221> NAME/KEY: MISC_FEATURE
<222> LOCATION: (2)..(2)
<223> OTHER INFORMATION: amino acid residue at position 2 is any amino
      acid residue
<220> FEATURE:
<221> NAME/KEY: MISC_FEATURE
<222> LOCATION: (3)..(3)
<223> OTHER INFORMATION: amino acid residue at position 3 is any amino
      acid residue
<220> FEATURE:
<221> NAME/KEY: MISC_FEATURE
<222> LOCATION: (4)..(4)
<223> OTHER INFORMATION: amino acid residue at position 4 is any amino
      acid residue

<400> SEQUENCE: 19

Pro Xaa Xaa Xaa Thr
1               5

<210> SEQ ID NO 20
<211> LENGTH: 4
<212> TYPE: PRT
<213> ORGANISM: Artificial Sequence
<220> FEATURE:
<223> OTHER INFORMATION: Artificially synthesised cell surface receptor
      binding component
<220> FEATURE:
<221> NAME/KEY: MISC_FEATURE
<222> LOCATION: (3)..(3)
<223> OTHER INFORMATION: amino acid residue at position 3 is any amino
      acid residue

<400> SEQUENCE: 20

Pro Ser Xaa Ser
1

<210> SEQ ID NO 21
<211> LENGTH: 5
<212> TYPE: PRT
<213> ORGANISM: Artificial Sequence
<220> FEATURE:
<223> OTHER INFORMATION: Artificially synthesised cell surface receptor
      binding component
<220> FEATURE:
<221> NAME/KEY: MISC_FEATURE
<222> LOCATION: (2)..(2)
<223> OTHER INFORMATION: amino acid residue at position 2 is any amino
      acid residue
<220> FEATURE:
<221> NAME/KEY: MISC_FEATURE
<222> LOCATION: (3)..(3)
<223> OTHER INFORMATION: amino acid residue at position 3 is any amino
      acid residue having an amide side chain
<220> FEATURE:
<221> NAME/KEY: MISC_FEATURE
<222> LOCATION: (4)..(4)
<223> OTHER INFORMATION: amino acid residue at position 4 is any amino
      acid residue
```

```
<400> SEQUENCE: 21

Gln Xaa Xaa Xaa Gln
1               5

<210> SEQ ID NO 22
<211> LENGTH: 7
<212> TYPE: PRT
<213> ORGANISM: Artificial Sequence
<220> FEATURE:
<223> OTHER INFORMATION: Artificially synthesised cell surface receptor
      binding component

<400> SEQUENCE: 22

Cys Arg Gly Asp Cys Leu Gly
1               5

<210> SEQ ID NO 23
<211> LENGTH: 11
<212> TYPE: PRT
<213> ORGANISM: Artificial Sequence
<220> FEATURE:
<223> OTHER INFORMATION: Artificially synthesised cell surface receptor
      binding component

<400> SEQUENCE: 23

Ala Cys Asp Cys Arg Gly Asp Cys Phe Cys Gly
1               5                   10

<210> SEQ ID NO 24
<211> LENGTH: 9
<212> TYPE: PRT
<213> ORGANISM: Artificial Sequence
<220> FEATURE:
<223> OTHER INFORMATION: Artificially synthesised cell surface receptor
      binding component

<400> SEQUENCE: 24

Cys Arg Gly Asp Met Phe Gly Cys Ala
1               5

<210> SEQ ID NO 25
<211> LENGTH: 10
<212> TYPE: PRT
<213> ORGANISM: Artificial Sequence
<220> FEATURE:
<223> OTHER INFORMATION: Artificially synthesised cell surface receptor
      binding component

<400> SEQUENCE: 25

Cys Arg Arg Glu Thr Ala Trp Ala Cys Gly
1               5                   10

<210> SEQ ID NO 26
<211> LENGTH: 9
<212> TYPE: PRT
<213> ORGANISM: Artificial Sequence
<220> FEATURE:
<223> OTHER INFORMATION: Artificially synthesised cell surface receptor
      binding component

<400> SEQUENCE: 26

Cys Arg Gly Glu Met Phe Gly Cys Ala
1               5

<210> SEQ ID NO 27
<211> LENGTH: 10
<212> TYPE: PRT
```

```
<213> ORGANISM: Artificial Sequence
<220> FEATURE:
<223> OTHER INFORMATION: Artificially synthesised cell surface receptor
      binding component

<400> SEQUENCE: 27

Cys Ser Glu Arg Ser Met Asn Phe Cys Gly
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Artificially synthesised cell surface receptor
      binding component

<400> SEQUENCE: 28

Cys Tyr Gly Leu Pro His Lys Phe Cys Gly
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Artificially synthesised Cell surface receptor
      binding component

<400> SEQUENCE: 29

Cys Leu Pro His Lys Ser Met Pro Cys Gly
1               5                   10

<210> SEQ ID NO 30
<211> LENGTH: 29
<212> TYPE: PRT
<213> ORGANISM: Artificial Sequence
<220> FEATURE:
<223> OTHER INFORMATION: Artificially synthesised peptide

<400> SEQUENCE: 30

Lys Lys Lys Lys Lys Lys Lys Lys Lys Lys Lys Lys Lys Lys Lys Lys
1               5                   10                  15

Arg Val Arg Arg Gly Ala Cys Arg Gly Asp Cys Leu Gly
            20                  25

<210> SEQ ID NO 31
<211> LENGTH: 30
<212> TYPE: PRT
<213> ORGANISM: Artificial Sequence
<220> FEATURE:
<223> OTHER INFORMATION: Artificially synthesised peptide

<400> SEQUENCE: 31

Lys Lys Lys Lys Lys Lys Lys Lys Lys Lys Lys Lys Lys Lys Lys Lys
1               5                   10                  15

Lys Val Arg Ala Arg Gly Ala Cys Arg Gly Asp Cys Leu Gly
            20                  25                  30

<210> SEQ ID NO 32
<211> LENGTH: 29
<212> TYPE: PRT
<213> ORGANISM: Artificial Sequence
<220> FEATURE:
<223> OTHER INFORMATION: Artificially synthesised peptide

<400> SEQUENCE: 32
```

```
Lys Lys Lys Lys Lys Lys Lys Lys Lys Lys Lys Lys Lys Lys Lys
1               5                   10                  15
Lys Val Lys Lys Gly Ala Cys Arg Gly Asp Cys Leu Gly
            20                  25

<210> SEQ ID NO 33
<211> LENGTH: 30
<212> TYPE: PRT
<213> ORGANISM: Artificial Sequence
<220> FEATURE:
<223> OTHER INFORMATION: Artificially synthesised peptide derivative
<220> FEATURE:
<221> NAME/KEY: MISC_FEATURE
<222> LOCATION: (17)..(17)
<223> OTHER INFORMATION: Xaa at position 17 is (PEG)4

<400> SEQUENCE: 33

Lys Lys Lys Lys Lys Lys Lys Lys Lys Lys Lys Lys Lys Lys Lys
1               5                   10                  15
Xaa Arg Val Arg Arg Gly Ala Cys Arg Gly Asp Cys Leu Gly
            20                  25                  30

<210> SEQ ID NO 34
<211> LENGTH: 31
<212> TYPE: PRT
<213> ORGANISM: Artificial Sequence
<220> FEATURE:
<223> OTHER INFORMATION: Artificially synthesised peptide derivative
<220> FEATURE:
<221> NAME/KEY: MISC_FEATURE
<222> LOCATION: (21)..(21)
<223> OTHER INFORMATION: Xaa at position 21 is (PEG)4

<400> SEQUENCE: 34

Lys Lys Lys Lys Lys Lys Lys Lys Lys Lys Lys Lys Lys Lys Lys
1               5                   10                  15
Arg Val Arg Arg Xaa Asn Gly Ala Cys Arg Gly Asp Cys Leu Gly
            20                  25                  30

<210> SEQ ID NO 35
<211> LENGTH: 33
<212> TYPE: PRT
<213> ORGANISM: Artificial Sequence
<220> FEATURE:
<223> OTHER INFORMATION: Artificially synthesised peptide

<400> SEQUENCE: 35

Lys Lys Lys Lys Lys Lys Lys Lys Lys Lys Lys Lys Lys Lys Lys
1               5                   10                  15
Arg Val Arg Arg Gly Ala Ala Cys Asp Cys Arg Gly Asp Cys Phe Cys
            20                  25                  30
Gly

<210> SEQ ID NO 36
<211> LENGTH: 31
<212> TYPE: PRT
<213> ORGANISM: Artificial Sequence
<220> FEATURE:
<223> OTHER INFORMATION: Artificially synthesised peptide

<400> SEQUENCE: 36

Lys Lys Lys Lys Lys Lys Lys Lys Lys Lys Lys Lys Lys Lys Lys
1               5                   10                  15
Arg Val Arg Arg Gly Ala Cys Arg Gly Asp Met Phe Gly Cys Ala
```

<210> SEQ ID NO 37
<211> LENGTH: 32
<212> TYPE: PRT
<213> ORGANISM: Artificial Sequence
<220> FEATURE:
<223> OTHER INFORMATION: Artificially synthesised peptide

<400> SEQUENCE: 37

```
Lys Lys Lys Lys Lys Lys Lys Lys Lys Lys Lys Lys Lys Lys Lys
1               5                   10                  15

Arg Val Arg Arg Gly Ala Cys Arg Arg Glu Thr Ala Trp Ala Cys Gly
            20                  25                  30
```

<210> SEQ ID NO 38
<211> LENGTH: 31
<212> TYPE: PRT
<213> ORGANISM: Artificial Sequence
<220> FEATURE:
<223> OTHER INFORMATION: Artificially synthesised peptide

<400> SEQUENCE: 38

```
Lys Lys Lys Lys Lys Lys Lys Lys Lys Lys Lys Lys Lys Lys Lys
1               5                   10                  15

Arg Val Arg Arg Gly Ala Cys Arg Gly Glu Met Phe Gly Cys Ala
            20                  25                  30
```

<210> SEQ ID NO 39
<211> LENGTH: 32
<212> TYPE: PRT
<213> ORGANISM: Artificial Sequence
<220> FEATURE:
<223> OTHER INFORMATION: Artificially synthesised peptide

<400> SEQUENCE: 39

```
Lys Lys Lys Lys Lys Lys Lys Lys Lys Lys Lys Lys Lys Lys Lys
1               5                   10                  15

Arg Val Arg Arg Gly Ala Cys Ser Glu Arg Ser Met Asn Phe Cys Gly
            20                  25                  30
```

<210> SEQ ID NO 40
<211> LENGTH: 32
<212> TYPE: PRT
<213> ORGANISM: Artificial Sequence
<220> FEATURE:
<223> OTHER INFORMATION: Artificially synthesised peptide

<400> SEQUENCE: 40

```
Lys Lys Lys Lys Lys Lys Lys Lys Lys Lys Lys Lys Lys Lys Lys
1               5                   10                  15

Arg Val Arg Arg Gly Ala Cys Tyr Gly Leu Pro His Lys Phe Cys Gly
            20                  25                  30
```

<210> SEQ ID NO 41
<211> LENGTH: 27
<212> TYPE: PRT
<213> ORGANISM: Artificial Sequence
<220> FEATURE:
<223> OTHER INFORMATION: Artificially synthesised peptide

<400> SEQUENCE: 41

```
Lys Lys Lys Lys Lys Lys Lys Lys Lys Lys Lys Lys Lys Lys Lys
1               5                   10                  15
```

```
Gly Ala Cys Arg Gly Asp Met Phe Gly Cys Ala
            20                  25

<210> SEQ ID NO 42
<211> LENGTH: 28
<212> TYPE: PRT
<213> ORGANISM: Artificial Sequence
<220> FEATURE:
<223> OTHER INFORMATION: Artificially synthesised peptide

<400> SEQUENCE: 42

Lys Lys Lys Lys Lys Lys Lys Lys Lys Lys Lys Lys Lys Lys Lys Lys
1               5                   10                  15

Gly Ala Cys Arg Arg Glu Thr Ala Trp Ala Cys Gly
            20                  25

<210> SEQ ID NO 43
<211> LENGTH: 27
<212> TYPE: PRT
<213> ORGANISM: Artificial Sequence
<220> FEATURE:
<223> OTHER INFORMATION: Artificially synthesised peptide

<400> SEQUENCE: 43

Lys Lys Lys Lys Lys Lys Lys Lys Lys Lys Lys Lys Lys Lys Lys Lys
1               5                   10                  15

Gly Ala Cys Arg Gly Glu Met Phe Gly Cys Ala
            20                  25

<210> SEQ ID NO 44
<211> LENGTH: 28
<212> TYPE: PRT
<213> ORGANISM: Artificial Sequence
<220> FEATURE:
<223> OTHER INFORMATION: Artificially synthesised peptide

<400> SEQUENCE: 44

Lys Lys Lys Lys Lys Lys Lys Lys Lys Lys Lys Lys Lys Lys Lys Lys
1               5                   10                  15

Gly Ala Cys Ser Glu Arg Ser Met Asn Phe Cys Gly
            20                  25

<210> SEQ ID NO 45
<211> LENGTH: 28
<212> TYPE: PRT
<213> ORGANISM: Artificial Sequence
<220> FEATURE:
<223> OTHER INFORMATION: Artificially synthesised peptide

<400> SEQUENCE: 45

Lys Lys Lys Lys Lys Lys Lys Lys Lys Lys Lys Lys Lys Lys Lys Lys
1               5                   10                  15

Gly Ala Cys Tyr Gly Leu Pro His Lys Phe Cys Gly
            20                  25
```